US006800748B2

(12) United States Patent
Holzberg et al.

(10) Patent No.: US 6,800,748 B2
(45) Date of Patent: Oct. 5, 2004

(54) CYTOPLASMIC INHIBITION OF GENE EXPRESSION AND EXPRESSION OF A FOREIGN PROTEIN IN A MONOCOT PLANT BY A PLANT VIRAL VECTOR

(75) Inventors: Steven P. Holzberg, Fairfield, CA (US); Gregory P. Pogue, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 217 days.

(21) Appl. No.: 09/771,009

(22) Filed: Jan. 25, 2001

(65) Prior Publication Data

US 2002/0157131 A1 Oct. 24, 2002

(51) Int. Cl.[7] .................. C07H 21/04; C07H 21/02; C12N 5/10; A01H 1/00; A01H 11/00
(52) U.S. Cl. .............. 536/23.4; 536/23.1; 435/419; 800/280; 800/282; 800/295; 800/320
(58) Field of Search .............. 536/23.1, 23.4; 435/419; 800/280, 282, 295, 320

(56) References Cited

U.S. PATENT DOCUMENTS

| | | | |
|---|---|---|---|
| 4,885,248 A | 12/1989 | Ahlquist | 435/172.3 |
| 5,173,410 A | 12/1992 | Ahlquist | 435/91 |
| 5,316,931 A | 5/1994 | Donson et al. | 435/172.3 |
| 5,466,788 A | 11/1995 | Ahlquist et al. | 536/24.1 |
| 5,491,076 A | 2/1996 | Carrington et al. | 435/70.1 |
| 5,500,360 A | 3/1996 | Ahlquist et al. | 435/172.3 |
| 5,539,093 A | 7/1996 | Fitzmaurice et al. | 536/23.2 |
| 5,589,367 A | 12/1996 | Donson et al. | 435/172.3 |
| 5,602,242 A | 2/1997 | Ahlquist et al. | 536/23.72 |
| 5,627,060 A | 5/1997 | Ahlquist et al. | 435/172.3 |
| 5,811,653 A | 9/1998 | Turpen | 800/205 |
| 5,866,785 A | 2/1999 | Donson et al. | 800/205 |
| 5,889,190 A | 3/1999 | Donson et al. | 800/288 |
| 5,922,602 A | 7/1999 | Kumagai et al. | 435/468 |
| 5,977,438 A | 11/1999 | Turpen et al. | 800/288 |

FOREIGN PATENT DOCUMENTS

| | | |
|---|---|---|
| WO | WO 92/18618 | 10/1992 |
| WO | WO 95/34668 A2 | 12/1995 |
| WO | WO 96-12027 | 4/1996 |
| WO | WO 97/42210 | 11/1997 |
| WO | WO 99/36516 | 7/1999 |
| WO | WO 99/61597 A2 | 12/1999 |

OTHER PUBLICATIONS

Zhang et al., "Expression of Reporter Genes asd Self–Cleaving Fusions with Barley Stripe Mosaic Virus Coat Protein", Phytopathology, vol. 87, No. 6, Suppl., 1997 p. S108.
Ahlquist, P., et al, "Complete nucleotide sequence of brome mosaic virus RNA3," *J. Mol. Biol.* 153:23–28 (1981).
Ausubel, Frederck, et al., *Current Protocols in Molecular Biology*, Greene Publishing and Wiley–Interscience, New York, (1987).
Bartley, G.E. and Scolnik, P.A., "Plant carotenoids: pigments for photoprotection, visual attraction, and human health", *Plant Cell* 7(7):1027–38 (1995).
Brunt, et al., "Plant Viruses Online: Descriptins and lists from the VIDE Database. Version: Jan. 16th." URL http://biology.anu.edu.au/Groups/MES/VIDE/Dallwitz (1980) (1996).
Chaplin, P.J., et al., "Production of interleukin–12 as a self–processing 2A polypeptide," Interfferon Cytokine Res. 19(3):235–241 (1999).
Choi, I., et al., "A plant virus vector for systemic expression of foreign genes in cereals" *The Plant Journal* 23(4):547–555 (2000).
Chrispeels and Raikhel, Plant Physiol. 122:1–2 (2000).
Crameri A., et al., "Improved green fluorescent protein by molecular evolution using DNA shuffling" *Nature Biotechnol* 14(3):315–9 (1996).
Dawson, W., et al., "Regulation of Tobamovirus Gene Expression," *Adv. Virus Res.*, 38:307–342 (1990).
DeFelipe, P. et al., "Use of the 2A sequence from foot–and–mouth disease virus in the generation of retroviral vectors for gene therapy" *Gene Ther.* 6(2):198–208 (1999).
DeFelipe, P., and Izquierdo, M., "Tricistronic and tetracistronic retroviral vectors for gene transfer" *Hum. Gene Ther.* 11(13):1921–31 (2000).
DeNoto, F.M., et al., "Human Growth hormone DNA sequence and mRNA structure: possible alternative splicing," *Nucleic Acids Res.* 9:3719–3730 (1981).
Digby, M.R. and Lowenthal, J.W.., "Cloning and Expression of the Chicken Interferon–y Gene," *J. Interferon Cytokine Res.* 15(11):939–945 (1995).
Dijkstra, J., et al., *Practical Plant Virology: Protocols and Exercises*, Springer Verlag (1998).
Donald, R.G. and Andrew Jackson,. "The Barley Stripe Mosaic Virus Yb Gene Encodes a Multifunctional Cysteine–Rich Protein That Affects Pathogenesis," *The Plant Cell*, 6:1593–1606 (1994).
Donnelly, M., et al., "The Cleavage activities of aphthovirus and cardiovirus 2A proteins," Journal of Gen. Vio., 78: 13–21 (1997).
Donson, J., et al., "Agrobacterium–Mediated Infectivity of Cloned Digitaria Streak Virus DNA," *Virology* 162:248–250 (1988).

(List continued on next page.)

*Primary Examiner*—Elizabeth F. McElwain
*Assistant Examiner*—Georgia L. Helmer
(74) *Attorney, Agent, or Firm*—Thomas Gallegos; John C. Robbins; Quine Intellectual Property Law Group, P.C.

(57) ABSTRACT

The present invention relates to recombinant viral vectors encoding a transcriptional unit, that encodes a fusion protein, or a foreign protein or a gene of interest to be silenced, which can be expressed in a host. The present invention also relates to the use of these recombinant viral vectors to express a fusion protein, a foreign protein, to silence a gene of interest in a host. The present invention also relates to the use of these recombinant viral vectors to screen a cDNA or genomic library in order to correlate a nucleotide sequence with a phenotypic or biochemical change.

25 Claims, 27 Drawing Sheets

OTHER PUBLICATIONS

Elmer, J. Scott., et al., "Agrobacterium–mediated inoculation of plants with tomato golden mosaic virus DNA," *Plant Mol. Biol.* 10:225–234 (1988).

Fukuda, M., et al., "The Site of Initiation of Rod Assembly on the RNA of a Tomoato and a Cowpea Strain of Tobacco Mosaic Virus," *Virology* 101:493–502 (1980).

Gardiner, W., et al., "Genetic analysis of tomato golden mosaic virus: the coat protein is not required for systemic or symptom development," *EMBO J.* 7:899–904 (1988).

Gardner,R., et al., "Potato spindle tuber viroid infections mediated by the Ti plasmid of Agrobacterium tumefaciens," *Plant Mol. Biol.* 6:221–228 (1986).

Gopinath, K., et al., "Engineering cowpea mosaic virus RNA–2 into a vector to express heterologous proteins in plants," *Virol.* 267(2):159–173 (2000).

Graham J.S., et al.,"Wound–induced proteinase inhibitors from tomato leaves. I. The cDNA–deduced primary structure of pre–inhibitor I and its post–translational processing," *J Biol. Chem.*, 260(11):6555–6560 (1985).

Grimsley, N., et al., Agrobacterium–mediated delivery of infectious maize streak virus into maize plants, *Nature* 325:177–179 (1987).

Grimsley, N., et al., "Agroinfection, an alternative route for viral infection of plants by using the Ti plasmid," *Proc. Natl. Acad. Sci. USA* 83:3282–3286 (1986).

Halpin, C., et al., "Self–processing 2A–polyproteins–a system fpr co–ordinate expression of multiple proteins in transgenic plants," Plants J. 17(4):453–459 (1999).

Haupt, S., et al., "Evidence of Symplastic Phloem unloading in sink leaves of barley," Plant Physiology (in press) 125:209–218 (2001).

Hayes, R.J., et al., "Agroinfection of Triticum aestivum with cloned DNA of Wheat Dwarf Virus," *J. Gen. Virol.* 69:891–896 (1988).

Jackson, A.O., and Hunter, B.G., "Hordeivirus relationships and genome organization," *Annu. Rev. Phytopathol.* 2795–121 (1989).

Jackson, A.O., et al., "Analysis of barley stripe mosaic virus pathogenicity," *Sem. Virol.* 2:107–19 (1991).

Jarvik, J.W., and Telmer C.A., "Epitope tagging", *Annu Rev Genet.*, 32601–618 (1998).

Joshi, R.L., et al., "BSMV genome mediated expression of a foreign gene in dicot and monocot plant cells," *EMBO* 9:2663–2669 (1998).

Kanegae, T., et al., "Species–Dependent Expression of the Hyoscyamine 6B–Hydroxylase Gene in the Pericycle," *Plant Physiol* 105(2):483–490 (1994).

Kokuho, T., et al., "Production of biologically active, geterodimeric porcine interleukin–12 using a monocistronic baculoviral expression system," Vet. Immunol. Immunopathol. 72:(3–4):289–302 (1999).

Kumagai, M.H., et al. "Cytoplasmic inhibition of carotenoid biosynthesis with virus–derived RNA," *Proc. Natl. Acad. Sci. USA* 92:1679–1683 (1995).

Kurisu, M., et al., "Biochemical Characterization of Cucumber Green Mottle Mosaic Virus Ribonucleic Acid," *Virol.* 70:214–216 (1976).

Lazarowitz, S., "Infectivity and complete nucleotide sequence of the genome of a South African isolate of maize streak virus," *Nucl. Acids Res.* 16(1):229–249 (1988).

Lebeurier, G., et al., "Inside–out model for self–assembly of tobacco virus," *Proc. Natl. Acad. Sci. USA* 74(1):149–153 (1977).

Li, Feng., et al., "Equine rhinovirus 1 is more closely related to foot–and–mouth disease virus than to other picomaviruses," Proc. Natl. Acad. Sci. USA 93:990–995 (1996).

Liu, Y.G.,et al., Completmentation of plant mutants with large genomic DNA fragments by transformation–competent artificial chromosome vector accelerates positional cloning, *Proc. Natl. Acad. Sci. USA,* 96:6535–6540 (1999).

Matthews, R.E.F., Virol. $3^{rd.}$ Ed. Academic Press, San Diego, (1991).

Mattion, N.M., et al., "Foot–and–mouth disease virus 2A protease mediates cleavage in attenuated Sabin 3 poliovirus vectors engineered for delivery of foreign antigens," *J. Virol.* 70(11):8124–8127 (1996).

McKinney H.H., and Greeley, L.W., "Biological characteristics of barley stripe mosaic virus strains and their evolution," *Technical Bulletin U.S. Department of Agriculture* 1324 (1965).

Meshi, T., et al., "Nucleotide Sequence of the Coat Protein Cistron and the 3' Noncoding Region of Cucumber Green Mottle Mosaic Virus (Watermelon Strain) RNA," *Virology* 12754–64 (1983).

Methods in Enzymol. (vols. 68, 100, 101, 118 and 152–155) (1979, 1983, 1986 and 1987).

Miller, J. *Experiments in Molecular Genetics*, Cold Spring Harbor Laboratory, New York (1972).

Nagar, S., et al., "A Geminivirus Induces Expression of a Host DNA Synthesis Protein in Terminally Differentiated Plant Cells," *Plant Cell* 7:705–719 (1995).

Napoli, C., et al., "Introduction of a Chimeric Chalcone Synthase Gene into Petunia Results in Reversible Co–Suppression of Homologous Genes in trans," *The Plant Cell* 2:279–289 (1990).

Ogawa, T., et al., "Trans Complementation of Virus–Encoded Replicase Components of Tobacco Mosaic Virus," *Virology,* 185580–584 (1991).

R.W. Old and S.B. Primrose, *Principles of Gene Manipulation* $5^{th}$ ed., Blackwell Science, Oxford, U.K. (1994).

Palmenberg, A.C., "Proteolytic processing of picornaviral polyprotein," *Annu. Rev. Microbiol.* 44:603–623 (1990).

Palomar, M.K., et al. "Base sequence homology in the RNAs of barley stripe mosaic virus," *Virol.* 77(2):471–480 (1977).

Petty, I.T., et al. "Identification of barley stripe mosaic virus genes involved in viral RNA replication and movement," *EMBO Journal* 9:3453–3457 (1990).

Petty, I.T., et al. "Infectious barley stripe mosaic virus RNA transcribed in vitro from full–length genomic cDNA clones," *Virol.* 171(2):342–349 (1989).

Plant Virology Protocol: From Virus Isolation to Transgenic Resistance in Methods in molecular Biology, vol. 81, Foster & Taylor, Ed., Humana Press (1998).

Pogue, G.P., et al., "Tobamovirus transient expression vectors:Tools for plant biology and high–lvel expression of foreign proteins in plants," Plant Mol. Biology Manuel (S.B. Gelvin and R.A. Schilperoot, eds.) L4, pp. 1–27 (1998) Kluwer Acdemic Publishers, Dorfercht, The Netherlands.

Ryan, M.D., and Drew, J. "Foot–and–mouth disease virus 2A oligopeptide mediated cleavage of an artificial polyprotein," *EMBO Journal* 13(4):928–933 (1994).

Ryan, M.D., et al., "Cleavage of foot–and–mouth disease virus polyprotein is mediated by residues located within a 19 amino acid sequence," 72(Pt 11):2727–2732 (1991).

Turpen, T., et al., "Transfection of whole plants from wounds inoculated with Agrobacterium tumefaciens containing cDNA of tobacco mosaic virus," *J. of Virological Methods* 42:227–240 (1993).

Van Lijsebettens,M., et al., "An S18 ribosomal protein gene copy of the Arabidopsis PFL locus affects plant development by its specific expression in meristems," *EMBO J.* 13(14):33768–3388 (1994).

Velculescu, V., et al., "Characterization of the Yeast Transcriptome," *Cell* 88:243–251 (1997).

Walkey, D.G.A., *Applied Plant Virol., Chapman & Hall ed.* (1991).

Weiland, J.J., and Edwards M.C., "A single nucleotide substitution in the alpha a gene confers oat pathogenicity to barley stripe mosaic virus strain ND18," *MPMI* 9(1):62–67 (1996).

Zhang, L., et al. "Gene Expression Profiles in Normal and Cancer Cells," *Science* 276:1268–1272 (1997).

Zhou, H., and Jackson, A.O., "Expression of the barley stripe mosaic virus RNA beta 'triple gene block',". *Virol.* 16(2):367–379 (1998).

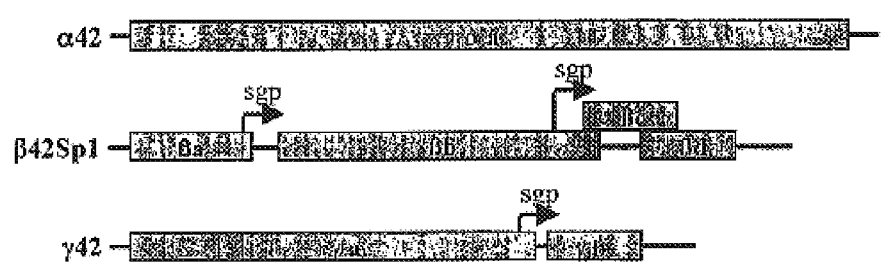

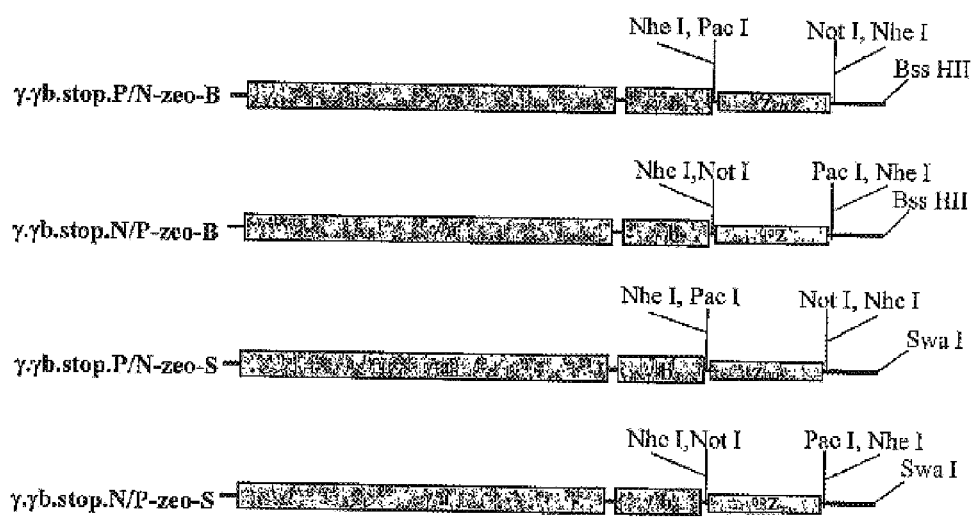

Anti-BMV-CP

Anti-chIF

Anti-boLys

Anti-hGH

Anti-tPI1

γ- Δγb.GFPc3

SEQUENCE LISTING

```
<160> NUMBER OF SEQ ID NOS: 74

<210> SEQ ID NO 1
<211> LENGTH: 17
<212> TYPE: PRT
<213> ORGANISM: Coxsackie virus

<400> SEQUENCE: 1

Asn Phe Asp Leu Leu Lys Leu Ala Gly Asp Val Glu Ser Asn Pro Gly
1               5                   10                  15

Pro

<210> SEQ ID NO 2
<211> LENGTH: 20
<212> TYPE: PRT
<213> ORGANISM: Coxsackie virus

<400> SEQUENCE: 2

Gln Leu Leu Asn Phe Asp Leu Leu Lys Leu Ala Gly Asp Val Glu Ser
1               5                   10                  15

Asn Leu Gly Pro
            20

<210> SEQ ID NO 3
<211> LENGTH: 20
<212> TYPE: PRT
<213> ORGANISM: Coxsackie virus

<400> SEQUENCE: 3

Gln Leu Leu Asn Phe Asp Leu Leu Lys Leu Ala Gly Asp Val Glu Ser
1               5                   10                  15

Asn Pro Arg Pro
            20

<210> SEQ ID NO 4
<211> LENGTH: 20
```

-continued

```
<212> TYPE: PRT
<213> ORGANISM: Coxsackie virus

<400> SEQUENCE: 4

Gln Leu Leu Asn Phe Asp Leu Leu Lys Leu Ala Gly Asp Val Glu Ser
 1               5                  10                  15

Asn Pro Gly Pro
            20

<210> SEQ ID NO 5
<211> LENGTH: 20
<212> TYPE: PRT
<213> ORGANISM: Coxsackie virus

<400> SEQUENCE: 5

Gln Thr Leu Asn Phe Asp Leu Leu Lys Leu Ala Gly Asp Val Glu Ser
 1               5                  10                  15

Asn Pro Gly Pro
            20

<210> SEQ ID NO 6
<211> LENGTH: 20
<212> TYPE: PRT
<213> ORGANISM: Coxsackie virus

<400> SEQUENCE: 6

Gln Leu Leu Asn Phe Asp Leu Leu Lys Leu Ala Gly Asp Val Glu Ser
 1               5                  10                  15

Asn Pro Gly Pro
            20

<210> SEQ ID NO 7
<211> LENGTH: 20
<212> TYPE: PRT
<213> ORGANISM: Coxsackie virus

<400> SEQUENCE: 7

His Tyr Ala Gly Tyr Phe Ala Asp Leu Leu Ile His Asp Ile Glu Thr
 1               5                  10                  15

Asn Pro Gly Pro
            20

<210> SEQ ID NO 8
<211> LENGTH: 20
<212> TYPE: PRT
<213> ORGANISM: Coxsackie virus

<400> SEQUENCE: 8

His Tyr Ala Gly Tyr Phe Ser Asp Leu Leu Ile His Asp Val Glu Thr
 1               5                  10                  15

Asn Pro Gly Pro
            20

<210> SEQ ID NO 9
<211> LENGTH: 20
<212> TYPE: PRT
<213> ORGANISM: Coxsackie virus

<400> SEQUENCE: 9

Tyr His Ala Asp Tyr Tyr Lys Gln Arg Leu Ile His Asp Val Glu Met
 1               5                  10                  15

Asn Pro Gly Pro
```

```
<210> SEQ ID NO 10
<211> LENGTH: 19
<212> TYPE: PRT
<213> ORGANISM: Coxsackie virus

<400> SEQUENCE: 10

Gln Leu Leu Asn Phe Asp Leu Leu Lys Leu Ala Gly Asp Val Glu Ser
  1               5                  10                  15

Asn Pro Gly

<210> SEQ ID NO 11
<211> LENGTH: 28
<212> TYPE: DNA
<213> ORGANISM: Barley stripe mosaic virus

<400> SEQUENCE: 11
cttcttccgt tgctagctaa aaaaaaaa                                      28

<210> SEQ ID NO 12
<211> LENGTH: 21
<212> TYPE: DNA
<213> ORGANISM: Barley stripe mosaic virus

<400> SEQUENCE: 12
agttacttct tgaatttctc c                                             21

<210> SEQ ID NO 13
<211> LENGTH: 39
<212> TYPE: DNA
<213> ORGANISM: Barley stripe mosaic virus

<400> SEQUENCE: 13
tatagcgcgc atttaaattg gtcttccctt gggggaccg                          39

<210> SEQ ID NO 14
<211> LENGTH: 49
<212> TYPE: DNA
<213> ORGANISM: Saccharomyces cerevisiae

<400> SEQUENCE: 14
tatgctagct gattaattaa gtcgacgagc tgatttaaca aattttaac               49

<210> SEQ ID NO 15
<211> LENGTH: 44
<212> TYPE: DNA
<213> ORGANISM: Saccharomyces cerevisiae

<400> SEQUENCE: 15
tatgctagct gagcggccgc gcacgtgtca gtcctgctcc tcgg                    44

<210> SEQ ID NO 16
<211> LENGTH: 46
<212> TYPE: DNA
<213> ORGANISM: Barley stripe mosaic virus

<400> SEQUENCE: 16
tatactagtt taattaagtc gaccatggct agcaaaggag aagaac                  46

<210> SEQ ID NO 17
<211> LENGTH: 44
<212> TYPE: DNA
```

-continued

```
<213> ORGANISM: Barley stripe mosaic virus

<400> SEQUENCE: 17
tatactagtt gagcggccgc ttatttgtag agctcatcca tgcc                    44

<210> SEQ ID NO 18
<211> LENGTH: 43
<212> TYPE: DNA
<213> ORGANISM: Barley stripe mosaic

<400> SEQUENCE: 18
tatagagctc tacaaatcta gaatggctac tttctcttgt gtg                     43

<210> SEQ ID NO 19
<211> LENGTH: 21
<212> TYPE: DNA
<213> ORGANISM: Barley stripe mosaic virus

<400> SEQUENCE: 19
agagtccgtt aagattcatg g                                             21

<210> SEQ ID NO 20
<211> LENGTH: 30
<212> TYPE: DNA
<213> ORGANISM: Tobacco mosaic virus

<400> SEQUENCE: 20
cattaattaa gatgatggct agcaaaggag                                    30

<210> SEQ ID NO 21
<211> LENGTH: 112
<212> TYPE: DNA
<213> ORGANISM: Tobacco mosaic virus

<400> SEQUENCE: 21
atatctagac ctaggaccag ggttagattc cacgtcaccc gccaacttca gcaaatcaaa    60
attcaacagc tgtttgtaga gctcagcggc cgccttgtat agctcatcca tg           112

<210> SEQ ID NO 22
<211> LENGTH: 98
<212> TYPE: DNA
<213> ORGANISM: Tobacco mosaic virus

<400> SEQUENCE: 22
tatactagtc agctgttgaa ttttgatttg ctgaagttgg cgggtgacgt ggaatctaac    60
cctggtcctg tcgacaaagg agaagaactt ttcactgg                            98

<210> SEQ ID NO 23
<211> LENGTH: 49
<212> TYPE: DNA
<213> ORGANISM: Tobacco mosaic virus

<400> SEQUENCE: 23
tatgctagcg atcaattagc ggccgcttat ttgtagagct catccatgc               49

<210> SEQ ID NO 24
<211> LENGTH: 39
<212> TYPE: DNA
<213> ORGANISM: Homo sapiens

<400> SEQUENCE: 24
ggccgcttat ccgtatgatg ttccggatta tgccgagct                           39
```

```
<210> SEQ ID NO 25
<211> LENGTH: 31
<212> TYPE: DNA
<213> ORGANISM: Homo sapiens

<400> SEQUENCE: 25
cggcataatc cggaacatca tacggataag c                           31

<210> SEQ ID NO 26
<211> LENGTH: 42
<212> TYPE: DNA
<213> ORGANISM: Chicken

<400> SEQUENCE: 26
ggccgctgaa caaaagctta tctctgagga agatcttgag ct               42

<210> SEQ ID NO 27
<211> LENGTH: 34
<212> TYPE: DNA
<213> ORGANISM: Chicken

<400> SEQUENCE: 27
caagatcttc ctcagagata agcttttgtt cagc                        34

<210> SEQ ID NO 28
<211> LENGTH: 39
<212> TYPE: DNA
<213> ORGANISM: Cnidaria

<400> SEQUENCE: 28
ggccgctcat catcaccatc accatcacca tcacgagct                   39

<210> SEQ ID NO 29
<211> LENGTH: 31
<212> TYPE: DNA
<213> ORGANISM: Cnidaria

<400> SEQUENCE: 29
cgtgatggtg atggtgatgg tgatgatgag c                           31

<210> SEQ ID NO 30
<211> LENGTH: 32
<212> TYPE: DNA
<213> ORGANISM: Brome mosaic virus

<400> SEQUENCE: 30
tatttaatta agatgtcgac ttcaggaact gg                          32

<210> SEQ ID NO 31
<211> LENGTH: 30
<212> TYPE: DNA
<213> ORGANISM: Brome mosaic virus

<400> SEQUENCE: 31
tatgcggccg ccctataaag cggggtgaag                             30

<210> SEQ ID NO 32
<211> LENGTH: 33
<212> TYPE: DNA
<213> ORGANISM: Chicken

<400> SEQUENCE: 32
```
tatttaatta agatgacttg ccagacttac aac                33

<210> SEQ ID NO 33
<211> LENGTH: 31
<212> TYPE: DNA
<213> ORGANISM: Chicken

<400> SEQUENCE: 33
tatgcggccg cgcaattgca tctcctctga g                  31

<210> SEQ ID NO 34
<211> LENGTH: 34
<212> TYPE: DNA
<213> ORGANISM: Bovine

<400> SEQUENCE: 34
tatttaatta agatgaaggc tctcgttatt ctgg               34

<210> SEQ ID NO 35
<211> LENGTH: 30
<212> TYPE: DNA
<213> ORGANISM: Bovine

<400> SEQUENCE: 35
tatgcggccg ccagggtgca accctcaacg                    30

<210> SEQ ID NO 36
<211> LENGTH: 38
<212> TYPE: DNA
<213> ORGANISM: Homo sapiens

<400> SEQUENCE: 36
tatttaatta agatgggaaa aatggcttct ctatttgc           38

<210> SEQ ID NO 37
<211> LENGTH: 33
<212> TYPE: DNA
<213> ORGANISM: Homo sapiens

<400> SEQUENCE: 37
tatgcggccg cgaaaccgca ggaaccttca acg                33

<210> SEQ ID NO 38
<211> LENGTH: 33
<212> TYPE: DNA
<213> ORGANISM: Tomato

<400> SEQUENCE: 38
tatttaatta agatggagtc aaagtttgct cac                33

<210> SEQ ID NO 39
<211> LENGTH: 33
<212> TYPE: DNA
<213> ORGANISM: Tomato

<400> SEQUENCE: 39
tatttaatta agatggagtc aaagtttgct cac                33

<210> SEQ ID NO 40
<211> LENGTH: 25
<212> TYPE: DNA
<213> ORGANISM: Barley stripe mosaic virus

<400> SEQUENCE: 40

```
atagatatcg atccccttat agtgc                                    25

<210> SEQ ID NO 41
<211> LENGTH: 34
<212> TYPE: DNA
<213> ORGANISM: Barley stripe mosaic virus

<400> SEQUENCE: 41
atagctagca agcatgcgaa ggtaaataca gtag                          34

<210> SEQ ID NO 42
<211> LENGTH: 46
<212> TYPE: DNA
<213> ORGANISM: Barley stripe mosaic virus

<400> SEQUENCE: 42
tatactagtt taattaagtc gaccatggct agcaaaggag aagaac             46

<210> SEQ ID NO 43
<211> LENGTH: 44
<212> TYPE: DNA
<213> ORGANISM: Barlesy stripe mosaic virus

<400> SEQUENCE: 43
tattctagat gagcggccgc ttatttgtag agctcatcca tgcc               44

<210> SEQ ID NO 44
<211> LENGTH: 46
<212> TYPE: DNA
<213> ORGANISM: Barley stripe mosaic virus

<400> SEQUENCE: 44
tatagagctc tacaaataat ctagaatggc tactttctct tgtgtg             46

<210> SEQ ID NO 45
<211> LENGTH: 21
<212> TYPE: DNA
<213> ORGANISM: Barley stripe mosaic virus

<400> SEQUENCE: 45
agagtccgtt aagattcatg g                                        21

<210> SEQ ID NO 46
<211> LENGTH: 35
<212> TYPE: DNA
<213> ORGANISM: Barley stripe mosaic virus

<400> SEQUENCE: 46
atataggtct cccatgatgg ctactttctc ttgtg                         35

<210> SEQ ID NO 47
<211> LENGTH: 39
<212> TYPE: DNA
<213> ORGANISM: Barley stripe mosaic virus

<400> SEQUENCE: 47
tattaggtct cccatggcct tagaaacgga agaagaatc                     39

<210> SEQ ID NO 48
<211> LENGTH: 35
<212> TYPE: DNA
<213> ORGANISM: Barley stripe mosaic virus
```

<210> SEQ ID NO 48

<400> SEQUENCE: 48 ataggtct cccatgatgg ctactttctc ttgtg                35

<210> SEQ ID NO 49
<211> LENGTH: 37
<212> TYPE: DNA
<213> ORGANISM: Barley stripe mosaic virus

<400> SEQUENCE: 49
tattaggtct cccatggcag gaccagggtt agattcc            37

<210> SEQ ID NO 50
<211> LENGTH: 21
<212> TYPE: DNA
<213> ORGANISM: Barley stripe mosaic virus

<400> SEQUENCE: 50
ggaaagccgg cgaacgtggc g                             21

<210> SEQ ID NO 51
<211> LENGTH: 58
<212> TYPE: DNA
<213> ORGANISM: Barley stripe mosaic virus

<400> SEQUENCE: 51
tatattcgaa tctagaatcg atgctagctt gcatgctgtg aagtggtaaa agaaatgc    58

<210> SEQ ID NO 52
<211> LENGTH: 35
<212> TYPE: DNA
<213> ORGANISM: Tobacco mosaic virus

<400> SEQUENCE: 52 ataggtct cccatggcta gcaaaggaga agaac                35

<210> SEQ ID NO 53
<211> LENGTH: 48
<212> TYPE: DNA
<213> ORGANISM: Tobacco mosaic virus

<400> SEQUENCE: 53
tattaggtct cacatgcatg ctctagattt gtagagctca tccatgcc    48

<210> SEQ ID NO 54
<211> LENGTH: 35
<212> TYPE: DNA
<213> ORGANISM: Tobacco mosaic virus

<400> SEQUENCE: 54 ataggtct cccatggcta gcaaaggaga agaac                35

<210> SEQ ID NO 55
<211> LENGTH: 100
<212> TYPE: DNA
<213> ORGANISM: Tobacco mosaic virus

<400> SEQUENCE: 55
ttaggtctca catgtctaga ggaccagggt tagattccac gtcacccgcc aacttcagca    60
aatcaaaatt caacagctgt tgtagagct catccatgcc                         100

<210> SEQ ID NO 56
<211> LENGTH: 35

-continued

```
<212> TYPE: DNA
<213> ORGANISM: Tobacco mosaic virus

<400> SEQUENCE: 56
atataggtct cccatggcta gcaaaggaga agaac                        35

<210> SEQ ID NO 57
<211> LENGTH: 41
<212> TYPE: DNA
<213> ORGANISM: Tobacco mosaic virus

<400> SEQUENCE: 57
tattagaatt ctctagatta tttgtagagc tcatccatgc c                 41

<210> SEQ ID NO 58
<211> LENGTH: 31
<212> TYPE: DNA
<213> ORGANISM: Barley stripe mosaic virus

<400> SEQUENCE: 58
tatactagta tggacatgac gaaaactgtt g                            31

<210> SEQ ID NO 59
<211> LENGTH: 31
<212> TYPE: DNA
<213> ORGANISM: Barley stripe mosaic virus

<400> SEQUENCE: 59
tatgctagct tatttggcct tgaaccaact g                            31

<210> SEQ ID NO 60
<211> LENGTH: 31
<212> TYPE: DNA
<213> ORGANISM: Barley stripe mosaic virus

<400> SEQUENCE: 60
tatactagtc agctgttgaa ttttgatttg c                            31

<210> SEQ ID NO 61
<211> LENGTH: 35
<212> TYPE: DNA
<213> ORGANISM: Black hulless barley

<400> SEQUENCE: 61
atattaatta actaaaccca tattgcttga ggcaa                        35

<210> SEQ ID NO 62
<211> LENGTH: 35
<212> TYPE: DNA
<213> ORGANISM: Black hulless barley

<400> SEQUENCE: 62
tatgcggccg cctagtgtag tcaccagcta gatag                        35

<210> SEQ ID NO 63
<211> LENGTH: 35
<212> TYPE: DNA
<213> ORGANISM: Black hulless barley

<400> SEQUENCE: 63
tatgcggccg cctactttca ggaggattac catcc                        35

<210> SEQ ID NO 64
```

```
<211> LENGTH: 35
<212> TYPE: DNA
<213> ORGANISM: Black hulless barley

<400> SEQUENCE: 64
atattaatta actggatgaa aaagcagggt gttcc                              35

<210> SEQ ID NO 65
<211> LENGTH: 32
<212> TYPE: DNA
<213> ORGANISM: Corn leaf

<400> SEQUENCE: 65
atattaatta acatggacac tggctgcctg tc                                 32

<210> SEQ ID NO 66
<211> LENGTH: 35
<212> TYPE: DNA
<213> ORGANISM: Corn leaf

<400> SEQUENCE: 66
tatgcggccg cctacaaagc aatcaaaatg cactg                              35

<210> SEQ ID NO 67
<211> LENGTH: 34
<212> TYPE: DNA
<213> ORGANISM: Corn leaf

<400> SEQUENCE: 67
atattaatta acaaggtagc tgcttggaag gatg                               34

<210> SEQ ID NO 68
<211> LENGTH: 35
<212> TYPE: DNA
<213> ORGANISM: Corn leaf

<400> SEQUENCE: 68
tatgcggccg cctagcaggt tactgacatg tctgc                              35

<210> SEQ ID NO 69
<211> LENGTH: 33
<212> TYPE: DNA
<213> ORGANISM: Corn leaf

<400> SEQUENCE: 69
atattaatta accagtgcat tttgattgct ttg                                33

<210> SEQ ID NO 70
<211> LENGTH: 35
<212> TYPE: DNA
<213> ORGANISM: Corn leaf

<400> SEQUENCE: 70
tatgcggccg cctaagatgg gacgggaact tctcc                              35

<210> SEQ ID NO 71
<211> LENGTH: 35
<212> TYPE: DNA
<213> ORGANISM: Nicotiana benthamiana

<400> SEQUENCE: 71
atattaatta acatgcccca aattggactt gtttc                              35
```

-continued

```
<210> SEQ ID NO 72
<211> LENGTH: 35
<212> TYPE: DNA
<213> ORGANISM: Nicotiana benthamiana

<400> SEQUENCE: 72
tatgcggccg cctactaaac tacgcttgct tctgc                              35

<210> SEQ ID NO 73
<211> LENGTH: 35
<212> TYPE: DNA
<213> ORGANISM: Nicotiana benthamiana

<400> SEQUENCE: 73
tatgcggccg cctagggttt atgaagttaa gtgcc                              35

<210> SEQ ID NO 74
<211> LENGTH: 35
<212> TYPE: DNA
<213> ORGANISM: Nicotiana benthamiana

<400> SEQUENCE: 74
atattaatta acaaggcact taacttcata aaccc                              35
```

CYTOPLASMIC INHIBITION OF GENE EXPRESSION AND EXPRESSION OF A FOREIGN PROTEIN IN A MONOCOT PLANT BY A PLANT VIRAL VECTOR

FIELD OF THE INVENTION

The present invention relates to the field of molecular biology and genetics. Specifically, the invention relates to the use of recombinant viruses and recombinant viral vectors in expressing foreign peptides and/or regulating gene expression in a plant host.

BACKGROUND OF THE INVENTION

Virus expression vectors allow rapid expression of host and non-host genes in plant systems. The construction of cDNA libraries within virus expression allows gene function to be assessed by screening plant hosts for phenotypic changes and gain of function effects measured by various input and output focused screening. The ability of virus vectors to effectively reprogram host machinery to favor expression of virally encoded genes has been used to overexpress genes of pharmaceutical relevance in plants. This capacity has moved from being a mere laboratory curiosity, to being exploited at greenhouse and field scale to produce products used in human clinical trials. These expression systems have primarily exploited dicot hosts, especially in the families of Solanaceae and Crucifereace. However, one report has been published for a potyvirus expression vector in monocot plants. This vector will allow the insertion of precise ORFs within the virus polyprotein for the accumulation of only cytosolically localized proteins (Choi, et al., 2000). This type of vector is limited in that only exact insertions are possible in this vector and not allowing insertion of crude cDNAs or libraries. It is further limited by not allowing the expression of secreted proteins in plants.

Continued research on virus expression vectors soon revealed new utilities. It has been extensively demonstrated that virus vectors are efficient tools to induce post-transcriptional gene silencing systemically in host plants. However, these effects have only been demonstrated in dicot hosts, primarily in *Nicotiana benthamiana* and *Arabidopsis thaliana*. The power of shuttling in plant gene sequences systemically into plants and screening infected plants for loss of function effects is a unique tool to determine function of endogenes. To confirm the effects of loss of function or gain of function events discovered in dicot plants, the ability to either express genes or silence them in monocot system would provide a powerful tool to confirm gene function in a second system. However, at present, no such tool exists. It is the purpose of this disclosure to describe the invention and reduction to practice of a monocot gene expression and gene silencing system.

Gopinath, et al. (2000) discloses a cowpea mosaic virus expressing a movement protein-green fluorescent protein ("GFP")-large coat protein fusion protein, with the foot and mouth disease virus 2A catalytic peptide at each side of the GFP insert. However, expression of the fusion protein is only demonstrated in a cowpea plant, which is a dicot plant.

WO99/36516 disclose the use of viral vectors to silence endogenous genes in a host, through post-transcription gene silencing of the endogenous host gene homolog, by introducing nucleic acids into the host by way of constructs based on tobacco mosaic virus or tomato mosaic virus.

Vectors for the genetic manipulation of plants have been derived from several naturally occurring plant viruses, including barley stripe mosaic virus ("BSMV"). BSMV is a tripartite RNA virus (Palomar, et al., 1977) (FIG. 1A) that infects many agriculturally important monocot species such as oat, wheat and barley (McKinney and Greeley, 1965). We developed several monocot viral vectors based on the BSMV genome that direct the expression of nucleotide sequences in transfected protoplasts and plants.

SUMMARY OF THE INVENTION

The present invention is directed to recombinant viruses comprising a viral genome or one or more recombinant viral vectors, each further comprising a polynucleotide encoding a fusion protein or a foreign protein of interest or a targeting nucleotide sequence capable of silencing a gene of interest. The present invention is also directed to a host comprising the recombinant virus, recombinant viral vector, or polynucleotide. The present is also directed to methods of expressing the fusion protein or a foreign protein, or silencing a gene of interest in a host.

(A) One aspect of the present invention is directed to one or more polynucleotide(s), wherein at least one of the one or more polynucleotide encodes a promoter operatively linked to a transcriptional unit, wherein the transcriptional unit encodes a fusion protein, wherein the fusion protein comprises (1) a viral protein, (2) a protein of interest, and (3) autoproteolytic peptide, wherein the autoproteolytic peptide is fused between the viral protein and the protein of interest. In one embodiment, the protein of interest is able to be directed to a specific location within the host cell.

(B) Another aspect of the present invention is also directed to one or more polynucleotide(s), wherein at least one of the one or more polynucleotide(s) encodes a promoter operatively linked to a transcriptional unit, wherein the transcriptional unit encodes a protein of interest, wherein the one or more polynucleotide(s) constitute a viral genome, wherein the gene, or fragment thereof, encoding a coat protein of the viral genome is deleted or mutated, wherein the coat protein is native to the viral genome. The deletion or mutation of the coat protein gene, or fragment thereof, causes an increased, elevated, enhanced, or high expression of the transcription unit when compared to a identical one or more polynucleotide(s) that does not have the deletion or mutation of the coat protein gene, or fragment thereof.

(C) Another aspect of the present invention is also directed to one or more polynucleotide(s), wherein at least one of the one or more polynucleotide(s) encodes a promoter operatively linked to a transcriptional unit, wherein the transcriptional unit encodes a protein of interest, wherein said polynucleotide is a duplicated genomic nucleic acid component. In one embodiment of the invention, there is only one duplicated genomic nucleic acid component.

(D) Another aspect of the present invention is also directed to one or more polynucleotide(s), wherein at least one of the one or more polynucleotide(s) encodes a promoter operatively linked to a transcriptional unit, wherein the transcriptional unit encodes a viral protein, a stop codon, and a targeting nucleotide sequence, wherein the a viral protein is 5' of the stop codon, and the stop codon is 5' of the targeting nucleotide sequence, wherein the viral protein, the stop codon, and the targeting nucleotide sequence are transcribed as a transcriptional unit, wherein the targeting nucleotide sequence is substantially homologous to a gene of interest, or fragment thereof, to be silenced. The target nucleotide sequence can be in the sense or antisense orientation of the gene of interest to be silenced. Preferably the target nucleotide sequence is in the sense orientation. Preferably silencing takes place in the cytoplasm.

BRIEF DESCRIPTION OF THE FIGURES

FIG. 1A depicts the genetic structure of the BSMV γ42 clone.

FIG. 1C depicts the genetic structure of four RNAγ constructs: "γ.γb.stop.P/N-zeo-B", "γ.γb.stop.N/P-zeo-B", "γ.γb.stop.P/N-zeo-S", and γ.γb.stop.N/P-zeo-S" (including the restriction sites for NheI, PacI, NotI, BssHII, and SwaI).

Figure 1B:
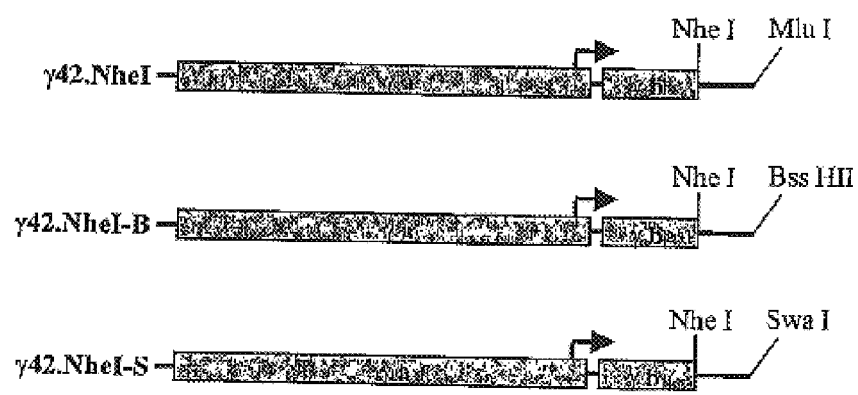
FIG. 1B depicts the genetic structure of three RNAγ constructs: "γ42.NheI", "γ42.NheI-Bγ", and "γ42.NheI-S" (including the restriction sites for NheI, MluI, BssHII, and SwaI).

The autoproteolytic peptide is any amino acid sequence that can essentially independently cleave itself by breaking a peptide bond or covalent bond with its sequence in the presence of heterologous amino acid sequences at both its N-and C-terminal ends. An example of an amino acid sequence that essentially contains an autoproteolytic cleavage activity is the 2A peptide of the foot and mouth disease virus ("FMDV"). Examples of these are: NFDLLKLAGDVESNPGP (SEQ ID NO: 1) (Mattion et al., *J. Virol.* 70(11): 8124–7 (1996)), QLLNFDLLKLAGDVESNLGP (SEQ ID NO: 2) (FMD-A10), QLLNFDLLKLAGDVESNPRP (SEQ ID NO: 3) (FMD-A12), QLLNFDLLKLAGDVESNPGP (SEQ ID NO: 4) (FMD-C1), QTLNFDLLKLAGDVESNPGP (SEQ ID NO: 5) (FMD-O1k), QLLNFDLLKLAGDVESNPGP (SEQ ID NO: 6) (FMD-Sat2), HYAGYFADLLIHDIETNPGP (SEQ ID NO: 7) (EMC-R), HYAGYFSDLLIHDVETNPGP (SEQ ID NO: 8) (Mengo), YHADYYKQRLIHDVEMNPGP (SEQ ID NO: 9) (TMEDA) (Palmenberg, 1990).

The 2A peptide cleavage occurs at the C-terminal end of the glycine-proline amino acid pair. For example, the autoproteolytic peptide QLLNFDLLKLAGDVESNPGP (SEQ ID NO: 6) is cleaved into two separate portions: QLLNFDLLKLAGDVESNPG (SEQ ID NO: 10) and a proline. The former portion is attached to the C-terminus of whatever peptide was attached to the N-terminus of the autoproteolytic peptide, and the proline is attached to the N-terminus of whatever peptide was attached to the C-terminus of the autoproteolytic peptide. The autoproteolytic peptide may be cleaved prior to the complete translation of the ORF encoding the entire fusion protein. The autoproteolytic peptide preferably contains no more than twenty amino acid residues. More preferably, the autoproteolytic peptide contains no more than seventeen amino acid residues. The autoproteolytic peptide preferably after cleavage does not leave sufficient residual amino acid residues attached to the viral protein that will interfere with the biochemical or biological activity or fuiction of the viral protein, especially in the ability of the virus to replicate, assemble, move from cell to cell, achieve systemic infection, etc. The autoproteolytic peptide preferably after cleavage does not leave sufficient residual amino acid residues attached to protein of interest that will interfere with the biochemical or biological activity or function of the protein of interest in its effect on the host or purification or any characteristic of the protein of interest that is of interest to the practitioner of the invention. In a preferred embodiment the peptide that is subject to cleavage is the 2A peptide, or a fragment thereof that essentially contains an autoproteolytic cleavage activity, of a FMDV. The autoproteolytic peptide may be linked to the N-or C-terminal end of the viral protein. If the autoproteolytic peptide is linked to the N-terminal end of the viral protein, then the protein of interest is linked to the N-terminal end of the autoproteolytic peptide. If the autoproteolytic peptide is linked to the C-terminal end of the viral protein, then the protein of interest is linked to the C-terminal end of the autoproteolytic peptide. These links may comprise a covalent bond such as a peptide bond. One of ordinary skill in the art is able to construct a fusion protein comprising an autoproteolytic peptide (DeFelipe, et al., 2000; Gopinath, et al., 2000; Kokuho, et al., 1999; DeFilipe, et al., 1999; Chaplin, et al., 1999; Halpin, et al., 1999; Donnelly, et al., 1997; Mattion, et al., 1996; Li, et al., 1996; Ryan, et al., 1994; Ryan, et al., 1991).

The promoter is operatively linked to the transcriptional unit so that the transcriptional unit is capable of being expressed in the host. The promoter is linked 5' to transcriptional unit. Any native or non-native promoter may be used. The promoter may also be native or non-native to the viral protein. The expression of the transcriptional unit may be driven by any of a variety of promoters functional in the genome of the recombinant virus in the host. The transcriptional unit may also be expressed by any promoter functional in a host, that is a plant or a plant cell, 5' to the transcriptional unit. In a preferred embodiment, the host is a plant cell, a plant protoplast, a cell in a plant cell culture, or any appropriate cell. The promoter may be any viral promoter or RNA viral promoter or viral subgenomic promoter. In a preferred embodiment, the promoter is any promoter of a RNA plant virus. In a more preferred embodiment, the promoter is any promoter of a single-stranded plus-sense RNA plant virus. In an even more preferred embodiment, the promoter is any promoter of a multipartite single-stranded plus-sense RNA plant virus. In an even further more preferred embodiment, the promoter is any promoter of a tripartite single-stranded plus-sense RNA plant virus, such as a hordeivirus. In an even much further more preferred embodiment, the promoter is any promoter of BSMV, such as the promoters of the βb or γb gene. In another preferred embodiment of the invention, the fusion proteins are expressed from plant viral subgenomic promoters using vectors as described in U.S. Pat. No. 5,316,931. The promoter need not be a naturally occurring promoter but can also be a synthetic promoter designed to initiate transcription of the transcriptional unit in a host. The expression of the fusion protein may be elevated or controlled by a variety of plant or viral transcription factors. In addition, there is no need to use a promoter that is an additional subgenomic promoter.

The promoter may also be a plant promoter. The plant promoter may be a tissue-or developmentally-regulated and/ or an inducible promoter. Inducible promoters may be advantageous in certain circumstances because they place the timing of expression of the transcriptional unit under the control of the user. The term "inducible" as applied to a promoter is well understood by those of ordinary skill in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic or biochemical change. Thus an inducible (or "switchable") promoter may be used which causes a basic level of expression in the absence of the stimulus which level is too low to bring about a desired phenotype (and may in fact be zero). Upon application of the stimulus, expression is increased (or "switched on") to a level which brings about the desired phenotypic or biochemical change.

The expression of the transcriptional unit, fusion protein, protein of interest, or viral protein of the subject invention can take place in vitro, in vivo, or in the cytoplasm of the host. The targeting nucleotide sequence comprises a nucleotide sequence that is identical or complementary to a gene of interest to be silenced, either in the sense or antisense orientation, or a sequence which has sufficient homology to a gene of interest to be silenced for down-regulation of the expression of the target sequence to occur. The targeting nucleotide sequence in its entirety may or may not encode an ORF. The targeting nucleotide sequence may have the identical or complementary sequence of the gene of interest to be silenced. The targeting nucleotide sequence may be able to silence one or more genes; in this case, there is more than one gene of interest to be silenced.

The gene of interest to be silenced can be any gene found in the host. The gene of interest may code for a rRNA, tRNA, ribozyme, or any peptide or protein. The targeting nucleotide sequence can be a stretch of nucleotides of any length as long the length or sequence does not interfere with the expression of the transcriptional unit or the silencing of the gene of interest. The targeting nucleotide sequence can be as short as 200 nucleotides. The targeting nucleotide sequence may contain the ORF of one gene of organism, and be able silence the gene of that organism, and/or one or more different gene(s) of that organism, and/or one or more different gene(s) of one or more different organism(s). For example, a targeting nucleotide sequence comprising a fragment of the ORF of phytoene desaturase (PDS) of rice (*Oryza sativa*) or corn (*Zea mays*), when expressed in barley, silences the expression of PDS of barley (see Example 9). The targeting nucleotide sequence is not able to be translated from the transcriptional unit. This is because there is one or more stop codon(s) adjacent 5' to or immediately preceding the region of sequence encoding the protein, or fragment thereof. The targeting nucleotide sequence, if containing one or more ORF(s), need not be in frame with any translatable regions of nucleotide sequence 5' of the targeting nucleotide sequence. The transcriptional unit may comprise a plurality of one targeting nucleotide sequence, different targeting nucleotide sequences, or a combination of the same or different targeting nucleotide sequences. Different targeting nucleotide sequence may silence the same gene of interest to be silenced. One targeting nucleotide sequence may silence a plurality of genes of interest to be silenced. There may be one gene of interest to be silenced in a host, or there may be a plurality of genes of interest to be silenced in a host.

The term "silence" or "silenced" denotes a lowered or decreased expression of a gene. Any degree of lowering or decreasing of the expression of a gene is sufficient to constitute the gene to be silenced. The degree of lowering or decreasing of the expression of a gene may be of a degree sufficient to detect a phenotypic or biochemical of a host comprising the gene. The gene to be silenced may only be expressed in a host temporally or spatially within an organism, in such cases silencing would only occur when the gene to be silenced in the host at a time and/or place when the gene would have been expressed. The user of the invention may cause silencing to take place only in a temporal-and/or spatially-specific manner. Within each host cell, silencing preferably takes place within the cytoplasm. More preferably, silencing takes place in the cytoplasm of a plant cell. Even more preferably, silencing takes place in the cytoplasm of a monocot plant cell.

Silencing one or more gene(s) of interest may produce one or more results desirable to a user. For example, it may be desirable to silence a gene in a commercial fruit or vegetable that causes faster ripening in order to improve the shelf life of the fruit or vegetable. For example, it may be desirable to silence a gene in a commercial fruit or vegetable that causes faster ripening in order to improve processing and handling characteristics of the fruit or vegetable and to lengthen the shelf life of the fruit or vegetable. For example, it may be desirable to silence a gene involved in pollen formation of a commercial plant in order to that breeders can reproducibly generate male sterile plants for the production of FI hybrids. For example, it may be desirable to silence a gene involved in lignin formation in order to facilitate paper manufacturing from vegetative tissues of the plant. For example, it may be desirable to silence a gene involved in pigment production in order to produce novel color or color patterns of flowers of ornamental plants. For example, it may be desirable to silence a gene involved in regulatory pathways controlling development or environmental responses to produce plants with novel growth habit or disease/pest resistance. For example, it may be desirable to silence a gene involved in production of toxins in order to eliminate the production of toxic secondary metabolites. For example, it may be desirable to silence a gene encoding an enzyme in a metabolic pathway of a commercial fruit or vegetable plant in order to cause an increase of the level of an intermediate metabolic product in the fruit or vegetable.

The one or more polynucleotide(s) of the present invention can be part of a recombinant virus. The recombinant virus may be a DNA or RNA virus. The recombinant virus can be derived from a plant virus. In a preferred embodiment, the virus is a RNA plant virus. In a more preferred embodiment, the virus is a single-stranded plus-sense RNA plant virus. In an even more preferred embodiment, the virus is a multipartite single-stranded plus-sense RNA plant virus. In an even further more preferred embodiment, the virus is a tripartite single-stranded plus-sense RNA plant virus, such as a hordeivirus. In an even much further more preferred embodiment, the virus is a BSMV. Preferred viruses have the following characteristics: (a) ability to generate a high level of transcription of the ORF encoding the fusion protein in the host, (b) ability to tolerate the ORFs of the fusion protein in the life cycle of the virus, including replication, assembly, viral movement, systemic infection, etc., (c) the promoter must be able to tolerate the expression of fusion protein(s), and, (d) the viral genome only has to stay in the cytoplasm of the host, i.e., the viral genome neither has to be present in the nucleus nor integrated in a host chromosome. The one or more polynucleotide(s) of the present invention, when assembled as a recombinant virus, are preferably still infectious and/or capable of systemic infection.

The construction of recombinant viruses or recombinant viral vectors may use a variety of methods known in the art. In preferred embodiments of the instant invention, the recombinant viruses and recombinant viral vectors are derived from RNA plant viruses. A variety of plant virus families may be used, such as Bromoviridae, Bunyaviridae, Comoviridae, Geminiviridae, Potyviridae, and Tombusviridae, among others. Within the plant virus families, various genera of viruses may be suitable for the instant invention, such as alfamovirus, ilarvirus, bromovirus, cucumovirus, tospovirus, carlavirus, caulimovirus, closterovirus, comovirus, nepovirus, dianthovirus, furovirus, hordeivirus, luteovirus, necrovirus, potexvirus, potyvirus, rymovirus, bymovirus, oryzavirus, sobemovirus, tobamovirus, tobravirus, carmovirus, tombusvirus, tymovirus, umbravirusa, and among others.

Within the genera of plant viruses, many species are particular preferred. They include alfalfa mosaic virus, tobacco streak virus, brome mosaic virus, broad bean mottle virus, cowpea chlorotic mottle virus, cucumber mosaic virus, tomato spotted wilt virus, carnation latent virus, cauliflower mosaic virus, beet yellows virus, cowpea mosaic virus, tobacco ringspot virus, carnation ringspot virus, soil-borne wheat mosaic virus, tomato golden mosaic virus, cassava latent virus, barley stripe mosaic virus, barley yellow dwarf virus, tobacco necrosis virus, tobacco etch virus, potato virus X, potato virus Y, rice necrosis virus, ryegrass mosaic virus, barley yellow mosaic virus, rice ragged stunt virus, Southern bean mosaic virus, tobacco mosaic virus, ribgrass mosaic virus, cucumber green mottle mosaic virus watermelon strain, oat mosaic virus, tobacco rattle virus, carnation mottle virus, tomato bushy stunt virus, turnip yellow mosaic virus, carrot mottle virus, among others. In addition, RNA satellite viruses, such as tobacco necrosis satellite may also be employed.

A given plant virus may contain either DNA or RNA, which may be either single-or double-stranded. One example of plant viruses containing double-stranded DNA includes, but not limited to, caulimoviruses such as cauliflower mosaic virus (CaMV). Representative plant viruses that contain single-stranded DNA are cassava latent virus, bean golden mosaic virus (BGMV), and chloris striate mosaic virus. Rice dwarf virus and wound tumor virus are examples of double-stranded RNA plant viruses. Single-stranded RNA plant viruses include tobacco mosaic virus (TMV), turnip yellow mosaic virus (TYMV), rice necrosis virus (RNV), brome mosaic virus (BMV), and BSMV. The single-stranded RNA viruses can be further divided into plus-sense (or positive-stranded), minus-sense (or negative-stranded), or ambisense viruses. The genomic RNA of a plus sense RNA virus is messenger sense, which makes the naked RNA infectious. Many plant viruses belong to the family of plus sense RNA viruses. They include, for example, TMV, BMV, and others. RNA plant viruses typically encode several common proteins, such as replicase/polymerase proteins essential for viral replication and MRNA synthesis, coat proteins providing protective shells for the extracellular passage, and other proteins required for the cell-to-cell movement, systemic infection and self-assembly of viruses. The plant virus may also comprises a genome of only one nucleic acid or a bipartite, tripartite or multipartite genome. For general information concerning plant viruses, see Matthews, *Plant Virology*, 3$^{rd}$ Ed., Academic Press, San Diego (1991).

Selected groups of suitable plant viruses are characterized below. However, the invention should not be construed as limited to using these particular viruses, but rather the method of the present invention is contemplated to include all plant viruses at a minimum. However, the invention should not be construed as limited to using these particular viruses, but rather the present invention is contemplated to include all suitable viruses. Some suitable viruses are characterized below.

Tobamovirus Group

The tobacco mosaic virus (TMV) is able to express genes at high levels in plants. TMV is a member of the tobamovirus group. The TMV virion is a tubular filament, and comprises coat protein sub-units arranged in a single right-handed helix with the single-stranded RNA intercalated between the turns of the helix. TMV infects tobacco as well as other plants. TMV virions are 300 nm×18 nm tubes with a 4 nm-diameter hollow canal, and consist of 2140 units of a single structural protein helically wound around a single RNA molecule. The genome is a 6395 base plus-sense RNA. The 5'-end is capped and the 3'-end contains a series of pseudoknots and a tRNA-like structure that will specifically accept histidine. The genomic RNA functions as MRNA for the production of proteins involved in viral replication: a 126-kDa protein that initiates 68 nucleotides from the 5'-terminus, and a 183-kDa protein synthesized by readthrough of an amber termination codon approximately 10% of the time. Only the 183-kDa and 126-kDa viral proteins are required for the TMV replication in trans. (Ogawa et al., *Virol.* 185:580–584 (1991)). Additional proteins are translated from subgenomic size mRNA produced during replication (Dawson, *Adv. Virus Res.,* 38:307–342 (1990)). The 30-kDa protein is required for cell-to-cell movement; the 17.5-kDa capsid protein is the single viral structural protein. The function of the predicted 54-kDa protein is unknown.

TMV assembly apparently occurs in plant cell cytoplasm, although it has been suggested that some TMV assembly may occur in chloroplasts since transcripts of ctDNA have been detected in purified TMV virions. Initiation of TMV assembly occurs by interaction between ring-shaped aggregates ("discs") of coat protein (each disc consisting of two layers of 17 subunits) and a unique internal nucleation site in the RNA; a hairpin region about 900 nucleotides from the 3'-end in the common strain of TMV. Any RNA, including subgenomic RNAs containing this site, may be packaged into virions. The discs apparently assume a helical form on interaction with the RNA, and assembly (elongation) then proceeds in both directions (but much more rapidly in the 3'- to 5'- direction from the nucleation site).

Another member of the Tobamoviruses, the Cucumber Green Mottle Mosaic virus watermelon strain (CGMMV-W) is related to the cucumber virus. Nozu et al., *Virol.* 45:577 (1971). The coat protein of CGMMV-W interacts with RNA of both TMV and CGMMV to assemble viral particles in vitro. Kurisu et al., *Virol.* 70:214 (1976).

Several strains of the tobamovirus group are divided into two subgroups, on the basis of the location of the assembly of origin. Subgroup I, which includes the vulgare, OM, and tomato strain, has an origin of assembly about 800–1000 nucleotides from the 3'-end of the RNA genome, and outside the coat protein cistron. Lebeurier et al., *Proc. Natl. Acad. Sci. USA* 74:149 (1977); and Fukuda et al., *Virology* 101:493 (1980). Subgroup II, which includes CGMMV-W and compea strain (Cc) has an origin of assembly about 300–500 nucleotides from the 3'-end of the RNA genome and within the coat-protein cistron. The coat protein cistron of CGMMV-W is located at nucleotides 176–661 from the 3'-end. The 3' noncoding region is 175 nucleotides long. The origin of assembly is positioned within the coat protein cistron. Meshi et al., *Virology* 127:54 (1983).

Brome Mosaic Virus Group

Brome Mosaic virus (BMV) is a member of a group of tripartite, single-stranded, RNA-containing plant viruses commonly referred to as the bromoviruses. Each member of the bromoviruses infects a narrow range of plants. Mechanical transmission of bromoviruses occurs readily, and some members are transmitted by beetles. In addition to BV, other bromoviruses include broad bean mottle virus and cowpea chlorotic mottle virus.

Typically, a bromovirus virion is icosahedral, with a diameter of about 26 $\mu$m, containing a single species of coat protein. The bromovirus genome has three molecules of linear, positive-sense, single-stranded RNA, and the coat protein mRNA is also encapsidated. The RNAs each have a capped 5'-end, and a tRNA-like structure (which accepts tyrosine) at the 3'-end. Virus assembly occurs in the cytoplasm. The complete nucleotide sequence of BMV has been identified and characterized as described by Ahlquist et al., *J. Mol. Biol.* 153:23 (1981).

Rice Necrosis Virus

Rice Necrosis virus is a member of the Potato Virus Y Group or Potyviruses. The Rice Necrosis virion is a flexuous filament comprising one type of coat protein (molecular weight about 32,000 to about 36,000) and one molecule of linear positive-sense single-stranded RNA. The Rice Necrosis virus is transmitted by *Polymyxa oraminis* (a eukaryotic intracellular parasite found in plants, algae and fungi).

Geminiviruses

Geminiviruses are a group of small, single-stranded DNA-containing plant viruses with virions of unique morphology. Each virion consists of a pair of isometric particles (incomplete icosahedral), composed of a single type of protein (with a molecular weight of about $2.7-3.4\times10^4$). Each geminivirus virion contains one molecule of circular, positive-sense, single-stranded DNA. In some geminiviruses (i.e., Cassava latent virus and bean golden mosaic virus) the genome appears to be bipartite, containing two single-stranded DNA molecules.

Potyviruses

Potyviruses are a group of plant viruses which produce polyprotein. A particularly preferred potyvirus is tobacco etch virus (TEV). TEV is a well characterized potyvirus and contains a positive-strand RNA genome of 9.5 kilobases encoding for a single, large polyprotein that is processed by three virus-specific proteinases. The nuclear inclusion protein "a" proteinase is involved in the maturation of several replication-associated proteins and capsid protein. The helper component-proteinase (HC-Pro) and 35-kDa proteinase both catalyze cleavage only at their respective C-termini. The proteolytic domain in each of these proteins is located near the C-terminus. The 35-kDa proteinase and HC-Pro derive from the N-terminal region of the TEV polyprotein.

Hordeivirus Group

Hordeiviruses are a group of single-stranded, positive sense RNA-containing plant viruses with three or four part genomes. Hordeiviruses have rigid, rod-shaped virions. Hordeivirus is composed of four members: barley stripe mosaic virus ("BSMV"), poa semilatent virus ("PSLV"), lychnis ringspot virus ("LRSV"), and anthoxanthum latent blanching virus ("ALBV") (Jackson, et al., 1989). BSMV is the type member of this group of viruses. BSMV infects a large number of monocot and dicot species including barley, oat, wheat, corn, rice,, spinach, and *Nicotiana benthamiana*. Local lesion hosts include *Chenopodium amaranticolor*, and *Nicotiana tabacum* ccv. Samsun. BSMV is not vector transmitted but is mechanically transmissable and in some hosts, such as barley, is also transmitted through pollen and seed.

Most strains of BSMV have three genomic RNAs referred to as RNAα (or αRNA), RNAβ (or βRNA), and RNAγ (or γRNA). At least one strain, the Argentina mild (AM) strain has a fourth genomic RNA that is essentially a deletion mutant of the RNAγ. All genomic RNAs are capped at the 5' end and have tRNA-like structures at the 3' end. Virus replication and assembly occurs in the cytoplasm. The complete nucleotide sequence of several strains of BSMV has been identified and characterized (reviewed by Jackson, et al., 1989), and infectious cDNA clones are available (Petty, et al. *Virol.* 171:342–349 (1989)).

BSMV is a plus-sense single-stranded RNA virus that is able to infect plants of the Chenopodiaceae, Gramineae, and Solanaceae families, including, but not limited to, the following species: *Anthoxanthum aristatum, Anthoxanthum odoratum, Avena sativa, Beta vulgaris, Bromus secalinus, Bromus tectorum, Chenopodium album, Chenopodium amaranticolor, Chenopodium quinoa, Dactylis glomerata, Echinochloa crus-galli, Elytrigia intermedia, Eragrostis cilianensis, Festuca pratensis, Hordeum vulgare, Lagurus ovatus, Lolium multiflorum, Lolium perenne, Lolium persicum, Lolium temulentum, Lophopyrum elongatum, Nicotiana tabacum, Oryza sativa, Oryzopsis miliacea, Panicum capillare, Panicum miliaceum, Phalaris arundinacea, Phalaris paradoxa, Phleum arenarium, Phleum pratense, Poa annua, Poa pratensis, Secale cereale, Setaria italica, Setaria macrostachya, Setaria viridis, Sorghum bicolor, Spinacia oleracea, Triticum aestivum, Triticum durum*, and *Zea mays*. The natural host range is *H. vulgare* and *T. aestivum*. The method of transmission does not involve a vector and is by mechanical inoculation by seed (up to 90–100%) and by pollen to the pollinated plant. The morphology of the BSMV virions are rod-shaped, not enveloped, usually straight, with a clear modal length, of 112–150 nm, 18–24 nm wide, with an obvious axial canal (3–4 nm in diameter), and with a basic helix wiht a pitch of 2.5–2.6 nm. (Brunt et al., 1996).

The BSMV virion contains 3.8–4% nucleic acid, 96% protein, and 0% lipid by weight. The BSMV genome consists of three single-stranded linear RNA (designated RNAα, RNAβ, and RNAγ). The total genome size is 10.289 kb (Brunt et al., 1996). Each genomic RNA has a 7-methylguanosine cap at its 5' terminus and contains the initial sequence $m^7$ GpppGUA, and has a highly conserved 3' terminus that has a polyadenylate (poly A) sequence that separates the coding region of each RNA from a 238 nucleotide 3' terminal tRNA-like structure that can be aminoacylated with tyrosine. BSMV encodes a total of seven polypeptides. RNAα encodes αa, a 130 kDa protein which is believed to be an integral component of viral replicase. αa has a putative methyltransferase domain near the N-terminus and a nucleotide binding motif near the C-terminus (Jackson et al., 1991). When cca of BSMV strain N18 (non-pathogenic to oat) had more than half of its ORF replaced with the homologous αa of BSMV strain CV42 (pathogenic to oat), the gene homologous gene replacement enabled strain N18 to infect oat. In addition, a single amino acid substitution or up to six single amino acid substitutions (including the substitution of two adjacent amino acids) in oca of strain N18 enabled strain N18 to infect oat (Weiland et al., 1996). RNAβ encodes four polypeptides: βa, the 22 kDa coat protein; βb, a 60 kDa disease-specific protein, which contains a nucleotide binding motif similar to αa; βc, a 17 kDa protein of unknown function but which is required for infectivity in barley (*N. benthamiana* and *C. amaranticolor*); and, βd, a 14 kDa protein essential for systemic infection and associated with the membrane fraction of infected barley. The ORFs of βb, βc and βd are tightly organized to form a triple gene block ("TGB") whereby βd overlaps βb and βc. The TGB is similar in organization to the overlapping gene blocks found in furoviruses, potexviruses, and potato virus M, a carlavirus (Jackson et al., 1991). RNAγ encodes two ORFs: γa and γb. The γa ORF encodes a second replicase component, γa, that contains the GDD polymerase motif that is universally present in the replicases of plus-sense RNA viruses. The γb ORF encodes a 17 kDa cysteine rich protein, γb, contains a cysteine-rich region. BSMV with mutations which introduce single or up to four single amino acid substitutions in γb, when used to inoculate barley plants, resulted in altered symptom phenotype (Donald et al., 1994). BSMV is of interest to provide new and improved vectors for the genetic manipulation of plants.

Genomic RNAα serves as an MRNA for the expression of the βa protein. Genomic RNAβ only serves as an MRNA for the expression of the βa protein. RNAβ gives rise to two subgenomic ("sg") RNA-β mRNA: sgRNAβ1 and sgRNAβ2, which have transcription initiation sites at nucleotides 789 and 2327, respectively, of RNA-β. sgRNAβ1 directs translation of the βb protein, while sgRNAβ2 translates the βc and βd proteins and a 23 kDa protein (designated βd') which is a readthrough product of the amber stop codon of the βd ORF (Zhou et al., 1996). In the presence of both RNAα and RNAγ, RNAβ containing gene replacements of either βa or βb with the firefly luciferase (luc) gene mediate expression of the luc gene upon transfection into tobacco leaf mesophyll and maize protoplasts (Joshi et al., 1998). In-frame insertions of the chloramphenicol acetyl transferase ("CAT") reporter gene in the βb, βc, βd, and βd' ORFs of RNA-β, when coinoculated into barley cultivar protoplasts with RNA-α and RNA-γ, resulted in the expression of active CAT from insertions in βb, βc, βd, and βd'(Zhou et al., 1996).

The coat protein may be encoded on a polynucleotide that is distinct from the polynucleotide encoding the protein of interest. The coat protein may be encoded on a subgenomic RNA that is distinct from the subgenomic RNA encoding the protein of interest. In a preferred embodiment the viral genome is the genome of a hordeivirus, and the coat protein is encoded on RNAβ that is distinct from RNAα or RNAγ encoding the protein of interest.

The non-expression of the coat protein is the total absence of the coat protein (e.g. caused by the deletion of the coat protein gene) or a decrease of the expression of the coat protein, as compared to a wild-type virus, or the expression of a mutant form of coat protein, or a combination of any of the above phenomenon. The non-expression of the coat protein may be brought about by deleting the coat protein gene, or by deleting a fragment of the coat protein gene whereby sufficient sequence essential to cause to increase expression from the promoter. The sequences important for causing the increased expression of the protein of interest can be easily determined by one of ordinary skill in the art by creating a series of nested deletions of the coat protein gene and testing to determine whether the expression of the protein of interest is increased.

The basis by which the deletion or mutation of the coat protein, or fragment thereof, causes an increased expression of the protein of interest may be due to the competition of the coat protein with the polynucleotide encoding the protein of interest for one or more factor or for access to the translation machinery. Another basis may be that the regulation of the promoter operatively linked to the transcription unit may be regulated or modulated by the presence or absence of the coat protein either directly or indirectly. Another further basis may be that certain nucleic acid region(s) of the coat protein regulates or modulates the expression of the promoter operatively linked to the transcription unit either directly or indirectly. That the non-expression of the coat protein causes an increased expression of the transcription unit may be due to any combination of the reasons cited above.

The duplicated genomic nucleic component may be a subgenomic RNA. The duplicated genomic nucleic component may be a duplicated subgenomic RNA of a multipartite virus. The promoters of all the duplicated genomic nucleic acid components may be identical or different to each other.

The ORFs of all the duplicated genomic nucleic acid components can be identical or different to each other.

There can be one or more duplicated genomic nucleic acid components. The viral genome may further comprise additional duplicated genomic nucleic acid component(s), wherein each of the additional duplicated genomic nucleic acid component encodes an transcriptional unit operatively linked to a promoter, wherein each transcriptional unit may be non-identical to the transcriptional unit (s) of the other duplicated genomic nucleic acid component(s), wherein each promoter may be non-identical to the promoter(s) of the other duplicated genomic nucleic acid component(s). If the viral genome is the genome of a hordeivirus, such as a BSMV, the duplicated genomic nucleic acid component is preferably duplicated RNAγ. If the viral genome is the genome of a BSMV, the promoter is preferably the promoter of the γb gene.

If the duplicated genomic nucleic acid and component is a duplicated subgenomic RNA of a hordeivirus, such as a BSMV, the viral genome plus any duplicated subgenomic RNA can be packaged into a recombinant virus, or recombinant viral particle using the Argentina Mild strain of BSMV.

The present invention is also directed to compositions and methods for decreasing the expression of a plant gene (or a gene of interest to be silenced or a target gene) in order to bring about a desired phenotypic or biochemical change of a plant host. The present invention is also directed to a method of changing the phenotype or biochemistry of a plant host, a method of determining a change in phenotype or biochemistry in a plant host, a method of determining the presence of a trait in a plant host, and a method of determining the function of a nucleic acid sequence. The method comprise the steps of expressing permanently or transiently a nucleic acid sequence in a sense or antisense orientation in a plant host, identifying changes in the plant host and correlating the expression and the changes.

The present invention provides a method of infecting a plant host by a recombinant plant viral nucleic acid with contains one or more non-native nucleic acid sequences, or by a recombinant plant virus containing a recombinant plant nucleic acid. The non-native nucleic acids are subsequently transcribed or expressed in the infected host plant. The products of the non-native nucleic acid sequences result in changing phenotypic traits in the plant host, affecting biochemical pathways within the plant, or affecting endogenous expression within the plant.

The invention provides for recombinant plant viruses comprising a recombinant viral vector capable of decreasing the expression of a plant gene. The decreasing of the expression of a plant gene may take place in a host. The recombinant plant viruses or recombinant viral vectors may infect a single host cell or systemically infect a plant. Thus by employing the recombinant plant viruses or recombinant viral vectors of the invention, by decreasing or totally shutting down the expression of one or more plant genes the phenotype or one or more characteristic of a plant may be altered. The present invention also provides for methods involving the use of such recombinant plant viruses and recombinant viral vector which bring about the decreased expression of a plant gene or the altering of the phenotype or one or more characteristic of a plant.

The stop codon, also known as a terminating or termination codon, may be TAA, TAG, or TGA, as read in DNA from 5'to 3', or UAA, UAG, or UGA, as read in RNA from 5' to 3'.

The selection of the genetic backbone for the viral vectors of the instant invention may depend on the plant host used.

The plant host may be a monocotyledonous or dicotyledonous plant, plant tissue, or plant cell. Typically, plants of commercial interest, such as food crops, seed crops, oil crops, ornamental crops and forestry crops are preferred. For example, wheat, rice, corn, potato, barley, tobacco, soybean canola, maize, oilseed rape, lilies, grasses, orchids, irises, onions, palms, tomato, the legumes, or Arabidopsis, can be used as a plant host. Host plants may also include those readily infected by an infectious virus, such as Nicotiana, preferably, *Nicotiana benthamiana*, or *Nicotiana clevelandii*.

One feature of the present invention is the use of plant viral nucleic acids which comprise one or more non-native nucleic acid sequences capable of being transcribed in a plant host. These nucleic acid sequences may be native nucleic acid sequences that occur in a host plant. Preferably, these nucleic acid sequences are non-native nucleic acid sequences that do not normally occur in a host plant. For example, the plant viral vectors may contain sequences from more than one virus, including viruses from more than one taxonomic group. The plant viral nucleic acids may also contain sequences from non-viral sources, such as foreign genes, regulatory sequences, fragments thereof from bacteria, fungi, plants, animals or other sources. These foreign sequences may encode commercially useful proteins, polypeptides, or fusion products thereof, such as enzymes, antibodies, hormones, pharmaceuticals, vaccines, pigments, antimicrobial polypeptides, and the like. Or they may be sequences that regulate the transcription or translation of viral nucleic acids, package viral nucleic acid, and facilitate systemic infection in the host, among others.

In some embodiments of the instant invention, the plant viral vectors may comprise one or more additional native or non-native subgenomic promoters which are capable of transcribing or expressing adjacent nucleic acid sequences in the plant host. These non-native subgenomic promoters are inserted into the plant viral nucleic acids without destroying the biological function of the plant viral nucleic acids using known methods in the art. For example, the CaMV promoter can be used when plant cells are to be transfected. The subgenomic promoters are capable of functioning in the specific host plant. For example, if the host is tobacco, TMV, tomato mosaic virus, or other viruses containing at least one subgenomic promoter may be utilized. The inserted subgenomic promoters should be compatible with the TMV nucleic acid and capable of directing transcription or expression of adjacent nucleic acid sequences in tobacco. It is specifically contemplated that two or more heterologous non-native subgenomic promoters may be used. The non-native nucleic acid sequences may be transcribed or expressed in the host plant under the control of the subgenomic promoter to produce the products of the nucleic acids of interest.

In some embodiments of the instant invention, the recombinant plant viral nucleic acids may be further modified by conventional techniques to delete all or part of the native coat protein coding sequence or put the native coat protein coding sequence under the control of a non-native plant viral subgenomic promoter. If it is deleted or otherwise inactivated, a non-native coat protein coding sequence is inserted under control of one of the non-native subgenomic promoters, or optionally under control of the native coat protein gene subgenomic promoter. Thus, the recombinant plant viral nucleic acid contains a coat protein coding sequence, which may be native or a nonnative coat protein coding sequence, under control of one of the native or non-native subgenomic promoters. The native or non-native coat protein gene may be utilized in the recombinant plant viral nucleic acid. The non-native coat protein, as is the case for the native coat protein, may be capable of encapsidating the recombinant plant viral nucleic acid and providing for systemic spread of the recombinant plant viral nucleic acid in the host plant.

In some embodiments of the instant invention, nucleic sequences encoding reporter protein(s) or antibiotic/herbicide resistance gene(s) may be constructed as carrier protein(s) for the polypeptides of interest, which may facilitate the detection of polypeptides of interest. For example, green fluorescent protein (GFP) may be simultaneously expressed with polypeptides of interest. In another example, a reporter gene, β-glucuronidase (GUS) may be utilized. In another example, a drug resistance marker, such as a gene whose expression results in kanamycin resistance, may be used.

Since the RNA genome is typically the infective agent, the transcriptional unit is positioned adjacent a suitable promoter so that the RNA is produced in the production cell. The RNA is capped using conventional techniques, if the capped RNA is the infective agent. In addition, the capped RNA can be packaged in vitro with added coat protein from TMV to make assembled virions. These assembled virions can then be used to inoculate plants or plant tissues. Alternatively, an uncapped RNA may also be employed in the embodiments of the present invention. Contrary to the practiced art in scientific literature and in issued patent (Ahlquist et al., U.S. Pat. No. 5,466,788), uncapped transcripts for virus expression vectors are infective on both plants and in plant cells. Capping is not a prerequisite for establishing an infection of a virus expression vector in plants, although capping increases the efficiency of infection. In addition, nucleotides may be added between the transcription start site of the promoter and the start of the cDNA of a viral nucleic acid to construct an infectious viral vector. One or more nucleotides may be added. In some embodiments of the present invention, the inserted nucleotide sequence may contain a G at the 5'-end. Alternatively, the inserted nucleotide sequence may be GNN, GTN, or their multiples, $(GNN)_X$ or $(GTN)_X$.

The polynucleotides of the subject invention may be encoded in RNA or DNA or any synthetic nucleic acid, single- or double-stranded, linear or circular, capable of expression into RNA in a eukaryotic host, such as a yeast, such as Sacchromyces cerevisiae, or a prokaryotic host, such as a bacteria, as *Escherichia coli*. Depending on the desired host to be used the necessary nucleotide structures necessary for maintenance in the host, such as origin of replication sites, amplifiable selectable markers, etc., and expression in the host, such as promoters, activation sites, etc. need to be present on the RNA or DNA. Such are known to one of ordinary of the art (see Old and Primrose, *Principles of Gene Manipulation* 5th ed., Blackwell Science, Oxford, U.K. (1994)).

In some embodiments of the instant invention, more than one nucleic acid is prepared for a multipartite viral vector construct. In this case, each nucleic acid may require its own origin of assembly. Each nucleic acid could be prepared to contain a subgenomic promoter and a non-native nucleic acid. Alternatively, the insertion of a non-native nucleic acid into the nucleic acid of a monopartite virus may result in the creation of two nucleic acids (i.e., the nucleic acid necessary for the creation of a bipartite viral vector). This would be advantageous when it is desirable to keep the replication and transcription or expression of the nucleic acid of interest separate from the replication and translation of some of the coding sequences of the native nucleic acid.

The host can be any cell. The host can be any animal or plant cell. The plant cell may a protoplast, a recombinant cell, a transgenic cell, a non-transgenic cell, or a cell that is part of a cell culture, cell tissue, plant organ, or an entire plant organism. A protoplast is a plant cell that has the cell wall removed. The plant cell can be a dicot or a monocot plant cell. The host may be of a species or strain that can be infected with a viral genome or a recombinant virus obtained from a virus that can infect the host.

Plant hosts include plants of commercial interest, such as food crops, seed crops, oil crops, ornamental crops and forestry crops. For example, wheat, rice, corn, potatoes, barley, tobaccos, soybean canola, maize, oilseed rape, Arabidopsis, Nicotiana can be selected as a host plant. In particular, host plants capable of being infected by a virus containing a recombinant viral nucleic acid are preferred. Preferred host plants include Nicotiana, preferably, *Nicotiana benthamiana*, or *Nicotiana cleavlandii*.

Individual clones may be transfect into the plant host: 1) protoplasts; 2) whole plants; or 3) plant tissues, such as leaves of plants (Dijkstra et al., *Practical Plant Virology: Protocols and Exercises*, Springer Verlag (1998); *Plant Virology Protocol: From Virus Isolation to Transgenic Resistance in Methods in Molecular Biology*, Vol. 81, Foster and Taylor, Ed., Humana Press (1998)). In some embodiments of the instant invention, the delivery of the recombinant plant nucleic acid into the plant may be affected by the inoculation of in vitro transcribed RNA, inoculation of virions, or internal inoculation of plant cells from nuclear cDNA, or the systemic infection resulting from any of these procedures. In all cases, the co-infection may lead to a rapid and pervasive systemic expression of the desired nucleic acid sequences in plant cells.

The host can be infected with a recombinant viral nucleic acid or a recombinant plant virus by conventional techniques. Suitable techniques include, but are not limited to, leaf abrasion, abrasion in solution, high velocity water spray, and other injury of a host as well as imbibing host seeds with water containing the recombinant viral RNA or recombinant plant virus. More specifically, suitable techniques include:

(a) Hand Inoculations. Hand inoculations are performed using a neutral pH, low molarity phosphate buffer, with the addition of celite or carborundum (usually about 1%). One to four drops of the preparation is put onto the upper surface of a leaf and gently rubbed.

(b) Mechanized Inoculations of Plant Beds. Plant bed inoculations are performed by spraying (gas-propelled) the vector solution into a tractor-driven mower while cutting the leaves. Alternatively, the plant bed is mowed and the vector solution sprayed immediately onto the cut leaves.

(c) High Pressure Spray of Single Leaves. Single plant inoculations can also be performed by spraying the leaves with a narrow, directed spray (50 psi, 6–12 inches from the leaf) containing approximately 1% carborundum in the buffered vector solution.

(d) Vacuum Infiltration. Inoculations may be accomplished by subjecting a host organism to a substantially vacuum pressure environment in order to facilitate infection.

(e) High Speed Robotics Inoculation. Especially applicable when the organism is a plant, individual organisms may be grown in mass array such as in microtiter plates. Machinery such as robotics may then be used to transfer the nucleic acid of interest.

(f) Ballistics (High Pressure Gun) Inoculation. Single plant inoculations can also be performed by particle bombardment. A ballistics particle delivery system (BioRad Laboratories, Hercules, (A) can be used to transfect plants such as *N. benthamiana* as described previously (Nagar et al., *Plant Cell*, 7:705–719 (1995)).

An alternative method for introducing recombinant viral nucleic acids into a plant host is a technique known as agroinfection or Agrobacterium-mediated transformation (also known as Agro-infection) as described by Grimsley, et al., *Nature* 325:177 (1987). This technique makes use of a common feature of Agrobacterium which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a recombinant plant viral nucleic acid between the T-DNA border sequences results in transfer of the recombinant plant viral nucleic acid to the plant cells, where the recombinant plant viral nucleic acid is replicated, and then spreads systemically through the plant. Agro-infection has been accomplished with potato spindle tuber viroid (PSTV) (Gardner et al., *Plant Mol. Biol.* 6:221 (1986); CaV (Grimsley et al., *Proc. Natl. Acad. Sci. USA* 83:3282 (1986)); MSV (Grimsley et al., *Nature* 325:177 (1987)), and Lazarowitz, S., *Nucl. Acids Res.* 16:229 (1988)) digitaria streak virus (Donson et al., *Virology* 162:248 (1988)), wheat dwarf virus (Hayes et al, *J. Gen. Virol.* 69:891 (1988)) and tomato golden mosaic virus (TGMV) (Elmer et al., *Plant Mol. Biol.* 10:225 (1988) and Gardiner et al., *EMBO J.* 7:899 (1988)). Therefore, agro-infection of a susceptible plant could be accomplished with a virion containing a recombinant plant viral nucleic acid based on the nucleotide sequence of any of the above viruses. Particle bombardment or electrosporation or any other methods known in the art may also be used.

In some embodiments of the instant invention, infection may also be attained by placing a selected nucleic acid sequence into an organism such as *E. coli*, or yeast, either integrated into the genome of such organism or not, and then applying the organism to the surface of the host organism. Such a mechanism may thereby produce secondary transfer of the selected nucleic acid sequence into a host organism. This is a particularly practical embodiment when the host organism is a plant. Likewise, infection may be attained by first packaging a selected nucleic acid sequence in a pseudovirus. Such a method is described in WO 94/10329. Though the teachings of this reference may be specific for bacteria, those of skill in the art will readily appreciate that the same procedures could easily be adapted to other organisms.

Plant may be grown from seed in a mixture of "Peat-Lite Mix™ (Speedling, Inc. Sun City, Fla.) and Nutricote™ controlled release fertilizer 14-14-14 (Chiss-Asahi Fertilizer Co., Tokyo, Japan). Plants may be grown in a controlled environment provided 16 hours of light and 8 hours of darkness. Sylvania "Gro-Lux/Aquarium" wide spectrum 40 watt fluorescent grow lights. (Osram Sylvania Products, Inc. Danvers, Mass.) may be used. Temperatures may be kept at around 80° F. during light hours and 70° F. during dark hours. Humidity may be between 60 and 85%.

A library of sequence inserts from one or more donor organism(s) may be constructed using any of the following methods.

A recombinant plant viral nucleic acid may be prepared by cloning a viral nucleic acid. If the viral nucleic acid is DNA, it can be cloned directly into a suitable vector using conventional techniques. One technique is to attach an origin of replication to the viral DNA which is compatible with the cell to be transfected. In this manner, DNA copies of the chimeric nucleotide sequence are produced in the transfected cell. If the viral nucleic acid is RNA, a DNA copy of the viral nucleic acid is first prepared by well-known procedures. For example, the viral RNA is transcribed into DNA using reverse transcriptase to produce subgenomic DNA pieces, and a double-stranded DNA may be produced using DNA polymerases. The cDNA is then cloned into appropriate vectors and cloned into a cell to be transfected. In some instances, cDNA is first attached to a promoter which is compatible with the production cell. The recombinant plant viral nucleic acid can then be cloned into any suitable vector which is compatible with the production cell. Alternatively, the recombinant plant viral nucleic acid is inserted in a vector adjacent a promoter which is compatible with the production cell. In some embodiments, the cDNA ligated vector may be directly transcribed into infectious RNA in vitro and inoculated onto the plant host. The cDNA pieces are mapped and combined in proper sequence to produce a full-length DNA copy of the viral RNA genome, if necessary.

The donor organism from which a library of sequence inserts is derived includes Kingdom Monera, Kingdom Protista, Kingdom Fungi, Kingdom Plantae and Kingdom Animalia. Kingdom Monera includes subkingdom Archaebacteriobionta (archaebacteria): division Archaebacteriophyta (methane, salt and sulfolobus bacteria); subkingdom Eubacteriobionta (true bacteria): division Eubacteriophyta; subkingdom Viroids; and subkingdom Viruses. Kingdom Protista includes subkingdom Phycobionta: division Xanthophyta 275 (yellow-green algae), division Chrysophyta 400 (golden-brown algae), division Dinophyta (Pyrrhophyta) 1,000 (dinoflagellates), division Bacillariophyta 5,500 (diatoms), division Cryptophyta 74 (cryptophytes), division Haptophyta 250 (haptonema organisms), division Euglenophyta 550 (euglenoids), division Chlorophyta, class Chlorophyceae 10,000 (green algae), class Charophyceae 200 (stoneworts), division Phaeophyta 900 (brown algae), and division Rhodophyta 2,500 (red algae); subkingdom Mastigobionta 960: division Chytridiomycota 750 (chytrids), and division Oomycota (water molds) 475; subkingdom Myxobionta 320: division Acrasiomycota (cellular slime molds) 21, and division Myxomycota 500 (true slime molds). Kingdom Fungi includes division Zygomycota 570 (coenocytic fungi): subdivision Zygomycotina; and division Eumycota 350 (septate fungi): subdivision Ascomycotina 56,000 (cup fungi), subdivision Basidiomycotina 25,000 (club fungi), subdivision Deuteromycotina 22,000 (imperfect fungi), and subdivision Lichenes 13,500. Kingdom Plantae includes division Bryophyta, Hepatophyta, Anthocerophyta, Psilophyta, Lycophyta, Sphenophyta, Pterophyta, Coniferophyta, Cycadeophyta, Ginkgophyta, Gnetophyta and Anthophyta. Kingdom Animalia includes: Porifera (Sponges), Cnidaria (Jellyfishes), Ctenophora (Comb Jellies), Platyhelminthes (Flatworms), Nemertea (Proboscis Worms), Rotifera (Rotifers), Nematoda (Roundworms), Mollusca (Snails, Clams, Squid & Octopus), Onychophora (Velvet Worms), Annelida (Segmented Worms), Arthropoda (Spiders & Insects), Phoronida, Bryozoa (Bryozoans), Brachiopoda (Lamp Shells), Echinodermata (Sea Urchins & starfish), and Chordata (Vertebrata-Fish, Birds, Reptiles, Mammals). A preferred donor organism is human. Host organisms are those capable of being infected by an infectious RNA or a virus containing a recombinant viral nucleic acid. Host organisms include organisms from Monera, Protista, Fungi and Animalia. Preferred host organisms are organisms from Fungi, such as yeast (for example, *S. cerevisiae*) and Anamalia, such as insects (for example, *C. elegans*).

To prepare a DNA insert comprising a nucleic acid sequence of a donor organism, the first step is to construct a cDNA library, a genomic DNA library, or a pool of mRNA of the donor organism. Full-length cDNAs or genomic DNA can be obtained from public or private repositories. For example, cDNA and genomic libraries from bovine, chicken, dog, drosophila, fish, frog, human, mouse, porcine, rabbit, rat, and yeast; and retroviral libraries can be obtained from Clontech (Palo Alto, Calif.). Alternatively, cDNA library can be prepared from a field sample by methods known to a person of ordinary skill, for example, isolating mRNAs and transcribing mRNAs into cDNAs by reverse transcriptase (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)). Genomic DNAs represented in BAC (bacterial artificial chromosome), YAC (yeast artificial chromosome), or TAC (transformation-competent artificial chromosome, Lin et al., *Proc. Natl. Acad. Sci. USA,* 96:6535–6540 (1999)) libraries can be obtained from public or private repositories.

Alternatively, a pool of genes, which are overexpressed in a tumor cell line compared with a normal cell line, can be prepared or obtained from public or private repositories. Zhang et al. (*Science,* 276: 1268–1272 (1997)) report that using a method of serial analysis of gene expression (SAGE) (Velculescu et al, *Cell,* 88:243 (1997)), 500 transcripts that were expressed at significantly different levels in normal and neoplastic cells were identified. The expression of DNAs that overexpresses in a tumor cell line in a host organism may cause changes in the host organism, thus a pool of such DNAs is another source for DNA inserts for this invention. The BAC/YAC/TAC DNAs, DNAs or cDNAs can be mechanically size-fractionated or digested by an enzyme to smaller fragments. The fragments are ligated to adapters with cohesive ends, and shotgun-cloned into recombinant viral nucleic acid vectors. Alternatively, the fragments can be blunt-end ligated into recombinant viral nucleic acid vectors. Recombinant viral nucleic acids containing a nucleic acid sequence derived from the cDNA library or genomic DNA library is then constructed using conventional techniques. The recombinant viral nucleic acid vectors produced comprise the nucleic acid insert derived from the donor organism. The nucleic acid sequence of the recombinant viral nucleic acid is transcribed as RNA in a host organism; the RNA is capable of regulating the expression of a phenotypic trait by a positive or anti sense mechanism. The nucleic acid sequence may also regulate the expression of more than one phenotypic trait. Nucleic acid sequences from Monera, Protista, Fungi, Plantae and Animalia may be used to assemble the DNA libraries. This method may thus be used to discover useful dominant gene phenotypes from DNA libraries through the gene expression in a host organism.

In the case of using plant as a donor organism, the donor plant and the host plant may be genetically remote or unrelated: they may belong to different genus, family, order, class, subdivision, or division. Donor plants include plants of commercial interest, such as food crops, seed crops, oil crops, ornamental crops and forestry crops. For example, wheat, rice, corn, potatoes, barley, tobaccos, soybean canola, maize, oilseed rape, Arabidopsis, Nicotiana can be selected as a donor plant.

To prepare a DNA insert comprising a nucleic acid sequence of a donor plant, the first step is typically to construct a library of cDNAs, genomic DNAs, or a pool of RNAs of the plant of interest. Full-length cDNAs can be obtained from public or private repositories, for example, cDNA library of *Arabidopsis thaliana* can be obtained from the Arabidopsis Biological Resource Center. Alternatively, cDNA library can be prepared from a field sample by methods known to a person of ordinary skill, for example, isolating mRNAs and transcribing mRNAs into cDNAs by reverse transcriptase (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)). Genomic DNAs represented in BAC (bacterial artificial chromosome), YAC (yeast artificial chromosome), or TAC (transformation-competent artificial chromosome, Liu et al., *Proc. Natl. Acad. Sci. USA*, 96:6535–6540 (1999)) libraries can be obtained from public or private repositories, for example, the Arabidopsis Biological Resource Center. The BAC/YAC/TAC DNAs or cDNAs can be mechanically size-fractionated or digested by an enzyme to smaller fragments. The fragments are ligated to adapters with cohesive ends, and shotgun-cloned into recombinant viral nucleic acid vectors. Alternatively, the fragments can be blunt-end ligated into recombinant viral nucleic acid vectors. Recombinant plant viral nucleic acids containing a nucleic acid sequence derived from the cDNA library or genomic DNA library is then constructed using conventional techniques. The recombinant viral nucleic acid vectors produced comprise the nucleic acid insert derived from the donor plant. The nucleic acid sequence of the recombinant viral nucleic acid is transcribed as RNA in a host plant; the RNA is capable of regulating the expression of a phenotypic trait by a positive or anti sense mechanism. The nucleic acid sequence may also code for the expression of more than one phenotypic trait. Sequences from wheat, rice, corn, potato, barley, tobacco, soybean, canola, maize, oilseed rape, Arabidopsis, and other crop species may be used to assemble the DNA libraries. This method may thus be used to search for useful dominant gene phenotypes from DNA libraries through the gene expression.

Those skilled in the art will understand that these embodiments are representative only of many constructs suitable for the instant invention. All such constructs are contemplated and intended to be within the scope of the present invention. The invention is not intended to be limited to any particular viral constructs but specifically contemplates using all operable constructs. A person skilled in the art will be able to construct the plant viral nucleic acids based on molecular biology techniques well known in the art. Suitable techniques have been described in Sambrook et al. (2nd ed.), Cold Spring Harbor Laboratory, Cold Spring Harbor (1989); *Methods in Enzymol.* (Vols. 68, 100, 101, 118, and 152–155) (1979, 1983, 1986 and 1987); and *DNA Cloning*, D. M. Clover (ed.), IRL Press, Oxford (1985); Walkey, *Applied Plant Virol.*, Chapman & Hall (1991); Matthews, *Plant Virol.*, 3$^{rd}$ Ed., Academic Press, San Diego (1991); Turpen et al., *J. of Virological Methods*, 42:227–240 (1993); U.S. Pat. Nos. 4,885,248, 5,173,410, 5,316,931, 5,466,788, 5,491,076, 5,500,360, 5,589,367, 5,602,242, 5,627,060, 5,811,653, 5,866,785, 5,889,190, 5,589,367, and 5,977,438. Nucleic acid manipulations and enzyme treatments are carried out in accordance with manufacturers' recommended procedures in making such constructs.

Any of the following methods for detecting phenotypic or biochemical changes as a result of expression of the transcriptional unit may be used.

After a plant host is infected with individual clone of the library, one or more phenotypic or biochemical changes may be detected. The phenotypic changes in a plant host may be determined by any known methods in the art. Phenotypic changes may include growth rate, color, or morphology changes. Typically, these methods include visual, macroscopic or microscopic analysis. For example, growth changes, such as stunting, color changes (e.g. leaf yellowing, mottling, bleaching, chlorosis) among others are easily visualized. Examples of morphological changes include, developmental defects, wilting, necrosis, among others.

Biochemical changes can be determined by any analytical methods known in the art for detecting, quantitating, or isolating DNA, RNA, proteins, antibodies, carbohydrates, lipids, and small molecules. Selected methods may include Northern, Western blotting, matrix-assisted laser desorption time of flight mass spectrometry (MALDI-TOF), LC/MS, GC/MS, two-dimensional IEF/SDS-PAGE, enzyme-linked immunosorbent assay (ELISA), etc. In particular, suitable methods may be performed in a high-throughput, fully automated fashion using robotics. Examples of biochemical changes may include the accumulation of substrates or products from enzymatic reactions, changes in biochemical pathways, inhibition or augmentation of endogenous gene expression in the cytoplasm of cells, changes in the RNA or protein profile. For example, the clones in the viral vector library may be functionally classified based on metabolic pathway affected or visual/selectable phenotype produced in the organism. This process enables a rapid determination of gene function for unknown nucleic acid sequences of a donor organism as well as a host organism. Furthermore, this process can be used to rapidly confirm function of full-length DNA's of unknown function. Functional identification of unknown nucleic acid sequences in a library of one organism may then rapidly lead to identification of similar unknown sequences in expression libraries for other organisms based on sequence homology. Such information is useful in many aspects including in human medicine.

The biochemical or phenotypic changes in the infected host plant may be correlated to the biochemistry or phenotype of a host plant that is uninfected. Optionally, the biochemical or phenotypic changes in the infected host plant is further correlated to a host plant that is infected with a viral vector that contains a control nucleic acid of a known sequence. The control nucleic acid may have similar size but is different in sequence from the nucleic acid insert derived from the library. For example, if the nucleic acid insert derived from the library is identified as encoding a GTP binding protein in an antisense orientation, a nucleic acid derived from a gene encoding green fluorescent protein can be used as a control nucleic acid. Green fluorescent protein is known not to have the same effect as the GTP binding protein when expressed in a host plant.

In some embodiments, the phenotypic or biochemical trait may be determined by complementation analysis, that is, by observing the endogenous gene or genes whose function is replaced or augmented by introducing the nucleic acid of interest. A discussion of such phenomenon is provided by Napoli et al., *The Plant Cell* 2:279–289 (1990). The phenotypic or biochemical trait may also be determined by (1) analyzing the biochemical alterations in the accumulation of substrates or products from enzymatic reactions according to any means known by those skilled in the art; (2) by observing any changes in biochemical pathways which may be modified in a host organism as a result of expression of the nucleic acid; (3) by utilizing techniques known by those skilled in the art to observe inhibition of endogenous gene expression in the cytoplasm of cells as a result of expression of the nucleic acid.; (4) by utilizing techniques known by those skilled in the art to observe changes in the RNA or protein profile as a result of expression of the nucleic acid; or (5) by selection of organisms capable of growing or maintaining viability in the presence of noxious or toxic substances, such as, for example, pharmaceutical ingredients.

One useful means to determine the function of nucleic acids transfected into a host plant is to observe the effects of gene silencing. Traditionally, functional gene knockout has been achieved following inactivation due to insertion of transposable elements or random integration of T-DNA into the chromosome, followed by characterization of conditional, homozygous-recessive mutants obtained upon backcrossing. Some teachings in these regards are provided by WO97/42210 which is herein incorporated by reference. As an alternative to traditional knockout analysis, an EST/DNA library from a donor organism, may be assembled into a viral transcription plasmid. The nucleic acid sequences in the transcription plasmid library may then be introduced into host cells as part of a functional RNA virus which post-transcriptionally silences the homologous target gene. The EST/DNA sequences may be introduced into a viral vector in either the plus or anti sense orientation, and the orientation can be either directed or random based on the cloning strategy. A high-throughput, automated cloning scheme based on robotics may be used to assemble and characterize the library. Alternatively, the EST/cDNA sequences can be inserted into the genomic RNA of a viral vector such that they are represented as genomic RNA during the viral replication in host cells. The library of EST clones is then transcribed into infectious RNAs and inoculated onto a host organism susceptible to viral infection. The viral RNAs containing the EST/cDNA sequences contributed from the original library are now present in a sufficiently high concentration in the cytoplasm of host organism cells such that they cause post-transcriptional gene silencing of the endogenous gene in a host organism. Since the replication mechanism of the virus produces both sense and antisense RNA sequences, the orientation of the EST/cDNA insert is normally irrelevant in terms of producing the desired phenotype in the host organism.

The present invention provides a method to express transiently viral-derived positive sense or antisense RNAs in transfected plants. Such method is much faster than the time required to obtain genetically engineered antisense transgenic organisms. Systemic infection and expression of viral antisense RNA occurs as short as several days post inoculation, whereas it takes several months or longer to create a single transgenic organism. The invention provides a method to identify genes involved in the regulation of growth by inhibiting the expression of specific endogenous genes using viral vectors. This invention provides a method to characterize specific genes and biochemical pathways in donor organisms or in host plants using an RNA viral vector.

It is known that silencing of endogenous genes can be achieved with homologous sequences from the same plant family. For example, Kumagai et al., (*Proc. Natl. Acad. Sci. USA* 92:1679 (1995)) report that the *Nicotiana benthamiana* gene for phytoene desaturase (PDS) was silenced by transfection with a viral RNA derived from a clone containing a partial tomato (*Lycopersicon esculentum*) cDNA encoding PDS being in an antisense orientation. Kumagai et al. demonstrate that gene encoding PDS from one plant can be silenced by transfecting a host plant with a nucleic acid of a known sequence, namely, a PDS gene, from a donor plant of the same family. The present invention provides a method of silencing a gene in a host organism by transfecting a non-plant host organism with a viral nucleic acid comprising a nucleic acid insert derived from a cDNA library or a genomic DNA library or a pool of RNA from a non-plant organism. Different from Kumagai et al, the sequence of the nucleic acid insert in the present invention does not need to be identified prior to the transfection. Another feature of the present invention is that it provides a method to silence a conserved gene of a non-plant kingdom; the antisense transcript of an organism results in reducing expression of the endogenous gene of a host organism from Monera, Protista, Fungi and Animalia. The invention is exemplified by GTP binding proteins. In eukaryotic cells, GTP-binding proteins function in a variety of cellular processes, including signal transduction, cytoskeletal organization, and protein transport. Low molecular weight (20–25 kDa) of GTP-binding proteins include ras and its close relatives (for example, Ran), rho and its close relatives, the rab family, and the ADP-ribosylation factor (ARF) family. The heterotrimeric and monomeric GTP-binding proteins that may be involved in secretion and intracellular transport are divided into two structural classes: the rab and the ARF families. The ARFs from many organisms have been isolated and characterized. The ARFs share structural features with both the ras and trimeric GTP-binding protein families. The present invention demonstrates that the gene of a plant, such as barley, can be silenced by transfection with infectious RNAs from a clones containing a full-length or partial cDNA of the PDS open reading frame in a sense orientation, derived from a plant of a different family, such as rice and maize. The present invention also demonstrates that PDS proteins are highly homologous in plants, not only at the amino acid level, but also at the nucleic acid level. The present invention thus provides a method to silence a conserved gene in a host organism, by transfecting the host with infectious RNAs derived from a homologous gene of a different plant organism.

A library of human nucleic acid sequences is cloned into vectors. The vectors are applied to the host to obtain infection. Each infected host is grown with an uninfected host and a host infected with a null vector. A null vector will show no phenotypic or biochemical change other than the effects of the virus itself. Each host is observed daily or regularly for visual differences between the infected host and its two controls. In each host displaying an observable phenotypic or biochemical change a trait is identified. The donor nucleic acid sequence is identified, the full-length gene sequence is obtained and the full-length gene in the host is obtained, if a gene from the host is associated with the trait. Both genes are sequenced and homology is determined. A variety of biochemical tests may also be made on the host or host tissue depending on the information that is desired. A variety of phenotypic changes or traits and biochemical tests are set forth in this document. A functional gene profile can be obtained by repeating the process several times.

Large amounts of DNA sequence information are being generated in the public domain, which may be entered into a relational database. Links may be made between sequences from various species predicted to carry out similar biochemical or regulatory functions. Links may also be generated between predicted enzymatic activities and visually displayed biochemical and regulatory pathways. Likewise, links may be generated between predicted enzymatic or regulatory activity and known small molecule inhibitors, activators, substrates or substrate analogs. Phenotypic data from expression libraries expressed in transfected hosts may be automatically linked within such a relational database. Genes with similar predicted roles of interest in other organisms may be rapidly discovered.

The present invention is also directed to a method of changing the phenotype or biochemistry of a plant by expressing transiently a nucleic acid sequence from a donor plant in a sense or antisense orientation in a host plant, which inhibits an endogenous gene expression in the meristem of the host plant. The one or more phenotypic or biochemical changes in the host plant are detected by methods as describes previously. Transient expressing a nucleic acid sequence in a host plant can affect the gene expression in meristem. Meristems are of interest in plant development because plant growth is driven by the formation and activity of meristems throughout the entire life cycle. This invention is exemplified by a nucleic acid sequence encoding ribosomal protein S18. The activity of S18 promoter is restricted to meristems (Lijsebettesn et al., *EMBO J*. 13: 3378–3388). Transient expression of a nucleic acid sequence in a host plant can trigger a signal transmitting to meristems and affect the gene expression in meristem.

One problem with gene silencing in a plant host is that many plant genes exist in multigene families. Therefore, effective silencing of a gene function may be especially problematic. According to the present invention, however, nucleic acids may be inserted into the viral genome to effectively silence a particular gene function or to silence the function of a multigene family. It is presently believed that about 20% of plant genes exist in multigene families.

A detailed discussion of some aspects of the "gene silencing" effect is provided in U.S. Pat. No. 5,922,602; the disclosure of which is incorporated herein by reference. RNA can reduce the expression of a target gene through inhibitory RNA interactions with target mRNA that occur in the cytoplasm and/or the nucleus of a cell.

An EST/cDNA library from a plant such as *Arabidopsis thaliana* may be assembled into a plant viral transcription plasmid background. The cDNA sequences in the transcription plasmid library can then be introduced into plant cells as cytoplasmic RNA in order to post-transcriptionally silence the endogenous genes. The EST/cDNA sequences may be introduced into the plant viral transcription plasmid in either the plus or anti-sense orientation (or both), and the orientation can be either directed or random based on the cloning strategy. A high-throughput, automated cloning strategy using robotics can be used to assemble the library. The EST clones can be inserted behind a duplicated subgenomic promoter such that they are represented as subgenomic transcripts during viral replication in plant cells. Alternatively, the EST/cDNA sequences can be inserted into the genomic RNA of a plant viral vector such that they are represented as genomic RNA during the viral replication in plant cells. The library of EST clones is then transcribed into infectious RNAs and inoculated onto a host plant susceptible to viral infection. The viral RNAs containing the EST/cDNA sequences contributed from the original library are now present in a sufficiently high concentration in the cytoplasm of host plant cells such that they cause post-transcriptional gene silencing of the endogenous gene in a host plant. Since the replication mechanism of the virus produces both sense and antisense RNA sequences, the orientation of the EST/cDNA insert is normally irrelevant in terms of producing the desired phenotype in the host plant.

Genomic libraries containing sequences from rice, barley, corn, soybean and other important crops can be obtained from public and private sources, or be prepared from plant genomic DNAs. BAC clones containing entire plant genomes have been constructed and organized in a minimal overlapping order. Individual BACs are sheared to fragments and directly cloned into viral vectors. Clones that completely cover an entire BAC form a BAC viral vector sublibrary. Genomic clones can be identified by probing filters containing BACs with labeled nucleic acid inserts which result in changes in a host plant, or with labeled probes prepared from DNAs encoding the gene of interest of any organism that has already been cloned. Useful labels include radioactive, fluorescent, or chemiluminecent molecules, enzymes, etc. BACs that hybridize to the probe are selected and their corresponding BAC viral vectors are used to produce infectious RNAs. Plants that are transfected with the BAC sublibrary are screened for change of function, for example, change of growth rate or change of color. Once the change of function is observed, the inserts from these clones or their corresponding plasmid DNAs are characterized by dideoxy sequencing. This provides a rapid method to obtain the genomic sequence for a plant protein.

The recombinant nucleic acids and recombinant viruses used in the present invention are constructed using techniques well known in the art. Suitable techniques have been described in Sambrook et al., *Molecular Cloning* (2d ed.), Cold Spring Harbor Laboratory, Cold Spring Harbor (1982, 1989); *Methods in Enzymol*. (Vols. 68, 100, 101, 118, and 152–155) (1979, 1983, 1986, and 1987); DNA Cloning, D. M. Clover, Ed., IRL Press, Oxford (1985); and, *Principles of Gene Manipulation* (5th ed.), R. W. Old et al., Blackwell Science, Oxford (1994). Medium compositions have been described by Miller, J., *Experiments in Molecular Genetics*, Cold Spring Harbor Laboratory, New York (1972), as well as the references previo0usly identified, all of which are incorporated herein by reference. DNA manipulations and enzyme treatments are carried out in accordance with manufacturers' recommended procedures in making such constructs.

In order to provide an even clearer and more consistent understanding of the specification and the claims, including the scope given herein to such terms, the following definitions are provided:

Anti-Sense Inhibition: A type of gene regulation based on cytoplasmic, nuclear or organelle inhibition of gene expression due to the presence in a cell of an RNA molecule complementary to at least a portion of the mRNA being translated. It is specifically contemplated that RNA molecules may be from either an RNA virus or mRNA from the host cells genome or from a DNA virus.

Cell Culture: A proliferating group of cells which may be in either an undifferentiated or differentiated state, growing contiguously or non-contiguously.

Chimeric Sequence or Gene: A nucleotide sequence derived from at least two heterologous parts. The sequence may comprise DNA or RNA.

Coding Sequence: A deoxyribonucleotide or ribonucleotide sequence which, when either transcribed and translated or simply translated, results in the formation of a cellular polypeptide or a ribonucleotide sequence which, when translated, results in the formation of a cellular polypeptide.

Compatible: The capability of operating with other components of a system. A vector or plant or animal viral nucleic acid which is compatible with a host is one which is capable of replicating in that host. A coat protein which is compatible with a viral nucleotide sequence is one capable of encapsidating that viral sequence.

Complementation Analysis: As used herein, this term refers to observing the changes produced in an organism when a nucleic acid sequence is introduced into that organism after a selected gene has been deleted or mutated so that it no longer functions fully in its normal role. A complementary gene to the deleted or mutated gene can restore the genetic phenotype of the selected gene.

Dual Heterologous Subgenomic Promoter Expression System (DHSPES): a plus stranded RNA vector having a dual heterologous subgenomic promoter expression system to increase, decrease, or change the expression of proteins, peptides or RNAs, preferably those described in U.S. Pat. Nos. 5,316,931, 5,811,653, 5,589,367, and 5,866,785, the disclosure of which is incorporated herein by reference.

Expressed sequence tags (ESTs): Relatively short single-pass DNA sequences obtained from one or more ends of cDNA clones and RNA derived therefrom. They may be present in either the 5' or the 3' orientation. ESTs have been shown useful for identifying particular genes.

Expression: The term as used herein is meant to incorporate one or more of transcription, reverse transcription and translation.

A Functional Gene Profile: The collection of genes of an organism which code for a biochemical or phenotypic trait. The functional gene profile of an organism is found by screening nucleic acid sequences from a donor organism by over expression or suppression of a gene in a host organism. A functional gene profile requires a collection or library of nucleic acid sequences from a donor organism. A functional gene profile will depend on the ability of the collection or library of donor nucleic acids to cause over-expression or suppression in the host organism. Therefore, a functional gene profile will depend upon the quantity of donor genes capable of causing over-expression or suppression of host genes or of being expressed in the host organism in the absence of a homologous host gene.

Gene: A discrete nucleic acid sequence responsible for producing one or more cellular products and/or performing one or more intercellular or intracellular functions.

Gene silencing: A reduction in gene expression. A viral vector expressing gene sequences from a host may induce gene silencing of homologous gene sequences.

Homology: A degree of nucleic acid similarity in all or some portions of a gene sequence sufficient to result in gene suppression when the nucleic acid sequence is delivered in the antisense orientation.

Host: A cell, tissue or organism capable of replicating a nucleic acid such as a vector or viral nucleic acid and which is capable of being infected by a virus containing the viral vector or viral nucleic acid. This term is intended to include prokaryotic and eukaryotic cells, organs, tissues or organisms, where appropriate. Bacteria, fungi, yeast, and animal (cell, tissues, or organisms), are examples of a host.

Infection: The ability of a virus to transfer its nucleic acid to a host or introduce a viral nucleic acid into a host, wherein the viral nucleic acid is replicated, viral proteins are synthesized, and new viral particles assembled. In this context, the terms "transmissible" and "infective" are used interchangeably herein. The term is also meant to include the ability of a selected nucleic acid sequence to integrate into a genome, chromosome or gene of a target organism.

Insert: a stretch of nucleic acid sequence, typically more than 20 base pairs long.

Multigene family: A set of genes descended by duplication and variation from some ancestral gene. Such genes may be clustered together on the same chromosome or dispersed on different chromosomes. Examples of multigene families include those which encode the histones, hemoglobins, immunoglobulins, histocompatibility antigens, actions, tubulins, keratins, collagens, heat shock proteins, salivary glue proteins, chorion proteins, cuticle proteins, yolk proteins, and phaseolins.

Non-Native: Any RNA or DNA sequence that does not normally occur in the cell or organism in which it is placed. Examples include recombinant viral nucleic acids and genes or ESTs contained therein. That is, an RNA or DNA sequence may be non-native with respect to a viral nucleic acid. Such an RNA or DNA sequence would not naturally occur in the viral nucleic acid. Also, an RNA or DNA sequence may be non-native with respect to a host organism. That is, such a RNA or DNA sequence would not naturally occur in the host organism.

Nucleic acid: As used herein the term is meant to include any DNA or RNA sequence from the size of one or more nucleotides up to and including a complete gene sequence. The term is intended to encompass all nucleic acids whether naturally occurring in a particular cell or organism or non-naturally occurring in a particular cell or organism.

Nucleic acid of interest: The term is intended to refer to the nucleic acid sequence whose function is to be determined. The sequence will normally be non-native to a viral vector but may be native or non-native to a host organism.

Phenotypic Trait: An observable, measurable or detectable property resulting from the expression or suppression of a gene or genes.

Plant Cell: The structural and physiological unit of plants, consisting of a protoplast and the cell wall.

Plant Organ: A distinct and visibly differentiated part of a plant, such as root, stem, leaf or embryo.

Plant Tissue: Any tissue of a plant in plant or in culture. This term is intended to include a whole plant, plant cell, plant organ, protoplast, cell culture, or any group of plant cells organized into a structural and functional unit.

Positive-sense inhibition: A type of gene regulation based on cytoplasmic inhibition of gene expression due to the presence in a cell of an RNA molecule substantially homologous to at least a portion of the mRNA being translated.

Promoter: The 5'-flanking, non-coding sequence substantially adjacent a coding sequence which is involved in the initiation of transcription of the coding sequence.

Protoplast: An isolated plant or bacterial cell without some or all of its cell wall.

Recombinant Viral Nucleic Acid: Viral nucleic acid which has been modified to contain non-native nucleic acid sequences. These non-native nucleic acid sequences may be from any organism or purely synthetic, however, they may also include nucleic acid sequences naturally occurring in the organism into which the recombinant viral nucleic acid is to be introduced.

Recombinant Virus: A virus containing the recombinant viral nucleic acid.

Sense Inhibition: A type of gene regulation based on cytoplasmic, nuclear or organelle inhibition of gene expression due to the presence in a cell of an RNA molecule identical or homologous in sequence to at least a portion of the MRNA being translated. It is specifically contemplated that RNA molecules may be from either an RNA virus or mRNA from the host cells genome or from a DNA virus.

Subgenomic Promoter: A promoter of a subgenomic mRNA of a viral nucleic acid.

Substantial Sequence Homology: Denotes nucleotide sequences that are substantially functionally equivalent to one another. Nucleotide differences between such sequences having substantial sequence homology are insignificant in affecting function of the gene products or an RNA coded for by such sequence.

Systemic Infection: Denotes infection throughout a substantial part of an organism including mechanisms of spread other than mere direct cell inoculation but rather including transport from one infected cell to additional cells either nearby or distant.

Targeting Nucleotide Sequence: a nucleotide sequence specifically for targeting the down-regulation or silencing of a gene of interest.

Transient Expression: Expression of a nucleic acid sequence in a host without insertion of the nucleic acid sequence into the host genome, such as by way of a viral vector.

EXAMPLES

The following examples further illustrate the present invention. These examples are intended merely to be illustrative of the present invention and are not to be construed as being limiting.

Biological Deposits.

The following strains were deposited with the ATCC, 10801 University Blvd., Manassas, Va. 20110, U.S.A., on Jan. 18, 2001 (viral vectors are in $E.\ coli$ strain DH5α): DH5α: α.42 (Deposit No.: PTA-2938); DH5α: β.42.Sp1 (Deposit No.: PTA-2934); DH5α: β.Δβa(Deposit No.: PTA-2942); DH5α: β.Δβb.GFP (β.GPFc3.Δβb) (Deposit No.: PTA-2935); DH5α:β.GFP::βb (β.GFPc3::βb) (Deposit No.: PTA-2940); DH5α:β.GFP::2A (β.GFPc3::2A::βb) (Deposit No.: PTA-2931); DH5α:γ42(Deposit No.: PTA-2939); DH5α:γ.GFP::γb (γ.GFPc3::γb) (Deposit No.: PTA-2944); DH5α:γ.GFP::HA::2A::γb (γ.GFPc3::HA::2A::γb) (Deposit No.: PTA-2932); DH5α:γ.Δγa.γb.GFP (γ.Δa.Δγb.GFPc3) (Deposit No.: PTA-2943); DH5α:γ.Δγb.GFP (γ.Δb.GFPc3) (Deposit No.: PTA-2930); DH5α:γ.bPDS4 (γ.γb.stop.bPDS4) (Deposit No.: 2937); DH5α: γ.bPDS4-as (γ.γb.stop.bPDS4-as) (Deposit No.: PTA-2933); DH5α:γ.Δγa(Deposit No.: PTA-2941); and, DH5α:γ.2A::GFP::H (γ.γ::2A::GFP::H) (Deposit No.: PTA-2936).

Example 1

Expression of Heterologous Protein Fusions From RNA γ.

Construction of γ RNA-Based Monocot Viral Vectors.

An infectious BSMV RNA gamma (γ) cDNA clone (γ42) (Petty, et al. 1989) was modified to express foreign inserts from the γ subgenomic RNA 1, using the γb subgenomic promoter (sgp) (FIG. 1A). The γ42 cDNA was modified to replace nucleotides 5098–5103 with a Nhe I site by site-directed mutagenesis using the oligonucleotide 5' CTTCT-TCCGTTGCTAGCTAAAAAAAAAA 3' (SEQ ID NO: 11) to generate the plasmid γ42.NheI (FIG. 1B). This plasmid was further modified to change the MluI plasmid linearization restriction site that immediate follows the viral sequence to one that would not be found in foreign insert sequences. MluI was changed to the 6 base pair (bp) restriction site, BssHII by digesting γ42.NheI with MluI, filling in the overhang with the Klenow fragment of DNA polymerase I, and religating to generate the plasmid γ42.NheI-B (FIG. 1B). The BssHII restriction site in γ42.NheI-B was replaced with the 8 base pair restriction site, SwaI, using polymerase chain reaction (PCR) mutagenesis. To achieve this, a 433 bp fragment was amplified from γ42 using the oligonucleotides 5' AGTTACTTCT-TGAATTTCTCC 3' (SEQ ID NO: 12) (upstream) and 5' TATAGCGCGCATTTAAATTGGTCTTC-CCTTGGGGGACCG 3' (SEQ ID NO: 13) (downstream). The PCR fragment was digested with Hpa I and Bss HII and inserted between the Hpa I and Bss HII sites of γ42.NheI-B to generate γ42.NheI-S (FIG. 1B).

Subsequently, a 646 bp Nhe I fragment, containing the zeomycin resistance gene as a cloning marker, was amplified from pZEr0 (Invitrogen Corporation, Carlsbad, Calif., USA) using PCR mutagenesis with the oligonucleotides 5' TAT-GCTAGCTGATTAATTAAGTCGACGAGCT-GATTTAACAAATTTTAAC 3'3' (SEQ ID NO: 14) (upstream) and 5' TATGCTAGCTGAGCGGCCGCG-CACGTGTCAGTCCTGCTCCTCGG 3' (SEQ ID NO: 15) (downstream) as primers. This PCR fragment was digested with Nhe I and inserted into the Nhe I site of γ42.NheI-B and γ42.NheI-S to generate four plasmids, γ.γb.stop.P/N.Zeo-B (positive orientation), γbγstop.N/P.Zeo-B (negative orientation) and γ.γb.stop.P/N.Zeo-S (positive orientation), γ.γb.stop.N/P.Zeo-S (negative orientation), respectively (FIG. 1C). All four plasmids have PacI and NotI sites flanking the zeomycin resistance gene and contain a stop codon at the end of the γb ORF to prevent translation of downstream sequences.

Figure 2A:
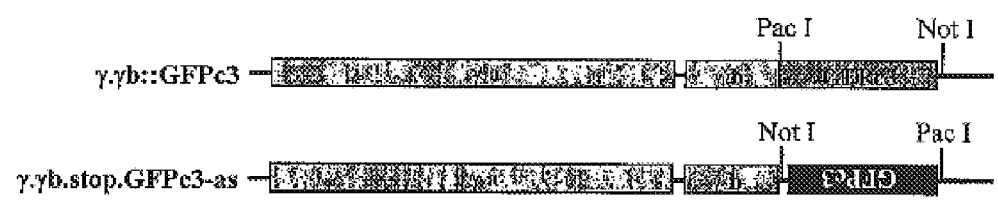
FIG. 2A depicts the genetic structure of two RNAγ constructs: "γ.γb::GFPc3" and "γ.γb::GFPc3-as" (including the restriction sites for PacI and NotI).

The BSMV γ42.NheI-S cDNA was modified to express GFPc3 as a fusion to the C-terminus of the BSMV γb protein in either the sense and antisense orientation. Using PCR mutagenesis a 764 bp fragment, containing the green fluorescent protein cycle 3 (GFPc3) open reading frame (ORF) (Crameri, et al., 1996), was amplified from TMV-SBS5::GFPc3 using the oligonucleotides 5' TATACTAGTT-TAATTAAGTCGACCATGGCTAGCAAAG-GAGAAGAAC 3' (SEQ ID NO: 16) (upstream) and 5' TATACTAGTTGAGCGGCCGCTTATTTG-TAGAGCTCATCCATGCC 3' (SEQ ID NO: 17) (downstream). The PCR fragment was digested with Spe I and inserted into the compatible Nhe I site of γ42.NheI-S. This generated two plasmids, γ.γb::GFPc3 (positive orientation) and γ.γb.stop.GFPc3-as (negative orientation), with PacI and NotI sites flanking the GFPc3 gene (FIG. 2A). The plasmid γ.γ.b.stop.GFPc3-as, to be used as a negative control, contains a stop codon at the end of the γb ORF to prevent translation of the downstream antisense GFPc3 sequence.

Figure 2B:
FIG. 2B depicts the genetic structure of a RNAγ construct: γ.GFPc3::γb (including the restriction sites for PacI and NotI).

The BSMV γ42.NheI-S cDNA was modified to express GFPc3 as a fusion to the N-terminus of the BSMV γ b protein. A 616 bp fragment, containing the BSMV γb ORF, was amplified from γ42 using PCR and the oligonucleotides 5' TATAGAGCTCTACAAATCTAGAATGGC- TACTTTCTCTTGTGTG 3' (SEQ ID NO: 18) (upstream) and 5' AGAGTCCGTTAAGATTCATGG 3' 3' (SEQ ID NO: 19) (downstream) as primers. The PCR fragment was digested with SacI and PflMI and inserted into the SacI and PflMI sites of γ.Δγb.GFPc3 to generate γ.GFPc3::γb (FIG. 2B).

Inoculation Protocol.

Infectious BSMV RNAs from cDNA clones were prepared by in vitro transcription using T7 DNA-dependent RNA polymerase (Ambion) as described previously (Petty, et al; 1989). Transcripts of each of the BSMV genomes (wild type or genetically modified) were mixed in a 1:1:1 ratio, unless otherwise noted. A 7.5 μl aliquot of the transcription mix was combined with 45 μL of FES (Pogue, et al., 1998) and directly applied to 12 day old black hulless barley, or N. benthamiana plants. Systemic spread was determined by the appearance of mosaic symptoms and by local lesion assay on Chenopodium amranticolor. The presence of heterologous inserts in systemic virus populations was confirmed by Reverse Transcriptase (RT)-PCR using primers specific to the BSMV γ RNA and flanking the inserted cDNA sequence.

Results and Discussion.

In this approach, BSMV was used to expressed GFPc3, as a fusion to the N-terminus of the 675 b protein, in tobacco protoplasts and in systemically infected barley. Previously, GFP had been expressed as a fusion to C-terminus of the γb protein in BSMV (FIG. 1B, Haupt, et al., 2001, Lawrence and Jackson, submitted to Mole. Plant Pathol., on Dec. 20, 2000). However, the γb::GFP fusion was unstable in the virus as it spread systemically.

To improve the stability of the GFP insert we designed a BSMV vector to express GFP as a fusion to the N-terminal of the yb protein (GFPc3::γb). High levels of yb::GFPc3 were expressed systemically by BSMV from the γ RNA of BSMV (FIG. 2A). As mentioned above, systemic expression of the γb::GFPc3 fusion protein has been demonstrated barley (inoculation number 3, Table 1). The fusion of GFPc3 to C-termini of the γb protein resulted in GFPc3 accumulation in barley to levels within 30–50% of that produced by TMV 30B in N. benthamiana (compare inoculation number 2 with 3, Table 1). However, expression is highly variable from plant to plant and RT-PCR experiments using primers flanking the GFP insert revealed that the virus deletes the GFPc3 sequence as it spreads (data not shown). Thus, expression is principally observed in 1–2 leaves above inoculated leaf. In general, the GFPc3 gene is maintained and expressed by the virus for 7–10 dpi, though GFPc3 expression has occasionally been observed up to 25 dpi in the 3rd and 4th leaves above the inoculated leaf (less than 10% of infected plants), or not at all (less than 10% of infected plants).

An alternative site for gene expression is to fuse foreign gene sequences at the N-terminus of γb gene. The fusion of GFPc3 to N-terminus of the γb protein (GFPc3::γb, FIG. 2B) resulted in very high levels of GFPc3 fluorescence and GFPc3::γb accumulation in barley (inoculation number 5, Table 1). However, GFPc3 fluorescence and protein accumulation are observed longer and more consistently in BSMV-GFPc3::γb infected plants than in those infected with BSMV-γ::GFPc3. For example, GFPc3::γb expression is observed in 3–4 leaves above the inoculated leaf by BSMV-GFP::γb, compared to 1–2 leaves for BSMV-γb::GFPc3. Furthermore, the GFPc3 gene is generally maintained and expressed by BSMV::GFPc3::γb to 18 dpi, and can often be observed at 25 dpi in the 5th leaf above the inoculated leaf and in the axillary shoots (about 30% of the infected plants).

In conclusion, our results demonstrate that fusions of heterologous proteins to the BSMV γb protein can be systemically expressed in a monocot, and that fusions to N-terminus of the γb protein are more stable than to the C-terminus.

TABLE 1*

| | Inoculum | | | | | GFP expression | | Mosaic |
|---|---|---|---|---|---|---|---|---|
| Inoc. | Test Constructs | | wt RNAs | | | Tobacco | | Phenotype |
| No. | 1 | 2 | α | β | γ | Protoplasts | Barley Plants | Barley Plants |
| 1 | none | | X | X | X | | | heavy |
| 2 | TMV-SBS5 c3 | | | | | ***** | | |
| 3 | γ.γb::GFPc3 | | X | X | | **** | systemic | heavy |
| 4 | γ.γb::2A::GFPc3 | | X | X | | **** | systemic | heavy |
| 5 | γ.GFPc3::γb | | X | X | | nt | systemic | heavy |
| 6 | γ.GFPc3::2A::γb | | X | X | | nt | systemic | heavy |
| 7 | γ.Δγb | | X | X | | | | light |
| 8 | γ.Δγb.GFPc3 | | X | X | | ** | | |
| 9 | γ.GFPc3.stop.γb | | X | | | nt | | moderate |
| 10 | γ.Δγb.GFPc3 | | X | X | X | *** | | heavy |
| 11 | | β.γb::βb | X | | X | nt | | |
| 12 | γ.Δγb | β.γb::βb | X | | | nt | | |
| 13 | γ.Δγb.GFPc3 | β.γb::βb | X | | | nt | | |
| 14 | | β.γb::mt2A::βb | X | X | | nt | | |
| 15 | γ.Δγb.1 | β.γb::mt2A::βb | X | | | | | |
| 16 | γ.Δγb.GFPc3 | β.γb::mt2A::βb | X | | | ** | | |
| 17 | | β.γb::2A::βb | X | X | | nt | | heavy |
| 18 | γ.Δγb.1 | β.γb::2A::βb | X | | | | | heavy/mod. |
| 19 | γ.Δγb.GFPc3 | β.γb::2A::βb | X | | | ** | | |
| 20 | | β.Δβa | X | X | | | | heavy |
| 21 | γ.γb::GFPc3 | β.Δβa | X | | | ***** | bright systemic | heavy |
| 22 | γ.γb::2A::GFPc3 | β.Δβa | X | | | nt | nt | nt |
| 23 | γ.GFPc3::γb | β.Δβa | X | | | nt | bright systemic | heavy |
| 24 | γ.GFPc3::2A::γb | β.Δβa | X | | | nt | bright systemic | heavy |
| 25 | γ.Δγb.GFPc3 | β.Δβa | X | | | *** | | |
| 26 | γ.Δγb.GFPC3 | β.Δβa | X | X | | **** | | heavy |

TABLE 1*-continued

| | Inoculum | | | | GFP expression | | Mosaic |
|---|---|---|---|---|---|---|---|
| Inoc. | Test Constructs | | wt RNAs | | Tobacco | | Phenotype |
| No. 1 | 2 | α | β | γ | Protoplasts | Barley Plants | Barley Plants |

*Explanation of abbreviation/symbols:
"nt": not tested; under the "Tobacco protoplasts" column (expression is measured against the expression of TMV-SBS5::GFPc3 in tobacco protoplasts):
"*" is 0 to less than 1% (low expression),
"**" is 1 to less than 5% (moderate expression),
"***" is 5 to less than 10% (moderately high expression),
"****" is 10 to less than 100% expression (high expression),
"*****" is 100 to less than 200% (very high expression),
"******" is 200 to less than 500% (very high expression), and
"*******" is 500% or more (very high expression);
under the "Barley Plants" column:
"systemic" is visual detection of systemic GFP expression,
"bright systemic" is visual detection of very bright systemic GFP expression;
under the "Mosaic Phenotype" column:
"light" is about 25% of the plant surface displaying symptomatic tissue,
"moderate" and "heavy/moderate" is about 25–50% of the plant surface displaying symptomatic tissue,
"heavy" is about 50–75% of the plant surface displaying symptomatic tissue.

Example 2
Expression of Native Heterologous Proteins from RNA γ Derived Vectors.
Construction of Monocot Viral Vectors.

Figure 2C:
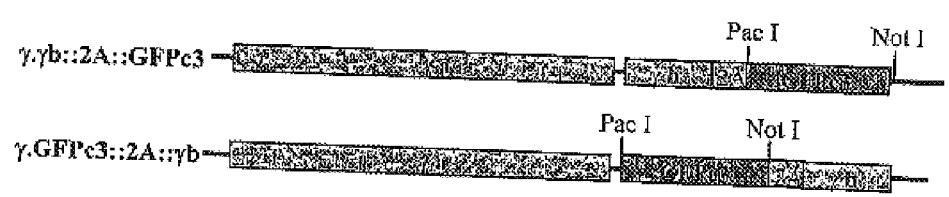
FIG. 2C depicts the genetic structure of two RNAγ constructs: "γ.γb::2A::GFPc3" and "γ.GFPc3::2A::γb" (including the restriction sites for PacI and NotI).

The BSMV vectors expressing N-and C-terminus fusions of GFPc3 to BSMV γb were modified to release GFPc3 after in vivo cleavage of the fusion protein. Cleavage of the fusion protein was achieved by inserting the foot and mouth disease virus (FMDV) 2A autoproteolytic sequence (Ryan, et al., 1991) between the fused ORFs. To construct a vector expressing GFPc3::2A::γb, a 824 bp fragment, containing the GFPc3 ORF, was amplified from the TMV-SBS5::GFPc3 cDNA using PCR and the oligonucleotides 5' CATTAATTAAGATGATGGCTAGCAAAGGAG 3'(SEQ ID NO: 20) (upstream) and 5' ATATCTAGACCTAGGAC-CAGGGTTAGATTCCACGTCACCCGCCAACTTCAGCAAATCAAAATTCAACAGCTGTTTGTA-GAGCTCAGCGGCCGCCTTGTAT AGCTCATCCATG 3' (SEQ ID NO: 21) (downstream) as primers. The PCR fragment was digested with SacI and inserted into γ.GFPc3::γb treated sequentially with SphI, Mung bean nuclease and SacI to generate γ.GFPc3::2A::γb (FIG. 2C). To construct a vector expressing γb::2A::GFPc3, a 818 bp fragment, containing the GFPc3 ORF, was amplified from the TMV-SBS5::GFPc3 cDNA using PCR and the oligonucleotides 5' TATACTAGTCAGCTGT-TGAATTTTGATTTGCTGAAGTTGGCGGGTGACGTG GAATCTAACCCTGGTCCTGTCGACAAAG-GAGAAGAACTTTTCACTGG 3'(SEQ ID NO: 22) (upstream) and 5' TATGCTAGCGATCAATTAGCGGC-CGCTTATTTGTAGAGCTCATCCATGC 3'(SEQ ID NO: 23)(downstream) as primers. The PCR fragment was digested with SpeI and NheI and inserted into the compatible NheI site of BSMV γ42.NheI-S to generate γ.γb::2A::GFPc3 (FIG. 2C).
Inoculation Protocol.
See Example 1.
Results and Discussion.

For many applications it is desirable to produce heterologous proteins in monocot plants that are not fused to virus proteins. For example, many proteins require precise cellular localization to be functional, and fusion of a heterologous protein to a viral protein can prevent proper localization of either the heterologous protein, or the viral protein. In addition, fusion of one protein to another can inhibit activity of either protein due to improper folding or steric interference in a manner which is difficult to predict. To avoid these problems, the FMDV 2A translational cleavage sequence has been inserted into the both of the BSMV vectors described in Example 1, between γb ORF and that of GFPc3 (FIG. 2C). The FMDV 2A cleavage sequence is 90–100% effective in both the N-terminal fusion of GFPc3 to γb (GFPc3::2A::γb) and the C-terminal fusion (γb::2A::GFPc3) as judged by Western analysis of product from infected tobacco protoplasts and barley plants (data not shown). Viral spread and GFPc3 fluorescence in barley plants infected with BSMV-GFPc3::2A::γb are indistinguishable from those containing BSMV-GFPc3::γb. In contrast, the systemic spread of the BSMV-γb::2A::GFPc3 virus is slightly delayed compared to BSMV-γb::GFPc3. Both BSMV-γb::2A::GFPc3 and BSMV-GFPc3::2A::γb are able to infect and express GFPc3 in N. benthamiana plants in a manner similar to that reported for BSMV-γb::GFP (Lawrence and Jackson, submitted to Mole. Plant Pathol., submitted on Dec. 20, 2000).

Example 3
Expression of Epitope Tagged Heterologous Proteins from RNA γ Derived Vectors.
Construction of Monocot Viral Vectors.

Figure 2D:
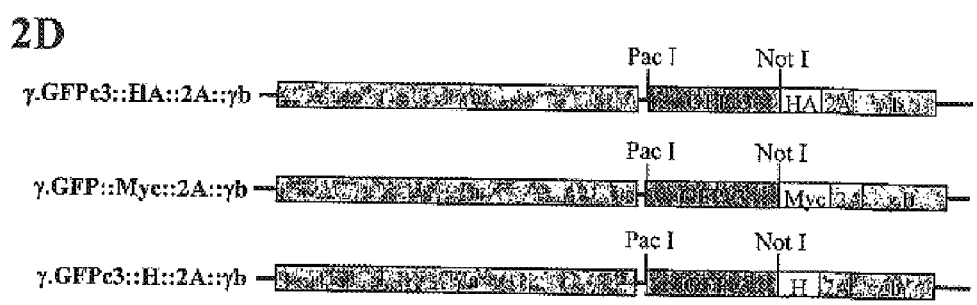
FIG. 2D depicts the genetic structure of three RNAγ constructs: "γγGFPc3::HA::2A::γb", "γ.GFPC3:myc::2A::γb", and "γ.GFPc3::H::2A::γb" (including the restriction sites for PacI and NotI).

The BSMV vector γ.GFPc3::2A::γb was modified to express epitope tagged GFPc3 fused to the N-terminus of the FMDV 2A cleavage sequence and BSMV γb protein. Epitope tagging of GFPc3 was achieved by inserting either the hemagglutinin (HA), c-Myc epitope, or 9x poly-histidine epitope tag between GFPc3 ORF and the FMDV 2A/BSMV γb fusion ORF. To construct a vector expressing GFPc3::HA::2A::γb, a linker consisting of the oligonucleotides 5' GGCCGCTTATCCGTATGATGTTCCGGAT-TATGCCGAGCT 3' (SEQ ID NO: 24)(and 5' CGGCAT-AATCCGGAACATCATACGGATAAGC 3' (SEQ ID NO: 25) was inserted into the NotI and SacI sites of γ.GFPc3::2A::γb, generating γ.GFPc3::HA::2A::γb (FIG. 2D). To construct a vector expressing GFPc3::Myc::2A::γb, a linker consisting of the oligonucleotides 5' GGCCGCT-GAACAAAAGCTTATCTCTGAGGAAGATCTTGAGCT 3' (SEQ ID NO: 26) and 5' CAAGATCTTCCTCA-GAGATAAGCTTTTGTTCAGC 3' 3' (SEQ ID NO: 27) was inserted into the NotI and SacI sites of γ.GFPc3::2A::γb, generating γ.GFPc3::Myc::2A::γb (FIG. 2D). To construct a vector expressing GFPc3::H::2A::γb, a linker consisting of the oligonucleotides 5' GGCCGCTCATCATCACCATCAC-CATCACCATCACGAGCT 3' (SEQ ID NO: 28) and 5' CGTGATGGTGATGGTGATGGTGATGATGAGC 3' (SEQ ID NO: 29) was inserted into the NotI and SacI sites of γ.GFPc3::2A::γb, generating γ.GFPc3::H::2A::γb (FIG. 2D).

The BSMV vector γ.GFPc3::H::2A::γb was modified to express five selected proteins as poly-histidine tagged fusions to the N-terminus of the FMDV 2A cleavage sequence and BSMV γb protein. To construct a vector expressing the brome mosaic virus coat protein (BMV-CP, Ahlquist, et al., 1981), the oligonucleotides 5' TATTTAAT-TAAGATGTCGACTTCAGGAACTGG 3' (SEQ ID NO: 30) (upstream) and 5' TATGCGGCCGC-CCTATAAAGCGGGGTGAAG 3' (SEQ ID NO: 31) (downstream) were used to amplify a 593 bp fragment from 30B-BMVcp 1. This fragment, containing the BMV cp ORF, was digested with PacI and NotI and inserted between the PacI and NotI sites of γ.GFPc3::H::2A::γb, replacing the GFPc3 ORF and generating γ.BMCcp::H::2A::γb. To construct a vector expressing chicken interferon (chIF, Digby and Lowenthal, 1995), the oligonucleotides 5' TATTTAAT-TAAGATGACTTGCCAGACTTACAAC 3' (SEQ ID NO: 32) (upstream) and 5' TATGCGGCCGCGCAATTG-CATCTCCTCTGAG 3' (SEQ ID NO: 33) (downstream) were used to amplify a 518 bp fragment from 30B-chINF. This fragment, containing the chIF ORF, was digested with PacI and NotI and inserted between the PacI and NotI sites of γ.GFPc3::H::2A::γb, replacing the GFPc3 ORF and generating γ.chIF::H::2A::γb. To construct a vector expressing bovine lysozyme (boLys, Irwin and Wilson, 1989), the oligonucleotides 5' TATTTAATTAAGATGAAG-GCTCTCGTTATTCTGG 3' (SEQ ID NO: 34) (upstream) and 5' TATGCGGCCGCCAGGGTGCAACCCTCAACG 3' (SEQ ID NO: 35) (downstream) were used to amplify a 467 bp fragment from 735 bolys. This fragment, containing the boLys ORF, was digested with PacI and NotI and inserted between the PacI and NotI sites of γ.GFPc3::H::2A::γb, replacing the GFPc3 ORF and generating γ.boLys::H::2A::γb. To construct a vector expressing human growth hormone (hGH, DeNoto, et al., 1981), the oligonucleotides 5' TATTTAATTAAGATGGGAAAAATGGCT-TCTCTATTTGC 3' (SEQ ID NO: 36) (upstream) and 5' TATGCGGCCGCGAAACCGCAGGGAACCTTCAACG 3' (SEQ ID NO: 37) (downstream) were used to amplify a 677 bp fragment from 30B-(HCPRO)-hGH. This fragment, containing the hGH ORF, was digested with PacI and NotI and inserted between the PacI and NotI sites of γ.GFPc3::H::2A::γb, replacing the GFPc3 ORF and generating γ.hGH::H::2A::γb. To construct a vector expressing tomato protease inhibitor 1 (tPI1, Graham, et al, 1985), the oligonucleotides 5' TATTTAATTAAGATGGAGT-CAAAGTTTGCTCAC 3' (SEQ ID NO: 38) (upstream) and 5' TATGCGGCCGCAGTCACCACAGGCATTTGTAC 3' (SEQ ID NO: 39) (downstream) were used to amplify a 359 bp fragment from 735-tomPI 3. This fragment, containing the tPI1 ORF, was digested with PacI and NotI and inserted between the PacI and NotI sites of γ.GFPc3::H::2A::γb, replacing the GFPc3 ORF and generating γ.tPI::H::2A::γb.

Inoculation Protocol.

See Example 1.

Results and Discussion.

Many applications require the ability to detect and be able to isolate a protein. Epitope tags provide a convenient method for both detection and purification of proteins because they are small protein sequences that are recognized by commercially available antibodies (Jarvik and Telmer, 1998). To detect heterologous proteins expressed by the BSMV vector in Example 2, epitope tags were inserted between GFPc3 and the 2A sequence of the GFP::2A::γb fusion to generate three different vectors (FIG. 2D). Each epitope tagged GFPc3 was analyzed by Western blotting and probed with the available antibodies. Both the anti-HA (anti-hemagglutinin, Y-11 and F-7 Santa Cruz Biotechnology, Santa Cruz, Calif.) and anti-Myc (anti c-Myc, A-14 and 9E10, Santa Cruz Biotechnology, Santa Cruz, Calif.) antibodies were able to efficiently detect their respective tags when compared to the anti-GFP antibody. However, the H (poly-histidine) tag was only weakly recognized by the anti-histidine antibody (H-15, Santa Cruz Biotechnology, Santa Cruz, Calif.). The addition of coding sequences for the HA and Myc peptide tags will allow the efficient detection of expression of non-processed proteins expressed from virus vectors. The only exception would be for a subset of vacuolar proteins that are proteolytically processed to remove a C-terminal vacuolar sorting sequence (VSS) (reviewed in Chrispeels and Raikhel, *Plant Physiol.* 122:1–2 (2000)).

Figure 3A:
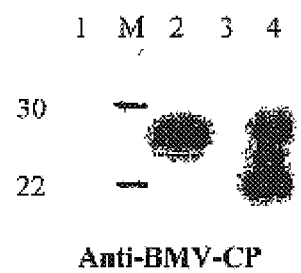
FIG. 3A depicts the Western blot analysis of protein extracted from barley or N. benthamiana infected with recombinant BSMV or recombinant TMV probed with an anti-BMV coat protein antibody. Lane M contains the marker. Lane 1 contains protein extracted from barley infected with the α, βΔβa, γ.GFPc3::H::2A::γb recombinant BSMV. Lane 2 contains protein extracted from barley infected with the α, βΔβa, γ.BMV-CP::H::2A::γb recombinant BSMV. Lane 3 contains protein extracted from N. benthamiana infected with the TMV SBS5::GFP recombinant TMV. Lane 4 contains protein extracted from N. benthamiana infected with the TMV SBS5::BMV-CP recombinant TMV.
Figure 3B:
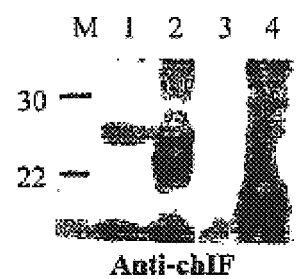
FIG. 3B depicts the Western blot analysis of protein extracted from barley or N. benthamiana infected with recombinant BSMV or recombinant TMV probed with an anti-chicken interferon (chIF) antibody. Lane M contains the marker. Lane 1 contains protein extracted from barley infected with the α, βΔβa, γ.GFPc3::H::2A::γb recombinant BSMV. Lane 2 contains protein extracted from barley infected with the α, βΔβa, γ.chIF::H::2A::γb recombinant BSMV. Lane 3 contains protein extracted from N. benthamiana infected with the TMV SBS5::GFP recombinant TMV. Lane 4 contains protein extracted from N. benthamiana infected with the TMV SBS5::chIF recombinant TMV.
Figure 3C:
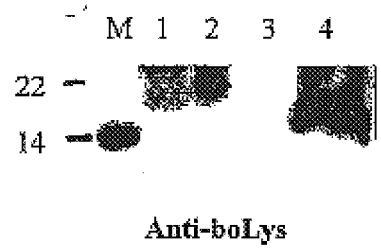
FIG. 3C depicts the Western blot analysis of protein extracted from barley or N. benthamiana infected with recombinant BSMV or recombinant TMV probed with an anti-bovine lysozyme (boLys) antibody. Lane M contains the marker. Lane 1 contains protein extracted from barley infected with the α, βΔβa, γ.GFPc3::H::2A::γb recombinant BSMV. Lane 2 contains protein extracted from barley infected with the α, βΔβa, γ.boLys::H::2A::γb recombinant BSMV. Lane 3 contains protein extracted from N. benthamiana infected with the TMV SBS5::GFP recombinant TMV. Lane 4 contains protein extracted from N. benthamiana infected with the TMV SBS5::boLys recombinant TMV.
Figure 3D:
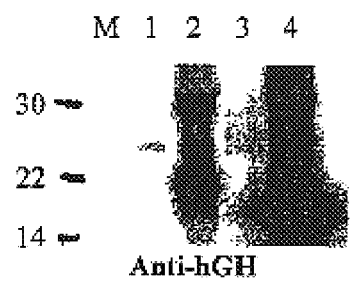
FIG. 3D depicts the Western blot analysis of protein extracted from barley or N. benthamiana infected with recombinant BSMV or recombinant TMV probed with an anti-human growth hormone (hGH) antibody. Lane M contains the marker. Lane 1 contains protein extracted from barley infected with the α, βΔβa, γ.GFPc3::H::2A::γb recombinant BSMV. Lane 2 contains protein extracted from barley infected with the α, βΔβa, γ.hGH::H::2A::γb recombinant BSMV. Lane 3 contains protein extracted from N. benthamiana infected with the TMV SBS5::GFP recombinant TMV. Lane 4 contains protein extracted from N. benthamiana infected with the TMV SBS5::hGH recombinant TMV.
Figure 3E:
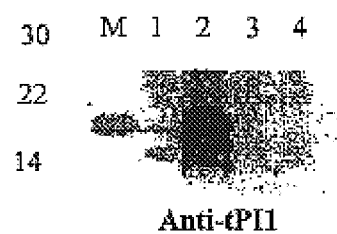
FIG. 3E depicts the Western blot analysis of protein extracted from barley or N. benthamiana infected with recombinant BSMV or recombinant TMV probed with an anti-tomato protease inhibitor (tPI1) antibody. Lane M contains the marker. Lane 1 contains protein extracted from barley infected with the α, βΔβa, γ.GFPc3::H::2A::γb recombinant BSMV. Lane 2 contains protein extracted from barley infected with the α, βΔβa, γ.t.PI1::H::2A::γb recombinant BSMV. Lane 3 contains protein extracted from N. benthamiana infected with the TMV SBS5::GFP recombinant TMV. Lane 4 contains protein extracted from N. benthamiana infected with the TMV SBS5::tPI1 recombinant TMV.

Five proteins besides GFPc3 were expressed as N-terminal fusions to H::2A::γb (FIG. 2D). For each protein expressed, systemically infected tissue was harvested at 6 dpi and compared to local leaves from *N. benthamiana* infected with TMV expressing the same protein. Crude protein extracts were subjected to Western blotting using cognate antibodies raised against the heterologous protein of interest (FIG. 3A–E). Since the H epitope tag and the 2A sequence remain on the heterologous protein following cleavage from γb, these proteins are 4 kD larger when expressed by BSMV than those expressed by the TMV vector. In each case, the size of the protein detected in the western blot was consistent with the size predicted for the post-cleavage heterologous protein. The brome mosaic virus coat protein (BMV-CP, Ahlquist, et al., 1981) and chicken interferon (chIF, Digby and Lowenthal, 1995) expressed from BSMV accumulated to about 75% that of a TMV vector in *N. benthamiana* (FIG. 3A, 3B). Bovine lysozyme (boLys, Irwin and Wilson, 1989), human growth hormone (hGH, DeNoto, et al., 1981), and tomato protease inhibitor 1 (tPI1, ref) were also expressed successfully from BSMV, though at apparently lower levels, relative to a TMV in *N. benthamiana* (FIG. 3C–E).

Four of the proteins, bovine lysozyme, chicken interferon, human growth hormone, and protease inhibitor, contain N-terminal signal peptides (SP) which target the proteins to the endoplasmic reticulum (ER) while they are translated by the ribosome. For proteins targeted to the ER, the SP is removed, and the remainder of the protein is transported to its ultimate destination. In the case of bovine lysozyme, chicken interferon, human growth hormone and protease inhibitor, this destination is lysozyme, chicken interferon, human growth hormone and protease inhibitor, this destination is the apoplast. The 2A autoproteolytic peptide allows these protiens to reach their normal destination without interefering with the cytoplasmic destination of the γb protein to which they are fused. This occurs because 2A mediated cleavage occurs cotranslationally (Ryan, et al., 1999), after allowing the N-terminal, ER targeted protein to enter the ER, but before the γb is targeted. Expression of bovine lysozyme, chicken interferon, human growth hormone, and protease inhibitor by BSMV as 2A fusions to the N-terminal of γb produces proteins of the size expected after ER targeting and removal of the SP (FIGS. 3B–E).

Since the viruses expressing these proteins are as infectious as the wild-type virus, it can be inferred that the γb protein is being cytoplasmically targeted.

The flexibility of the BSMV expression vector to successfully express proteins of cytosolic localization (GFP and BMV coat protein) and those that are matured through the plant secretory pathway (bovine lysozyme, chicken interferon, human growth hormone and protease inhibitor). These data also demonstrate the ability of the vector to express genes of both plant and animal sources successfully.

Example 4
Heterologous Protein Substitution of BSMV γb ORF.
Construction of Monocot Viral Vectors.

Figure 2E:
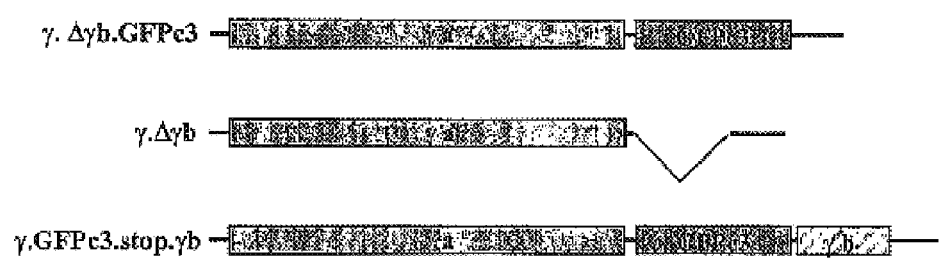
FIG. 2E depicts the genetic structure of three RNAγ constructs: "γ.Δγb.GFPc3", "γ.Δγb", and "γ.GFPc3.stop.γb".
Figure 5A:
FIG. 5A depicts the genetic structure of the RNAγ construct: "γ.Δa.Δγb.GFPc3" (including the restriction sites for EcoRV).
Figure 5B:
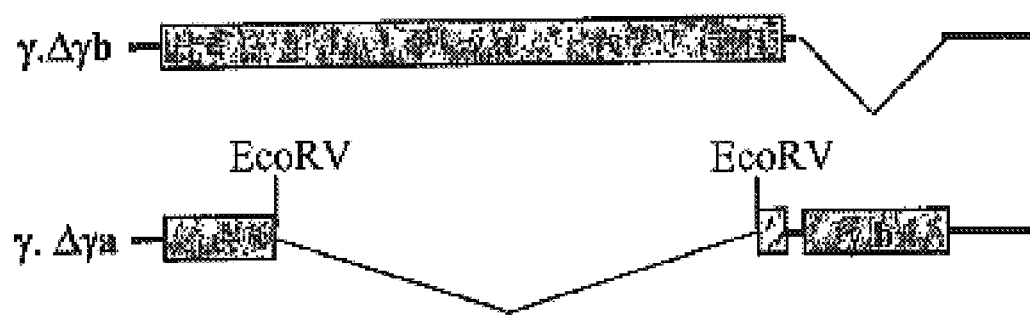
FIG. 5B depicts the genetic structure of two RNAγ constructs: "γ.Δγb" and "γ.Δγa" (including the restriction sites for EcoRV).
Figure 5C:
FIG. 5C depicts the genetic structure of the RNAγ construct: "γ.Δγb.GFPc3".

The BSMV γ42.NheI-S cDNA was modified to express GFPc3 in place of the BSMV γb protein. First, the γb ORF was removed by using PCR mutagenesis. Oligonucleotides 5' ATAGATATCGATCCCCTTATAGTGC 3' (SEQ ID NO: 40) (upstream) and 5' ATAGCTAGCAAGCATGCGAAGG-TAAATACAGTAG 3' (SEQ ID NO: 41) (downstream) were used to amplify a 200 bp fragment from γ42, containing the 185 nucleotides immediately upstream of the γb ORF followed by a modified start codon containing an Sph I restriction site. This PCR fragment was digested with EcoRV and NheI and inserted between the downstream EcoRV site and the NheI site of BSMV γ42.NheI-S cDNA to generate γ.Δγb (FIG. 2E, 5B). Subsequently, GFPc3 was amplified from 30B::GFPc3 using the oligonucleotides 5' TATACTAGTTTAATTAAGTCGACCATG-GCTAGCAAAGGAGAAGAAC 3' (SEQ ID NO: 42) (upstream) and 5' TATTCTAGATGAGCGGCCGCT-TATTTGTAGAGCTCATCCATGCC 3' (SEQ ID NO: 43) (downstream). The PCR fragment was digested with NheI and XbaI and inserted into the compatible NheI site of γ.Δγb to generate γ.Δγb.GFPc3 (FIG. 2E, 5C).

The BSMV γ42.NheI-S cDNA was modified to express GFPc3 from the γb subgenomic RNA but without expression of the γb ORF. A 619 bp fragment, containing the BSMV γb ORF, was amplified from γ42 using PCR and the oligonucleotides 5' TATAGAGCTCTACAAATAATCTAGAATG-GCTACTTTCTCTTGTGTG 3' (SEQ ID NO: 44) (upstream) and 5' AGAGTCCGTTAAGATTCATGG 3' (SEQ ID NO: 45) (downstream) as primers. The PCR fragment was digested with SacI and PflMI and inserted into the SacI and PflMI sites of γ.Δγb.GFPc3 to generate γ.GFPc3.stop.γb (FIG. 2E). γ.GFPc3.stop.γb has a stop codon at the end of the GFPc3 ORF that prevents the γb ORF from being translated.

Figure 4A:
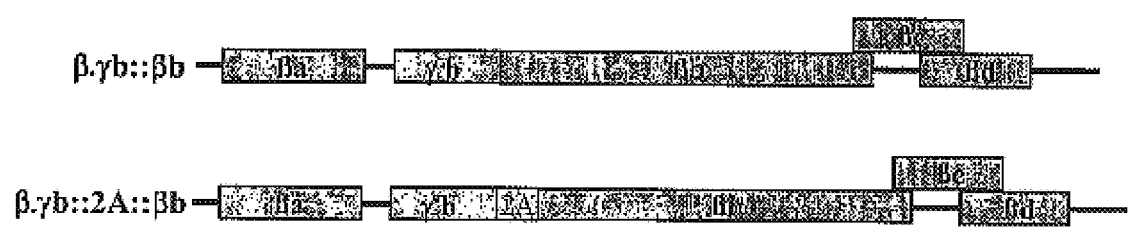
FIG. 4A depicts the genetic structure of two RNAβ constructs: "β.γb::βb" and "β.γb::2A::βb".

The BSMV β42SpI cDNA was modified to express the BSMV γb protein as an N-terminal fusion to the βb protein. A 487 bp fragment, containing the BSMV γb ORF, was amplified from BSMV γ42 using PCR and the oligonucleotides 5' ATATAGGTCTCCCATGATGGC-TACTTTCTCTTGTG 3' (SEQ ID NO: 46) (upstream) and 5' TATTAGGTCTCCCATGGCCTTAGAAACG-GAAGAAGAATC 3' (SEQ ID NO: 47) (downstream) as primers. The PCR fragment was digested with BsaI and inserted into the compatible NcoI site of β42SpI to generate β.γb::βb (FIG. 4A).

The BSMV β RNA vector expressing the BSMV γb protein as an N-terminal fusion to the βb protein was modified to release γb after in vivo cleavage of the fusion protein. Cleavage of the fusion protein was achieved by inserting the FMDV 2A autoproteolytic sequence between the fused ORFs. A 547 bp fragment, containing the BSMV γb ORF, was amplified from γ.γb::2A::GFPc3 using PCR and the oligonucleotides 5' ATATAGGTCTCCCATGATG-GCTACTTTCTCTTGTG 3' (SEQ ID NO: 48) (upstream) and 5' TATTAGGTCTCCCATGGCAGGAC-CAGGGTTAGATTCC 3' (SEQ ID NO: 49) (downstream) as primers. The PCR fragment was digested with BsaI and inserted into the compatible Nco I site of β42SpI to generate β.γb::2A::βb (FIG. 4A).
Inoculation Protocol.
See Example 1.
Results and Discussion.

Another strategy to produce heterologous proteins without fusion to viral proteins was to replace the γb ORF with that of the heterologous ORF. Substitution of the GFPc3 ORF for the γb ORF (FIG. 2E) resulted in moderate GFPc3 expression in protoplasts, but the virus was not detected, and GFPc3 was not observed, in planta (inoculation number 8, Table 1). The lack of systemic movement of the γ.Δγb.GFPc3 virus was unexpected, since viruses bearing γb deletions (γ.Δγb, FIG. 2E) are capable of systemic spread, albeit more slowly than wild type BSMV (Petty, et al., 1990, inoculation number 7, Table 1). There is evidence that RNA sequences within γb may boost infectivity (Zhou, et al., 1996). Inserting all of the deleted γb sequence as an untranslated ORF downstream of the GFPc3 gene (FIG. 2E) partially restored infectivity to the virus with γb, but did not confer systemic GFPc3 expression in barley plants (inoculation number 9, Table 1).

The results of several protoplast inoculations suggested that the γb substitution vector might produce more GFPc3, and also be systemically infectious, if the γb function were complemented in a three component system. For example, if the γb replacement vector was inoculated with the wt γ RNA as a fourth component GFPc3 accumulation in protoplasts increased 2–5 fold over the three component system (compare inoculation number 8 with 10 and 33 with 34, Table 1). However, neither of these four component systems expressed GFPc3 systemically in barley, apparently due to the loss of the GFPc3 bearing component during systemic movement. Therefore, to achieve γb complementation in a three component system, γb was fused (with and without the 2A sequence) to the N-terminal of the βb protein on the β RNA (FIG. 4A). In addition, β.γb.mt2A.b, a construct with a mutation in the 2A site which prevents cleavage of the fusion protein, was also tested. Without a functional 2A site between the γb::βb fusion, βb activity is lost and the virus is not systemically infectious (inoculation number 11–16, Table 1). When the functional 2A sequence was included between γb and βb, βb and γb were both functional and the virus could move systemic (inoculation number 17 and 18, Table 1), but not with a γ RNA bearing the GFPc3 substitution of the γb ORF (inoculation number 19, Table 1).

Example 5
Effect of Coat Protein Deletion Heterologous Protein Expression from RNA γ Derived Vectors.
Construction of Monocot Viral Vectors.

Figure 4B:
FIG. 4B depicts the genetic structure of the RNAβ construct: "β.Δβa" (including the restriction site for BstBI).

To improve the expression of the γ subgenomic RNA1, an infectious BSMV RNA beta (β) cDNA (β42SpI) (Petty, et al; 1989) was modified by deleting the majority of the coat protein ORF by PCR mutagenesis. To generate the deletion, a 423 bp fragment was amplified from β42SpI using the oligonucleotides 5' GGAAAGCCGGCGAACGTGGCG 3' (SEQ ID NO: 50) (upstream) and 5' TATATTCGAATCTA-GAATCGATGCTAGCTTGCATGCTGT-GAAGTGGTAAAA GAAATGC 3' (SEQ ID NO: 51) (downstream) and cloned into the NgoMIV and BstBI sites of β42SpI, creating plasmid β.Δβa (FIG. 4B). This construct contains only an untranslatable portion of the coat protein ORF that is required for expression of the subsequent β RNA ORFs.

Inoculation Protocol.
  See Example 1.
Results and Discussion.
  The coat protein (βa) of BSMV is not required for systemic infection. To determine the impact of βa deletion on γb expression, a β genomic RNA containing a deletion of the βa ORF was constructed (β.Δβa, FIG. 4B). In tobacco protoplasts, using β.Δβa increased GFPc3 accumulation 5 to 10 fold for viruses bearing either the γb::GFPc3 fusion or GFPc3 substitution of γb (compare inoculation number 3 with 21, 8 with 25, and 10 with 26, Table 1). Using β.Δβa also increased GFPc3 accumulation for γb::GFPc3, GFPc3::γb, and GFPc3::2A::γb, in systemic barley tissue (compare inoculation number 3 with 21, 5 with 23, and 6 with 23, Table 1).

Figure 4C:
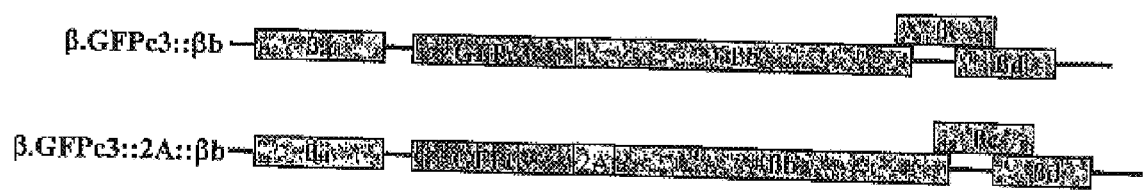
FIG. 4C depicts the genetic structure of two RNAβ constructs: "β.GFPc3::βb" and "β.GFPc3::2A::βb".

Example 6
Expression of Heterologous Proteins from BSMV RNA β.
Construction of Viral Vectors.
  The BSMV β42SpI cDNA was modified to express GFPc3 as an N-terminal fusion to the βb protein. A 757 bp fragment, containing the GFPc3 ORF, was amplified from the TMV-SBS5::GFPc3 cDNA using PCR and the oligonucleotides 5' ATATAGGTCTCCCATGGCTAGCAAAG-GAGAAGAAC 3' (SEQ ID NO: 52) (upstream) and 5' TATTAGGTCTCACATGCATGCTCTA-GATTTGTAGAGCTCATCCATGCC 3' (SEQ ID NO: 53) (downstream) as primers. The PCR fragment was digested with BsaI and inserted into the compatible NcoI site of β42SpI to generate β.GFPc3::βb (FIG. 4C).
  The BSMV β RNA vector expressing GFPc3 as an N-terminal fusion to the βb protein was modified to release GFPc3 after in vivo cleavage of the fusion protein. Cleavage of the fusion protein was achieved by inserting the FMDV 2A autoproteolytic sequence between the fused ORFs. An 809 bp fragment, containing the GFPc3 ORF, was amplified from the TMV-SBS5::GFPc3 cDNA using PCR and the oligonucleotides 5' ATATAGGTCTCCCATGGCTAG-CAAAGGAGAAGAAC 3' (SEQ ID NO: 54) (upstream) and 5' TTAGGTCTCACATGTCTAGAGGAC-CAGGGTTAGATTCCACGTCACCCGCC AACTTCAG-CAAATCAAAATTCAACAGCTGTTTGTA-GAGCTCATCCATGCC 3' (SEQ ID NO: 55) (downstream) as primers. The PCR fragment was digested with BsaI and inserted into the compatible NcoI site of β42SpI to generate β.GFPc3::2A::βb (FIG. 4C).
Inoculation Protocol.
  See Example 1.
Results and Discussion.
  In this strategy, genetic modifications made to the BSMV β RNA allow it to express the green fluorescent protein (GFP) during infections with the other BSMV genomic RNAs, α and γ, in the monocot host, barley. Moderate, to high, levels of GFPc3 were expressed systemically by BSMV from the β RNA of BSMV as a fusion to the N-terminal of the βb protein (FIG. 4C). The fusion of GFPc3 to the N-terminal of the βb resulted in GFPc3 accumulation in barley to levels within 30–50% of that produced by TMV 30B in N. benthamiana. This is similar to the amount of GFPc3 produced by the γb::GFP fusion (compare inoculation number 3 and 5, Table 2). The extensiveness of GFPc3 expression was improved by 2A-mediated cleavage and release from the GFPc3::2A::βb fusion protein (FIG. 4C, inoculation number 6, Table 2) but not by a similar virus with a mutation that deactivates the 2A activity (inoculation number 7, Table 2). Although the GFPc3 gene can be maintained by the GFPc3:: βb or GFPc3::2A::βb viruses to 14 dpi, both viruses move more slowly than GFPc3 fusions to γb. Therefore, the net duration and extent of systemic GFPc3 expression by GFP::Pb and GFP::2A:: b is somewhat less that of the γb fusions. These results suggest that a BSMV vector based on heterologous protein fusions to the N-terminal of the βb (inoculation number 6, Table 2) and γb (inoculation number 24, Table 1) may be useful for the expression of two or more genes simultaneously in systemic barley tissue.
  Both the GFP::Pb or GFP::2A::βb viruses expressed 100–500 fold lower amounts of GFPc3 in infected tobacco protoplasts relative to GFPc3 fusions to γb, even though the two groups accumulated similar levels in barley plants (compare inoculations number 5–7 with 3 Table 2). This discrepancy between the performances of βb fusions in plants vs. protoplasts may reflect differences in βb subgenomic promoter activity. Whether this discrepancy is due to the behavior of protoplasts vs, plant tissue is unclear or effect of host specific factors (barley vs. tobacco) is not known.

TABLE 2*

| | Inoculum | | | | | GFP expression | | Mosaic |
|---|---|---|---|---|---|---|---|---|
| | Test Constructs | | wt RNAs | | | Tobacco | Barley | Barley |
| # | 1 | 2 | α | β | γ | Protos | Plants | Plants |
| 1 | none | | X | X | X | | | heavy |
| 2 | TMV-SBS5 GFPc3 | | | | | ***** | | |
| 3 | γ.γb.GFPc3 | | X | X | | **** | systemic | heavy |
| 4 | γ.γb.GFPc3 | β.Δβa | X | | | ***** | bright systemic | heavy |
| 5 | β.GFPc3::βb | | X | | X | * | systemic | light |
| 6 | β.GFPc3::2A::βb | | X | | X | * | systemic | moderate |
| 7 | β.GFPc3::mt2A::βb | | X | | X | * | systemic | light |
| 8 | | β.c3.Δβb | X | | X | ** | | |
| 9 | γ.γb::2A::βb | | X | X | | nt | | light |
| 10 | γ.γb::2A::βb | β.c3.Δβb | X | | | nt | | light |
| 11 | γ.γb::βb | | X | X | | nt | nt | nt |
| 12 | γ.γb::βb | β.c3.Δβb | X | | | nt | | |
| 13 | | β.γb::2A::βb | X | | X | nt | | heavy |
| 14 | | β.γb:βb | X | | X | nt | | |
| 15 | γ.GFPc3::γb | | X | X | | nt | systemic | heavy |

*See Table 1 for explanation of abbreviation/symbols.

Example 7
Expression of Heterologous Proteins from BSMV RNA β.
Construction of Viral Vectors.

Figure 4D:
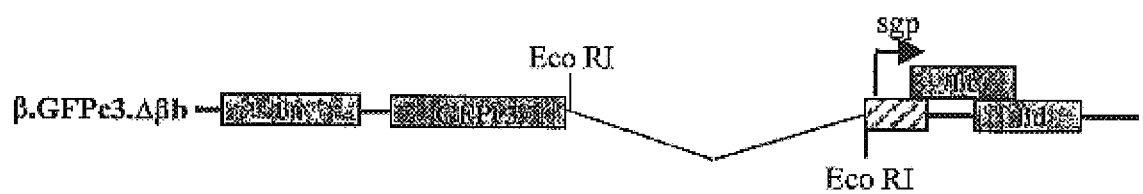
FIG. 4D depicts the genetic structure of the RNAβ construct: "β.GFPc3.Δb" (including the restriction sites for EcoRI).

The BSMV β42SpI cDNA was modified to express GFPc3 as a replacement for the βb protein. A 750 bp fragment, containing the GFPc3 ORF, was amplified from the TMV-SBS5::GFPc3 cDNA using PCR and the oligonucleotides 5' ATATAGGTCTCCCATGGCTAGCAAAG-GAGAAGAAC 3' (SEQ ID NO: 56) (upstream) and 5' TATTAGAATTCTCTAGATTATTTGTA-GAGCTCATCCATGCC 3' (SEQ ID NO: 57) (downstream) as primers. The PCR fragment was digested with BsaI and Eco RI, and inserted between the BsaI and EcoRI sites of β42SpI to generate β.GFPc3.Δβb (FIG. 4D).

Figure 4E:
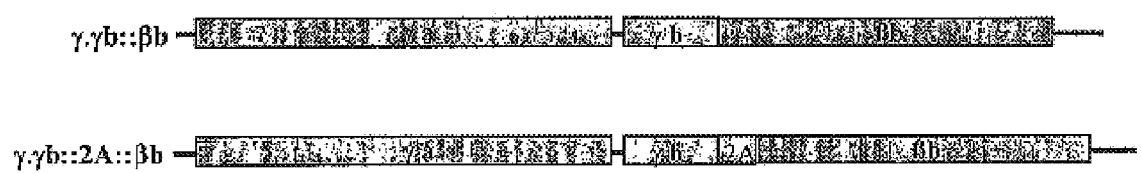
FIG. 4E depicts the genetic structure of two RNAγ constructs: "γ.γb::βb" and "γ.γb::2A::βb".

The BSMV γ42.NheI-S cDNA was modified to express the βb protein as a fusion to the C-terminus of the BSMV γb protein, both with and without the FMDV 2A cleavage sequence. Using PCR mutagenesis, a 1557 bp fragment, containing the βb protein ORF, was amplified from β42SpI using the oligonucleotides 5' 5 TATACTAGTATGGACAT-GACGAAAACTGTTG 3' (SEQ ID NO: 58) (upstream) and 5' TATGCTAGCTTATTTGGCCTTGAACCAACTG 3' (SEQ ID NO: 59) (downstream). The PCR fragment was digested with NheI and SpeI and inserted into the compatible NheI site of γ42.NheI-S to generate γ.γb::βb (FIG. 4E). Using PCR mutagenesis, a 1623 bp fragment, containing the 2A::βb protein ORF, was amplified from βGFPc3::2A::βb using the oligonucleotides 5' TATACTAGTCAGCTGT-TGAATTTTGATTTGC 3' (SEQ ID NO: 60) (upstream) and 5' TATGCTAGCTTATTTGGCCTTGAACCAACTG 3' (SEQ ID NO: 59) (downstream). The PCR fragment was digested with NheI and SpeI and inserted into the compatible NheI site of γ42.NheI-S to generate γ.γb::2A::βb (FIG. 4E).

Inoculation Protocol.
See Example 1.
Results and Discussion.

Another strategy to produce heterologous proteins that are not fused to virus proteins was to replace the βb ORF with that of the heterologous gene. Substitution of the GFPc3 gene for the βb gene (FIG. 4D) resulted in low to moderate GFPc3 expression in protoplasts (inoculation number 8, Table 2). However, due to the lack of the βb gene, a required movement protein, these viruses were not infectious and GFPc3 was not observed in planta. Therefore, to complement the lost movement function, βb was fused to the C-terminus of the γb protein, either with or without the 2A cleavage sequence (FIG. 4E). Although γb::2A::Pb (inoculation number 10, Table 2) was able to restore movement, it was only weakly infectious and did not confer systemic expression of GFP. It is possible that a βb::2A::γb fusion would be 30 more robust, but this has not been constructed or tested. If successful, this would provide another opportunity for systemic expression of two heterologous proteins simultaneously in barley.

Unlike the γ.γb::2A::βb virus, the virus expressing the γb::βb fusion from the γ RNA did not complement the βb deletion (inoculation number 12, Table 2). This suggests that the fusion of γb to the N-terminal of βb inactivates βb. The interference of γb with βb when fused is supported by a comparison of the γb::2A::βb and γb::βb fusions on the β RNA (inoculation number 13 and 14, Table 2), in which the 2A sequence is also required for systemic infection. This effect appears to be specific to the γb protein as GFPc3 did not interfere with β activity when the GFPc3::βb fusion was expressed from the β RNA (inoculation number 15, Table 2).

Example 8
Expression of Heterologous Proteins from Four-Component BSMV Based on RNA γ.
Construction of Viral Vectors.

To generate the plasmid γ.ΔγaΔγb.GFPc3 (FIG. 5A), γ.Δγb.GFPc3 was digested with EcoRV and religated to remove the 1306 bp EcoRV fragment in the γa ORF. To generate the plasmid γ.Δγa (FIG. 5B), γ.42 was digested with EcoRV and religated to remove the 1306 bp EcoRV fragment in the γa ORF.

Inoculation Protocol.
See Example 1.
Results and Discussion.

To express heterologous proteins without fusion to viral proteins, two novel four component strategies, with duplicated γ RNAs, were employed. Genetic modifications to the fourth BSMV γ RNA allowed the expression of GFPc3 during co-infections with BSMV α, β, and γ RNAs.

Figure 5D:
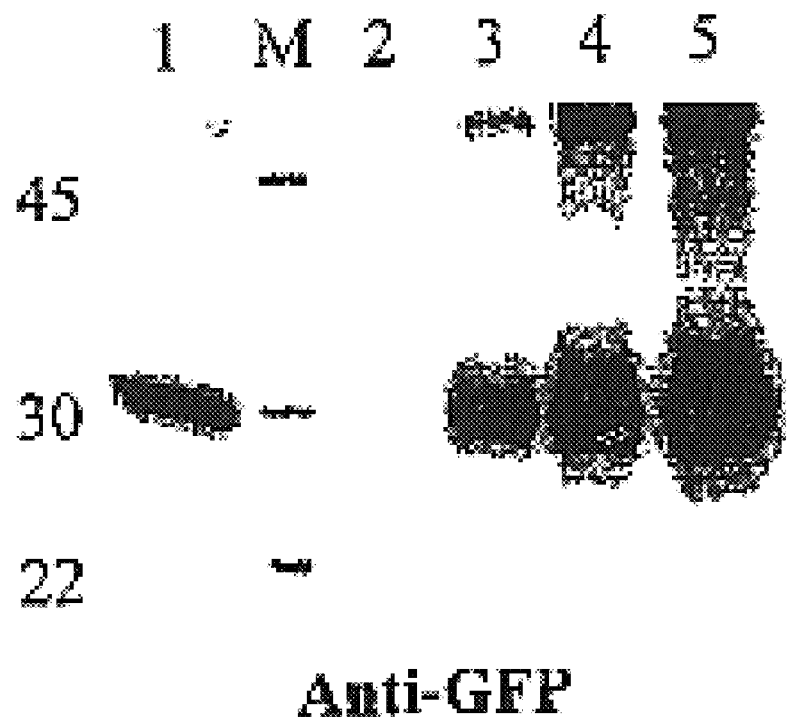
FIG. 5D depicts the Western blot analysis of protein extracted from tobacco protoplasts infected with recombinant BSMV or recombinant TMV probed with an anti-GFP antibody. Lane M contains the marker. Lane 1 contains protein extracted from tobacco protoplasts infected with the TMV SBS5::GFP recombinant TMV (inoculation number 2, see Table 3). Lane 2 contains protein extracted from tobacco protoplasts infected with the α, β, γ.Δγa.Δa.b.GFPc3 recombinant tobacco (inoculation number 5, see Table 3). Lane 3 contains protein extracted from tobacco protoplasts infected with the α, β, γ, γ.Δγa.Δγb.GFPc3 recombinant BSMV (inoculation number 6, see Table 3). Lane 4 contains protein extracted from tobacco protoplasts infected with the α, βΔβa, γ.Δγa.Δγb.GFPc3 recombinant BSMV (inoculation number 13, see Table 3). Lane 5 contains protein extracted from tobacco protoplasts infected with the α, βΔβa, γ.Δγa.Δγb.GFPc3 (2x) recombinant BSMV (inoculation number 17, see Table 3).

The four component satellite approach expresses high levels of GFPc3 in protoplasts, but not in systemically infected plants. A virus whose fourth component contained a γa deletion and a GFPc3 substitution of γb (FIG. 5A) accumulated 2–5 fold more GFPc3 than the γb::GFP fusion virus in protoplasts (compare inoculation number 3 with 6, Table 3), and amounts equivalent to TMV SBS5::GFP (compare inoculation number 6 with 2, Table 3; and lane 3 with 1, FIG. 5D). Although this virus was systemically infectious, it did not express GFPc3 systemically, probably due to the loss of the fourth component.

To increase the possibility that four components would be maintained during systemic expression, a complementary four component approach was also tested. In this approach the two γ RNAs had complementary viral gene deletions; one contained only the ₇b gene while the other contained the γ a gene (FIG. 5B). These two γ RNAs, when combined with the α and β RNAs, produced an attenuated systemic infection in barley (inoculation number 9, Table 3). To use this system to express a heterologous protein, GFPc3 was added to the γ.Δγb RNA in the γb slot (FIG. 5C). This approach resulted in moderate levels of GFPc3 expression in protoplasts (inoculation number 12, Table 3), but was not systemically infectious.

TABLE 3*

| Inoculum | | | | | | GFP expression | | Mosaic |
|---|---|---|---|---|---|---|---|---|
| Test Constructs | | | wt | | | Tobacco | | Barley |
| # | 1 | 2 | 3 | α | β | γ | Protoplasts | Plants | Plants |
| 1 | none | | | X | X | X | | | heavy |
| 2 | TMV-SBS5 GFPc3 | | | | | | ***** | | |
| 3 | γ.γb.GFPc3 | | | X | X | | **** | systemic | heavy |

TABLE 3*-continued

| | Inoculum | | | | | | GFP expression | | Mosaic |
|---|---|---|---|---|---|---|---|---|---|
| | Test Constructs | | | wt | | | Tobacco | Barley | |
| # | 1 | 2 | 3 | α | β | γ | Protoplasts | Plants | Plants |
| 4 | γ.γb.GFPc3 | | β.Δβa | X | | | ***** | bright systemic | heavy |
| 5 | γ.Δγa.Δγb.GFPc3 | | | X | X | | | | |
| 6 | γ.Δγa.Δγb.GFPc3 | | | X | X | X | ***** | | hvy/mod |
| 7 | γ.Δγb | | | X | X | | | | light |
| 8 | | γ.Δγa | | X | X | | | | |
| 9 | γ.Δγb | γ.Δγa | | X | X | | | | light |
| 10 | γ.Δγb.GFPc3 | | | X | X | X | *** | | heavy |
| 11 | γ.Δγb.GFPc3 | | | X | X | | ** | | |
| 12 | γ.Δγb.GFPc3 | γ.Δγa | | X | X | | *** | | |
| 13 | γ.Δγa.Δγb.GFPc3 | | β.Δβa | X | | X | ****** | | heavy |
| 14 | γ.Δγb.GFPc3 | | β.Δβa | X | | X | **** | | heavy |
| 15 | γ.Δγb.GFPc3 | | β.Δβa | X | | | *** | | |
| 16 | γ.Δγb.GFPc3 | γ.Δγa | β.Δβa | X | | | ***** | | |
| 17 | γ.Δγa.Δγb.GFPc3 | γ.Δγa.Δγb.GFPc3 | β.Δβa | X | | X | ******* | | heavy |

*See Table 1 for explanation of abbreviation/symbols.

As mentioned above, replacement of the wild-type RNA β was with a βa deletion mutant appeared to increase expression from the γb subgenomic promoter. In protoplasts, the use of the βa deletion mutant was found to increase GFPc3 expression 2–5 fold for the four-component satellite approach (compare inoculation number 6 with 13, Table 3; and lane 3 with 4, FIG. 5D), and 10-fold for the four component complementary approach (compare inoculation number 12 with 16, Table 3). However, the βa deletion did not confer systemic infectivity to either the complementary fourth component system or systemic GFPc3 expression to the satellite system.

By doubling the dosage of the fourth GFPc3 bearing RNA relative to the other RNAs, an additional 2–5 fold increase in GFPc3 accumulation was observed (compare inoculation number 13 to 17, Table 3; and lane 4 with 5, FIG. 5D). This result suggests that this four component system could be used to express high levels of multiple heterologous proteins in protoplasts from both mono and dicot species. This could be tested by co-transfecting protoplasts with α, β.Δβa, γ and multiple satellite γ RNAs, each expressing a different heterologous protein (e.g. GFP, GUS, CAT, etc.) and transfecting protoplasts. If this were successful, this multi-gene vector system could be used to express various gene combinations to achieve the synthesis of novel compounds and for gene discovery.

Many plant secondary metabolites accumulate to low levels in cell culture lines, compared with the native plant due to differential gene expression in various tissues. For example, many *N. tabacum* cell lines accumulate low (close to undetectable) levels of nicotine (data not shown). Several genes could be introduced into virus expression vectors to add in enzymes or boost expression of functional enzymes that would work to produce complex metabolites. An example of this would be to boost scopolamine biosynthesis in Nicotiana (or other plant) protoplasts. Scopolamine is a secondary metabolite that is synthesized in the root pericycle of *Hyocyamus niger* plants and is a useful plant medicinal compound (Kanegae, et al., 1994). However its accumulation is not significant in many other members of the Solanaceae. The essential genes that contribute to scopolamine synthesis can be cloned and added into separate fourth component satellite constructs, including: phenylalanine ammonia lyase (PAL; phenylalanine biosynthesis), putrescine N-methyl transferase and amine oxidase (putrescine metabolism), and tropinone reductase, hyoscyamine 6S-hydroxylase epoxidase and hyoscyamine 6S-hydroxylase dioxygenase all particularly involved in scopolamine biosynthesis. Over expression of key enzymes, in the feeding pathways (phenylalanine and putrescine biosynthesis) or in the direct synthesis of scopolamine, using the four (or more) component BSMV expression system (described above) would be expected to divert carbon flow from phenylalanine and putrescine synthesis and lead to an accumulation of scopolamine in the Nicotiana cells transfected with these replicating expression vectors. This method could be applied to many different systems where the expression of multiple genes would be required for functionality. It also could include the expression of particular processing enzymes and a substrate protein to produce an active product. In addition, protease inhibitors could be expressed from one component while other components express protein products that are sensitive to protease activity (and thereby inhibited by the protease inhibitor).

Example 9

The Use of the BSMV Vector to Silence Genes Systemically in Monocot Species.

Construction of Monocot Viral Vectors Containing Partial Barley Phytoene Desaturase cDNAs.

Partial cDNAs encoding phytoene desaturase (PDS) were amplified from black hulless barley leaf tissue RNA by RT-PCR using oligonucleotides pairs 193 5' ATATTAATTAACTAAACCCATATTGCTTGAGGCAA 3' (SEQ ID NO: 61) (upstream) and 194 5' TATGCGGCCGCCTAGTGTAGTCACCAGCTAGATAG 3' (SEQ ID NO: 62) (downstream), pairs 193 5' ATATTAATTAACTAAACCCATATTGCTTGAGGCAA 3' (SEQ ID NO: 61) (upstream) and 196 5' TATGCGGCCGCCTACTTTCAGGAGGATTACCATCC 3' (SEQ ID NO: 63) (downstream), pairs 195 5' ATATTAATTAACTGGATGAAAAAGCAGGGTGTTCC 3' (SEQ ID NO: 64) (upstream) and 194 5' TATGCGGCCGCCTAGTGTAGTCACCAGCTAGATAG 3' (SEQ ID NO: 62) (downstream), and pairs 195 5' ATATTAATTAACTGGATGAAAAAGCAGGGTGTTCC 3' (SEQ ID NO: 64) (upstream) and 196 5' TATGCGGCCGCCTACTTTCAGGAGGATTACCATCC 3' (SEQ ID NO: 63) (downstream). The PCR fragments containing portions of the barley PDS cDNA, were digested with PacI and NotI, and inserted between the PacI and NotI sites of γγb.st.P/N-zeo-B and γ.γb.st.N/P-zeoB (FIG. 1C).

Figure 5E:
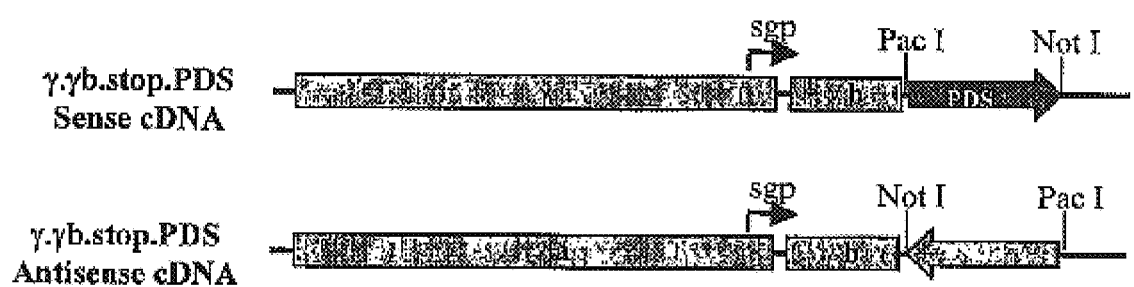
FIG. 5E depicts the genetic structure of two RNAγ constructs: "γ.γb.stop.PDS Sense cDNA" and "γ.γb.stop. PDS Antisense cDNA" (including the restriction sites for PacI and NotI).

The insertion of the partial cDNA fragments eliminated the Zeocin resistance gene and created plasmids with PDS inserts in the positive orientation (γ.γb.st.P/N-bPDS 1, γ.γb.st.P/N-bPDS2, γ.γb.st.P/N-bPDS3, and γ.γb.st.P/N-bPDS4) and negative orientation (γ.γb.st.N/P-bPDS1-as, γ.γb.st.N/P-bPDS2-as, γ.γb.st.N/P-bPDS3-as, and γ.γb.st.N/P-bPDS4-as) (FIG. 5E). These BSMV::PDS hybrid RNAs are designed to express untranslated PDS nucleotide sequences as fusions to the γ subgenomic RNA 1.

Construction of Monocot Viral Vectors Containing Partial Rice Phytoene Desaturase cDNAs.

Partial cDNAs encoding phytoene desaturase (PDS) were amplified from rice leaf tissue RNA by RT-PCR using oligonucleotides pairs 193 5' ATATTAATTAACTAAAC-CCATATTGCTTGAGGCAA 3' (SEQ ID NO: 61) (upstream) and 194 5' TATGCGGCCGCCTAGTGTAGT-CACCAGCTAGATAG 3' (SEQ ID NO: 62) (downstream), pairs 193 5' ATATTAATTAACTAAACCCATATTGCT-TGAGGCAA 3' (SEQ ID NO: 61) (upstream) and 196 5' TATGCGGCCGCCTACTTTCAGGAGGATTACCATCC 3' (SEQ ID NO: 63) (downstream), pairs 195 5' ATATTAAT-TAACTGGATGAAAAAGCAGGGTGTTCC 3' (SEQ ID NO: 64) (upstream) and 194 5' TATGCGGCCGCCTAGT-GTAGTCACCAGCTAGATAG 3' (SEQ ID NO: 62) (downstream), and pairs 195 5' ATATTAATTAACTGGAT-GAAAAAGCAGGGTGTTCC 3' (SEQ ID NO: 64) (upstream) and 196 5' TATGCGGCCGCCTACTTTCAG-GAGGATTACCATCC 3' (SEQ ID NO: 63) (downstream). The PCR fragments containing portions of the rice PDS cDNA, were digested with PacI and NotI, and inserted between the PacI and NotI sites of γ.γb.st.P/N-zeo-B and γ.γbystγN/P-zeoB (FIG. 1C). The insertion of the partial cDNA fragments eliminated the Zeocin resistance gene and created plasmids with PDS inserts in the positive orientation (γ.γb.st.P/N-rPDS1, γ.γb.st.P/N-rPDS2, γ.γb.st.P/N-rPDS3, and γ.γb.st.P/N-rPDS4) and negative orientation (γ.γb.st.N/P-rPDS1-as, γ.γb.st.N/P-rPDS2-as, γ.γb.st.N/P-rPDS3-as, and γ.γb.st.N/P-rPDS4-as) (FIG. 5E). These BSMV::PDS hybrid RNAs are designed to express untranslated PDS nucleotide sequences as fusions to the γ subgenomic RNA 1.

Construction of Monocot Viral Vectors Containing Full Length and Partial Maize Phytoene Desaturase cDNAs.

Partial cDNAs encoding phytoene desaturase (PDS) were amplified from corn leaf tissue RNA by RT-PCR using oligonucleotides pairs 175 5' ATATTAATTAACATGGA-CACTGGCTGCCTGTC 3' (SEQ ID NO: 65) (upstream) and 180 5' TATGCGGCCGCCTACAAAGCAAT-CAAAATGCACTG 3' (SEQ ID NO: 66) (downstream) encoding PDS Met$^1$-Leu$^{290}$, pairs 177 5' ATATTAATTAA-CAAGGTAGCTGCTTGGAAGGATG 3' (SEQ ID NO: 67) (upstream) and 178 5' TATGCGGCCGCCTAGCAGGT-TACTGACATGTCTGC 3' (SEQ ID NO: 68) (downstream) encoding PDS Lys$^{1\ 34}$-Cys$^{431}$, and pairs 179 5' ATATTAAT-TAACCAGTGCATTTTGATTGCTTTG 3' (SEQ ID NO: 69) (upstream) and 176 5' TATGCGGCCGCCTAAGATGG-GACGGGAACTTCTCC 3' (SEQ ID NO: 70) (downstream) encoding PDS Gln$^{284}$-Ser$^{571}$. The full length cDNA encoding phytoene desaturase (PDS) was amplified from corn leaf tissue RNA by RT-PCR using oligonucleotides pairs 175 5' ATATTAATTAACATGGACACTGGCTGCCTGTC 3' (SEQ ID NO: 65) (upstream) and 176 5' TATGCGGCCGC-CTAAGATGGGACGGGAACTTCTCC 3' (SEQ ID NO: 70) (downstream) encoding PDS Met$^1$-Ser$^{571}$. The 0.8 Kb PCR fragments containing portions of the corn PDS cDNA, and the 1.6 Kb PCR fragment containing the full length corn PDS ORF, were digested with PacI and NotI, and inserted between the PacI and NotI sites of γ.γb.st.P/N-zeo-B and γ.γb.st.N/P-zeoB (FIG. 1C). The insertion of the partial and full length PCR fragments eliminated the Zeocin resistance gene and created plasmids with PDS inserts in the positive orientation (γ.γb.st.P/N-mPDS-N, γ.γb.st.P/N-mPDS-M, γ.γb.st.P/N-mPDS-C, and γ.γb.st.P/N-mPDS) and negative orientation (γ.γb.st.N/P-mPDS-N-as, γ.γb.st.N/P-mPDS-M-as, γ.γb.st.N/P-mPDS-C-as, and γ.γb.st.N/P-mPDS-as) (FIG. 5E). These BSMV::PDS hybrid RNAs are designed to express untranslated PDS nucleotide sequences as fusions to the γ subgenomic RNA 1.

Construction of Monocot Viral Vectors Containing Full-Length and Partial N. benthamiana Phytoene Desaturase cDNAs.

The full length cDNA encoding N. benthamiana PDS was amplified from the plasmid pPDS Nb2, which contains an insert with the sequence depicted by SEQ ID NO: 3 of U.S. Pat. No. 5,539,093. To amplify the nucleic acid encoding PDS Met$^1$-Val$^{580}$ (encompassed by SEQ ID NO: 3 of U.S. Pat. No. 5,539,093) oligonucleotides pairs 189 5' ATAT-TAATTAACATGCCCCAAATTGGACTTGTTTC 3' (SEQ ID NO: 71) (upstream) and 190 5' TATGCGGCCGCCTAC-TAAACTACGCTTGCTTCTGC 3' (SEQ ID NO: 72) (downstream) were used. cDNA was placed under the control of the BSMV γb subgenomic promoter by subcloning into the PacI and NotI sites of both γ.γb.st.P/N-zeo-B and γ.γb.st.N/P-zeoB (FIG. 1C). The partial cDNAs encoding N. benthamiana PDS were amplified from the plasmid pPDS Nb2 using oligonucleotides pairs 189 5' ATATTAATTAA-CATGCCCCAAATTGGACTTGTTTC 3' (SEQ ID NO: 71) (upstream) and 192 5' TATGCGGCCGCCTAGGGTTTAT-GAAGTTAAGTGCC 3' (SEQ ID NO: 73) (downstream) encoding PDS Lys$^{134}$-Cys$^{431}$, and pairs 191 5' ATATTAAT-TAACAAGGCACTTAACTTCATAAACCC 3' (SEQ ID NO: 74) (upstream) and 190 5' TATGCGGCCGCCTAC-TAAACTACGCTTGCTTCTGC3' (SEQ ID NO: 72) (downstream) encoding PDS Gln$^{284}$-Ser$^{571}$. The 1.7 Kb PCR fragment containing the full length N. benthamiana PDS and the 0.9 Kb PCR fragments containing portions of the N. benthamiana PDS cDNA were digested with PacI and NotI and inserted between the PacI and NotI sites of γ.γb.st.P/N-zeo-B and γ.γb.st.N/P-zeoB (FIG. 1C). The insertion of the partial and full-length cDNA fragments eliminated the Zeocin resistance gene and created plasmids with PDS inserts in the positive orientation (γ.γb.st.P/N-nPDS1, γ.γb.st.P/N-nPDS2, and γ.γb.st.P/N-nPDS3) and negative orientation (γ.γb.st.N/P-nPDS1-as, γ.γb.st.N/P-nPDS2-as, and γ.γb.st.N/P-nPDS3-as) (FIG. 5E). These BSMV::PDS hybrid RNAs are designed to express untranslated PDS nucleotide sequences as fusions to the γ subgenomic RNA 1.

Inoculation Protocol.

Infectious BSMV RNAs from cDNA clones were prepared by in vitro transcription using T7 DNA-dependent RNA polymerase (Ambion) as decribed previously (Petty, et al; 1989). Transcripts of each of the three BSMV genomes were mixed in a 1:1:1 ratio. A 7.5 µl aliquot of the transcription mix was combined with 45 µL of FES and directly applied to 12 day old black hulless barley plants. Barley cultivars used include: Abrabische, Agio, Alexis, Atlas, B83, Berwick, Binder, Black Hulless, Chariot, Cooper, Delta, Derkado, Golden Promise, Gotlan DS, Haise, Hanna, Intensiv, Irish Archer, Kenia, Lyallpur, Monte Cristo, Opal, Optic, Prisma, Spring Wheat, Tankard, Tern, Tyne, Vivet, and Vollkorn.

Purification and Analysis of Carotenoids from Transfected Barley Plants.

The carotenoids were isolated from 50 mg of systemically infected leaf tissue 18 days post inoculation and analyzed by HPLC chromatography. Carotenoids were extracted in the dark in methanol and identified by their peak retention time and absorption spectra on a Zorbax 4.6×15 cm C-18 column using acetonitrile/methanol/2-propanol (85:10:5) as a developing solvent at a flow rate of 2 ml/min. They had identical retention times to a synthetic phytoene standard and β carotene standards from tomato and carrot.

Preparation of cDNA Library in Monocot Vector.

*Oryza sativa* ecotype Indica and Japonica (0) seeds were sown and the meristem, root, leaves and panicles were collected at appropriate time points. Tissue was washed in deionized water and frozen in liquid nitrogen. High quality total RNA was isolated using a hot borate method (Wilkins and Smart, 1996). mRNA was isolated from total RNA using oligo $(dT)_{25}$ magnetic beads (Miltenyi) according to manufacturer's instructions. The purified polyA$^+$ RNA was then used for cDNA synthesis by conventional strand replacement reactions (Okayama and Berg, 1982; Gubler and Hoffman, 1983). Double strand cDNA was synthesized either with NotI-$(dT)_{25}$ primer based on the manufacturer's instruction (Gibco-BRL superscript system). Typically, 5 µg of poly A$^+$ RNA was annealed and reverse transcribed at 37° C. with Superscript II reverse transcriptase. Double stranded cDNAs were ligated to a 500 to 1000-fold molar excess SalI adaptor, restriction enzyme NotI digested and size-selected by column fractionation.

cDNAs from four different tissues: 7 weeks root, 7 weeks leaf, meristem and mixed panicles were pooled and then cloned directionally into the SalI-NotI sites of the BSMV expression vector, γ.γb.st.P/N-zeo-B and γ.γb.st.N/P-zeoB (FIG. 1C). The ratio between the vector and insert is 280 ng to 60 ng and the transformation efficiency is ~2×10$^6$ cfu/µg. Each ligation was transformed into chemically competent *E. Coli* cells, DH5 α according to manufacturer's instruction (Gibco-BRL). To ascertain the cloning efficiency of cDNA into each vector and the average insert size, 96 random colonies were picked and grown by standard molecular biology methods. DNA was isolated from bacteria using a Qiagen BioRobot 9600. DNA was digested with NotI and PacI restriction endonucleases (recognition sites flank the cDNA insertion). The digestions were separated on agarose gels and visualized by ethidium bromide staining. Approximately 600 independent clones were analyzed by restriction digestion as described above. The average insert size in the vector was ~1 kb, with many inserts with 2 kb or greater sized inserts.

Results and Discussion.

BSMV was used to silence the endogenous phytoene desaturase (PDS) gene in barley. Black Hulless barley plants were inoculated with BSMV RNA α and β.Δβa, and a γ RNA designed to express one of several portions of the rice PDS cDNA (γ.γb.st.P/N.bPDS1, γ.γb.st.P/N.bPDS2, γ.γb.st.P/N.bPDS3, γ.γb.st.P/N.bPDS4, γ.γb.st.P/N.bPDS1-as, γ.γb.st.P/N.bPDS2-as, γ.γb.st.P/N.bPDS3-as, and γ.γb.st.P/N.bPDS4-as: collectively referred to as BSMV::mPDS). The various BSMV::bPDS hybrid viruses spread throughout the non-inoculated leaves as determined by the appearance of mosaic symptoms and by local lesion assay on *Chenopodium amranticolor*. The presence of the PDS insert was confirmed by Reverse Transcriptase (RT)-PCR using primers specific to the BSMV γ RNA and flanking the inserted PDS cDNA fragment. The initial viral symptomology (1–7 days post inoculation) resulting from the BSMV::bPDS hybrid viruses was indistinguishable from a wild type BSMV infection. However, between 8–10 days post inoculation, the BSMV::bPDS plants began to exhibit streaks and patches of unusually white tissue. The affected areas lacked the necrosis or desiccation that is often associated with BSMV induced bleaching and, instead, appeared more like the bleached tissue found in plants treated with the chemical inhibitor of PDS, norflurazon. These white streaks were observed to some degree in all the BSMV::bPDS infected barley plants, regardless of whether the PDS fragment was sense or antisense. The PDS gene is part of the carotenoid biosynthetic pathway, which produces colored compounds that protect the green pigment, chlorophyll from photobleaching (Bartley and Scolnik, 1995). The presence of the bleached tissues suggested that the endogenous PDS gene was no longer functional in these tissues.

Figure 6:
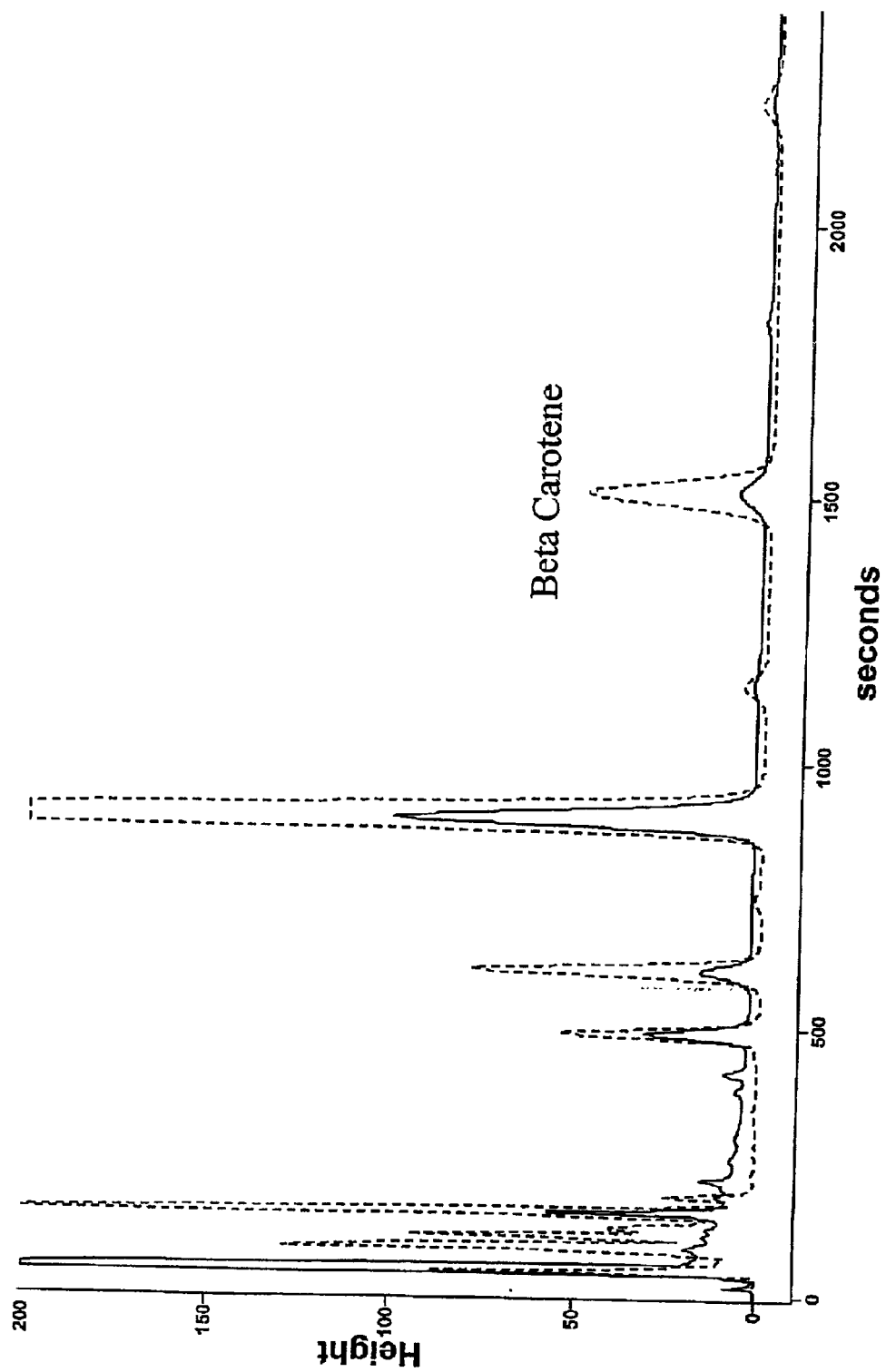
FIG. 6 depicts the HPLC analysis of phytoene accumulation in barley at 16 days post inoculation (dpi) inoculated with BSMV::GFP (leaf 5; green invention, the targeting nucleotide sequence comprises the nucleotide sequence of a gene of a first species of organism, and the gene of interest to be silenced is a gene of a second species of organism. In chloroplast, vacuole, pinocytic vesicle, rough endoplasmic recticulum, smooth endoplasmic recticulum, Golgi body, apoplast, or the like. Preferably the protein of interest comprises a signal peptide that can direct the protein of interest to be localized to a specific location within the host cell, such as an organelle. Preferably the signal peptide (SP) is at the N-terminal of the protein of interest. Preferably the protein of interest is of a suitable size or number of amino acids as exemplified by the size and number of amino acids of bovine lysozyme, chicken interferon, human growth hormone, and protease inhibitor.
Figure 7:
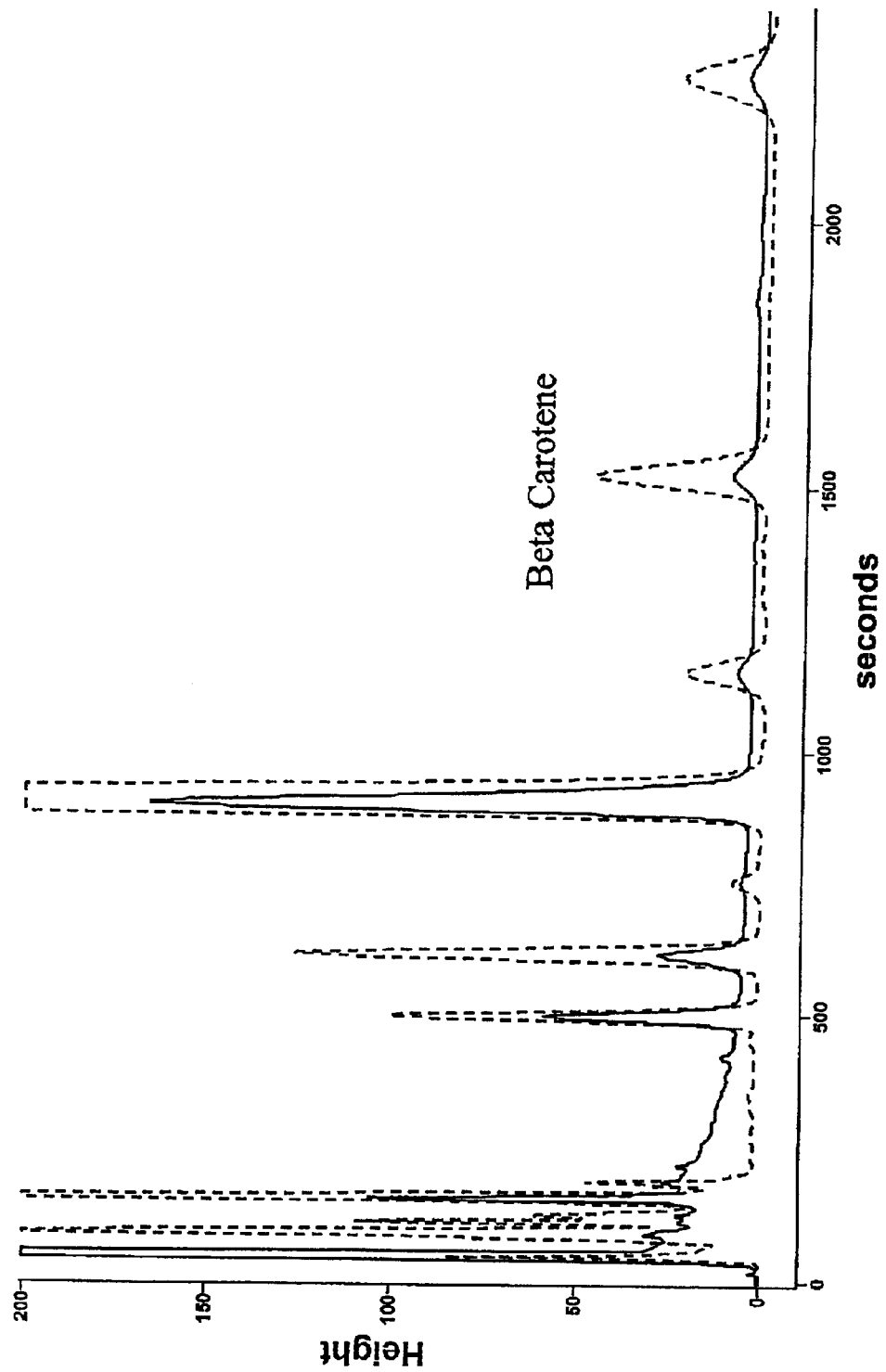
Figure 8:
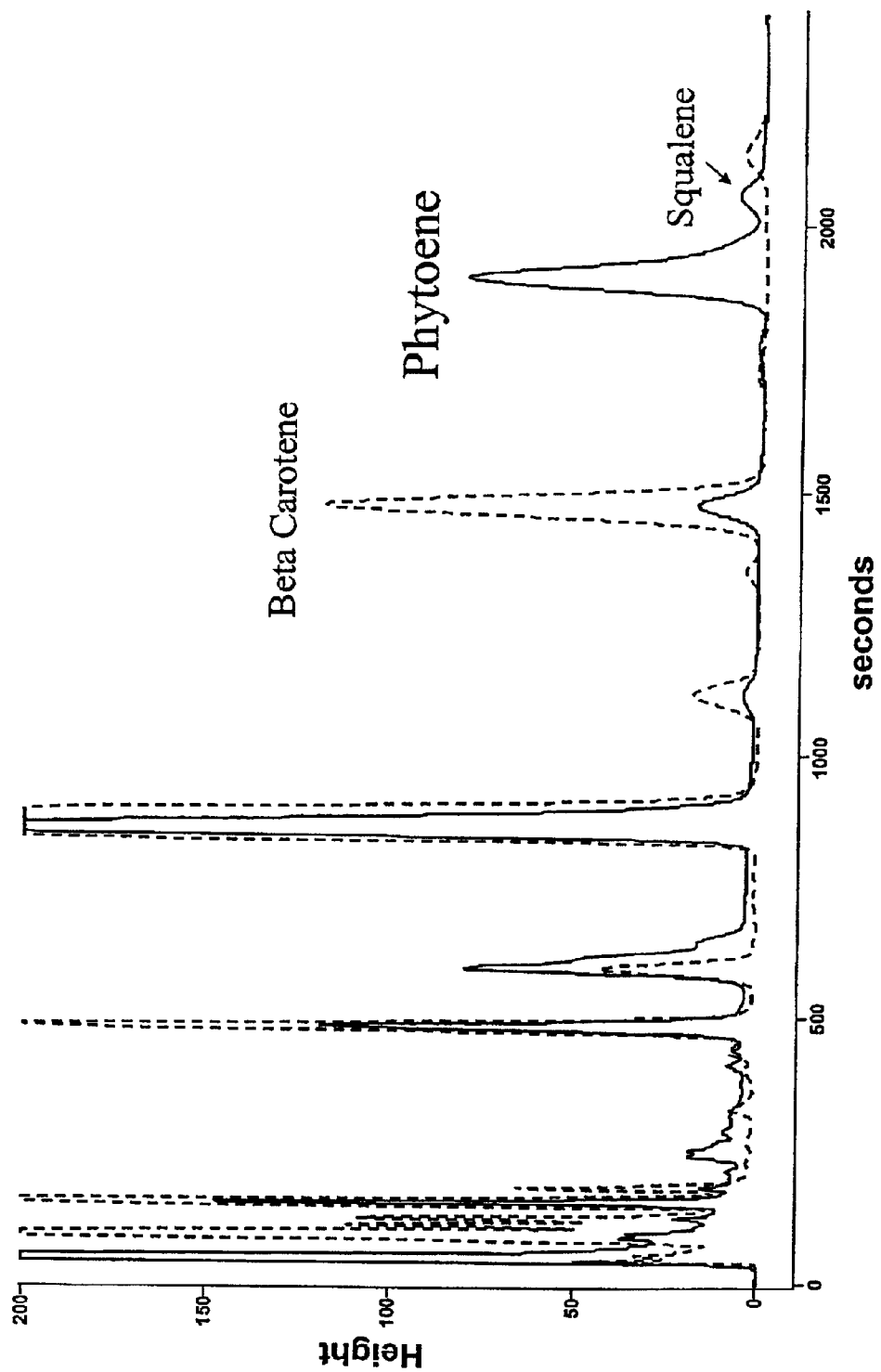
Figure 9:
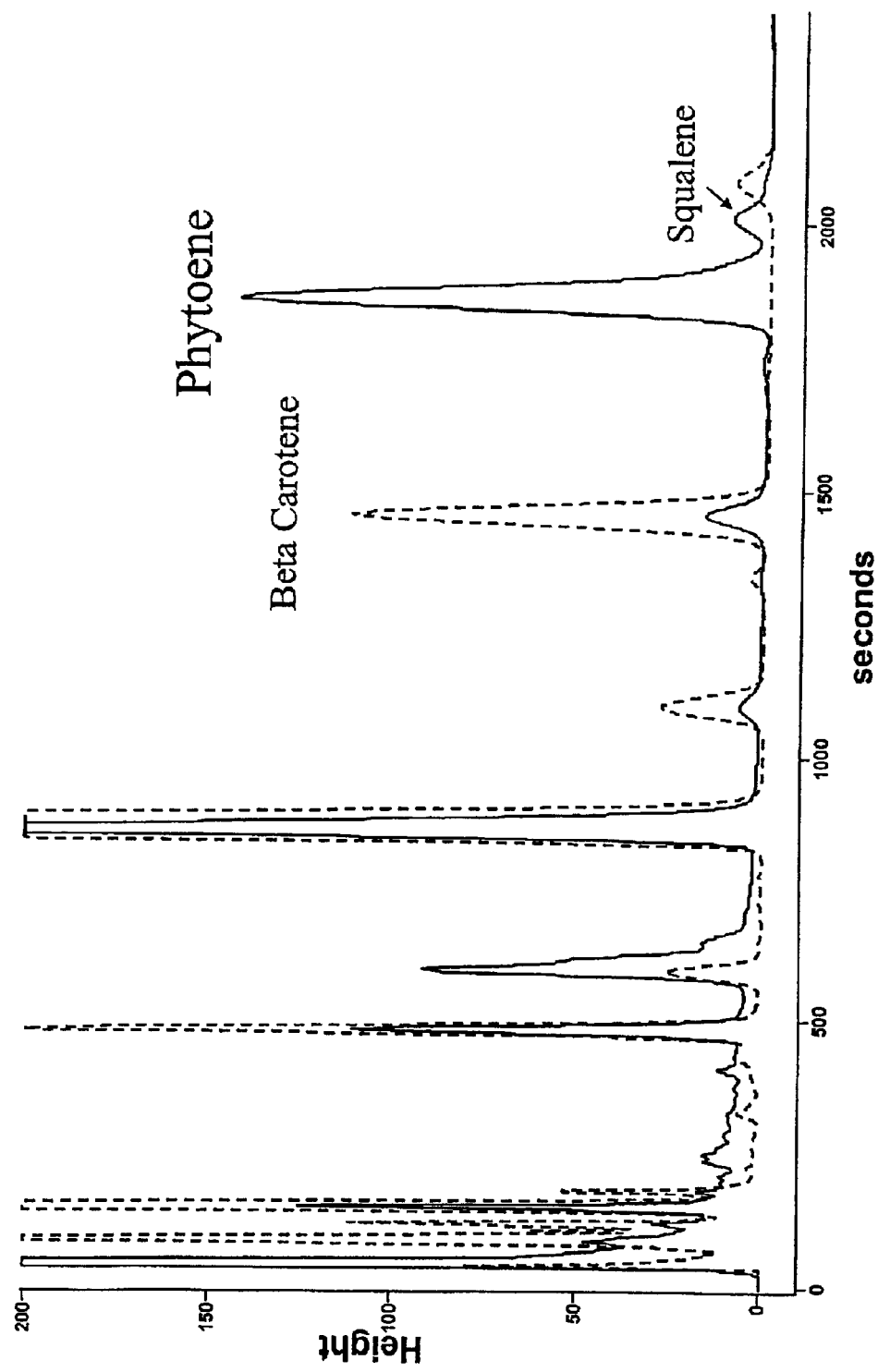
Figure 10:
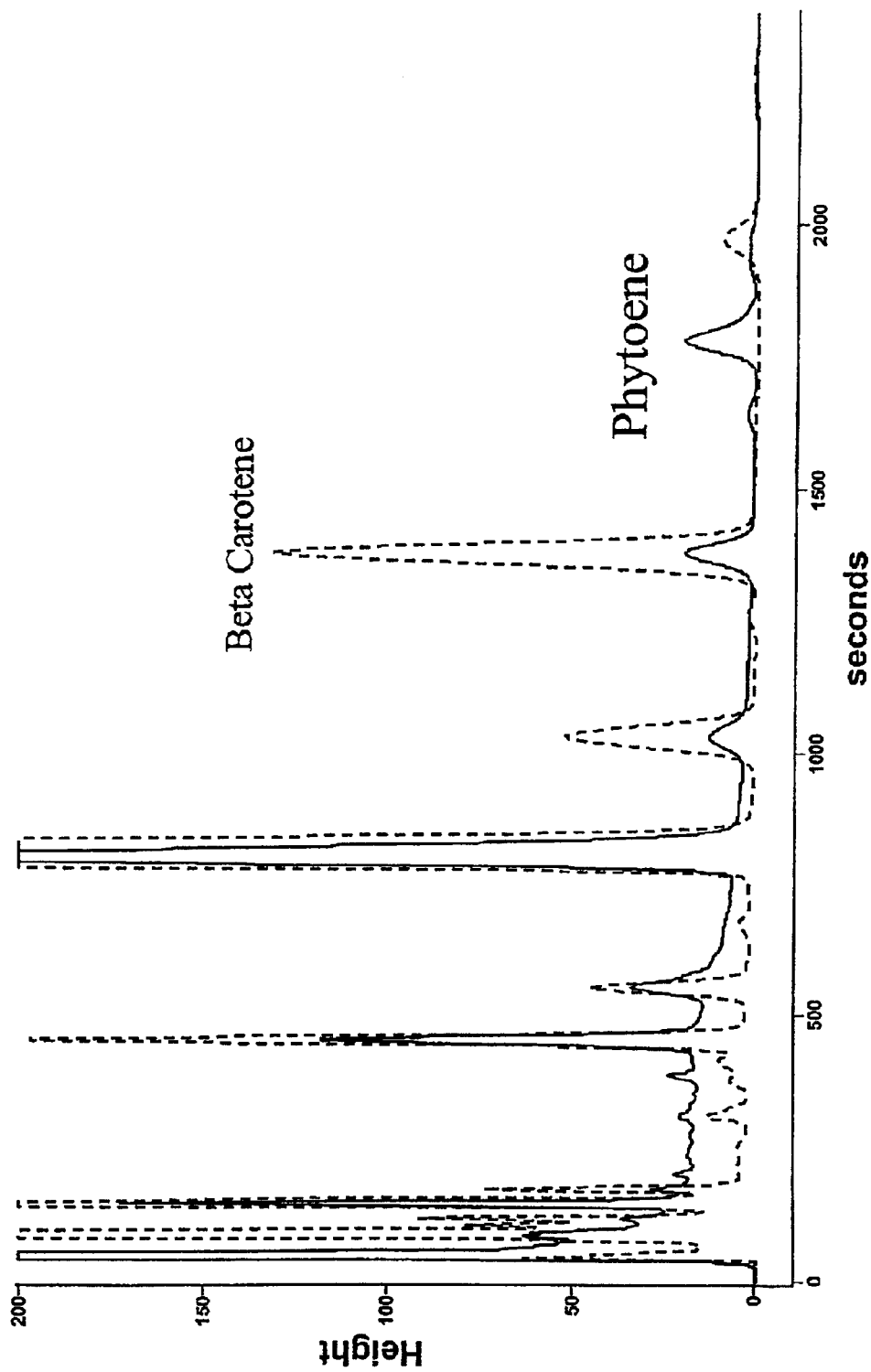
Figure 11:
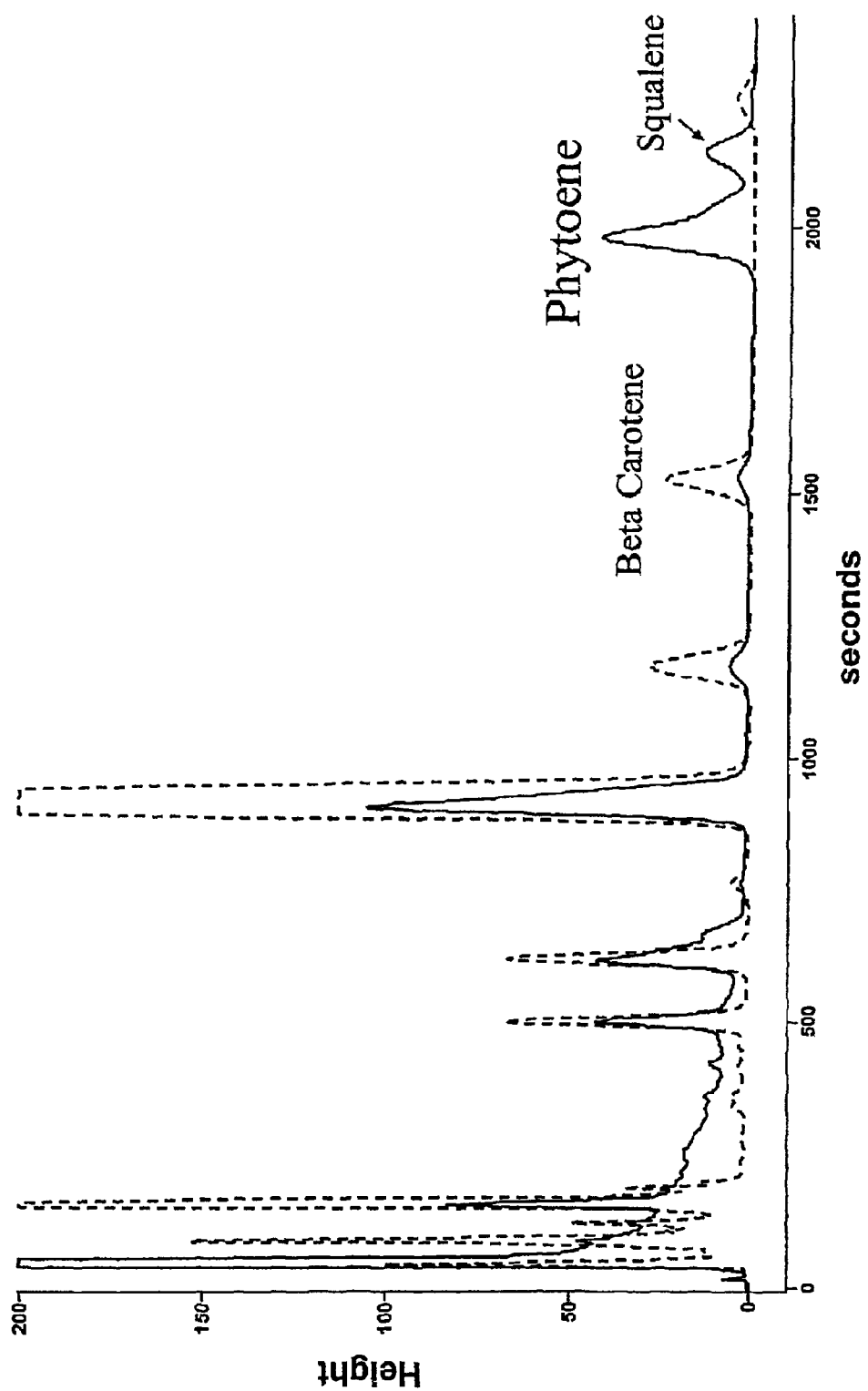
Figure 12:
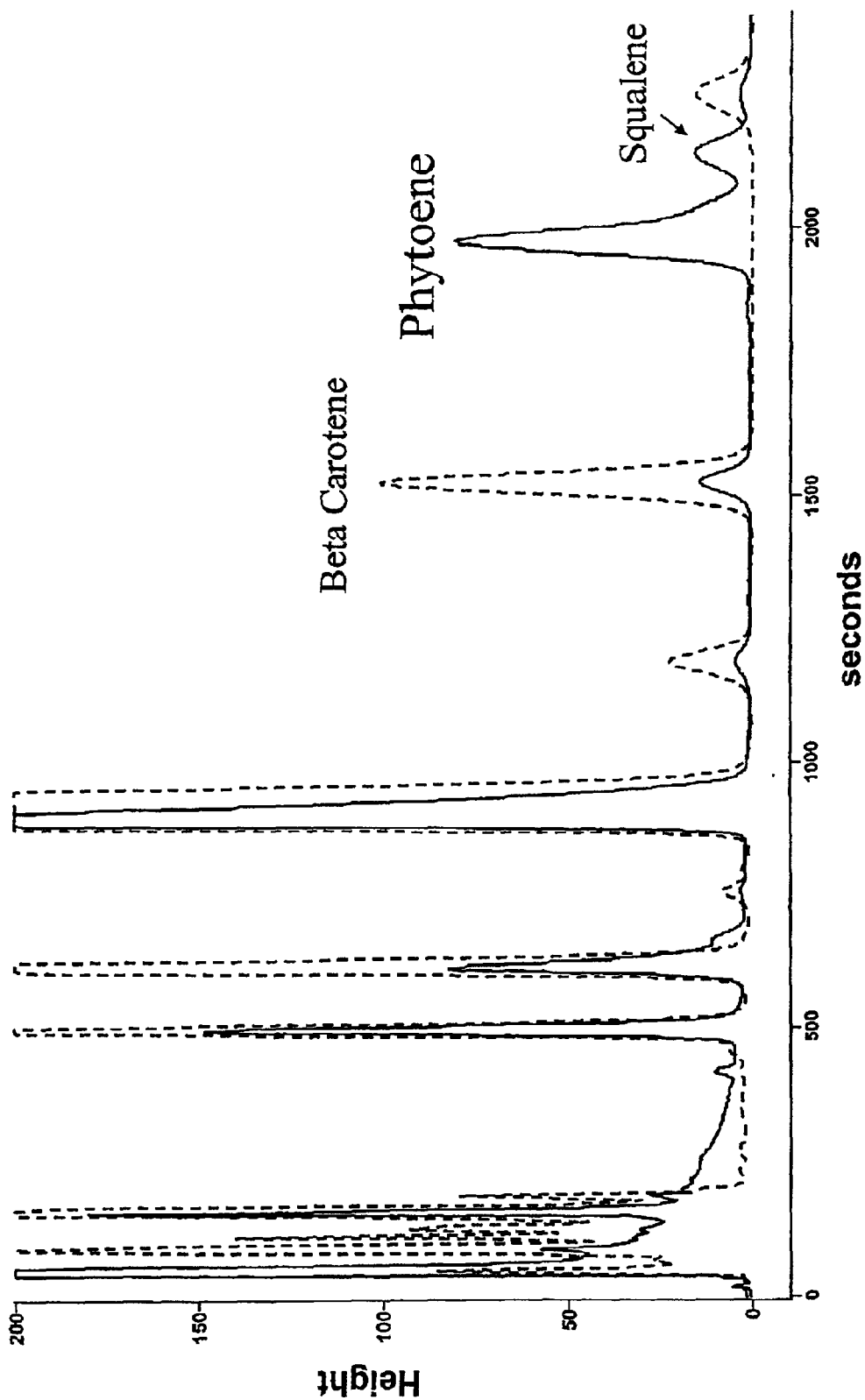
Figure 13:
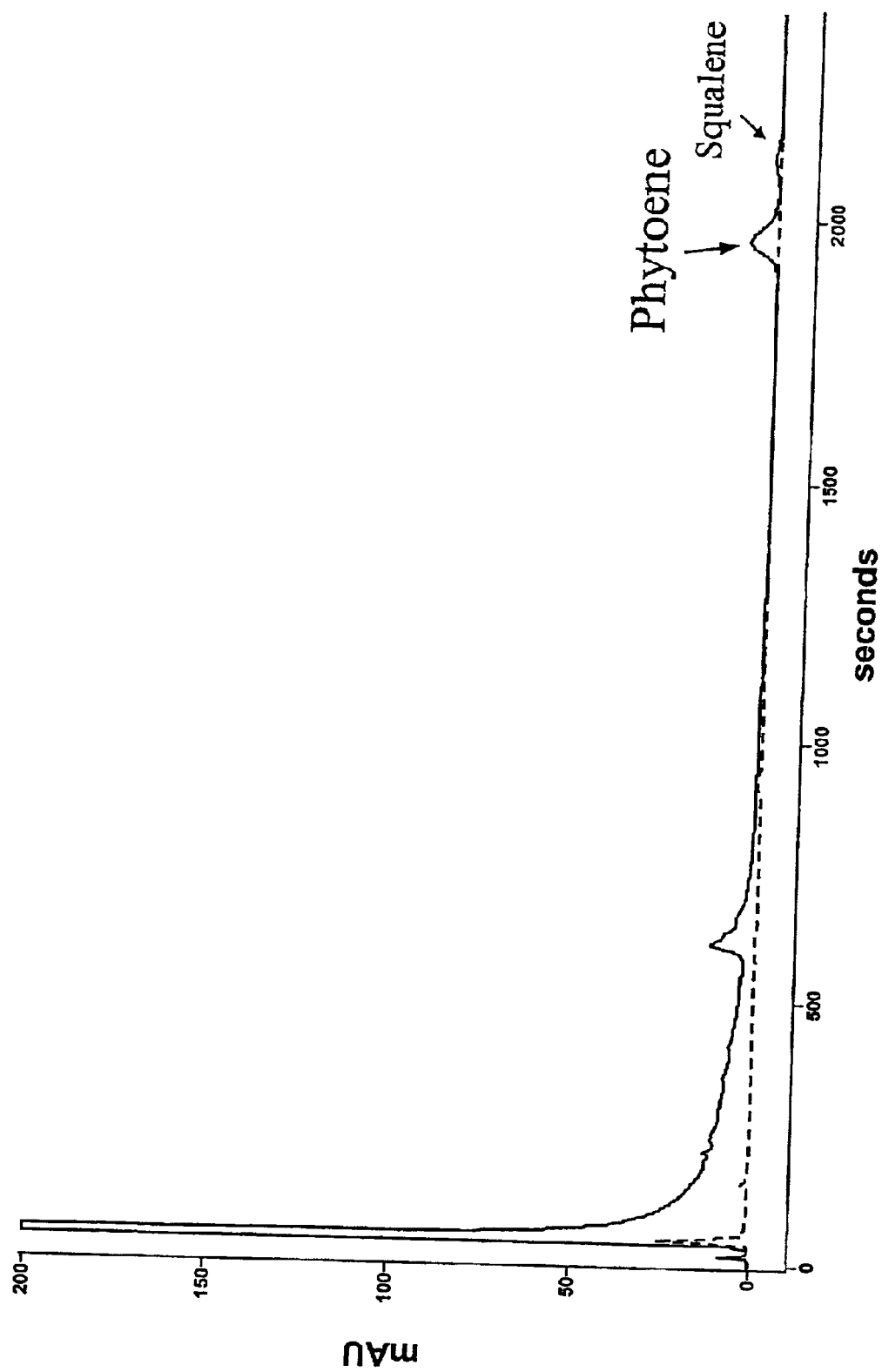

In Black Hulless, phytoene desaturase gene (PDS) silencing is first observed as streaks of bleached tissue in the uppermost leaf (leaf 3 or 4, numbered from the base) between 8–11 days post inoculation (dpi). The accumulation of phytoene, the substrate for PDS, can also be detected in these leaves at this time by HPLC analysis. Phytoene accumulation can be measured as the number of Area Units (AU) under the HPLC retention peak. Uninoculated barley plants, and barley plants infected with wild-type BSMV or BSMV::GFP (FIG. 2A) have an average of approximately 60 AU of phytone, and can occasionally be as high as 200 AU (inoculation 9–11, Table 4, FIGS. 6–7). In plants inoculated with BSMV::bPDS hybrid viruses, average pytoene levels accumulate to 5–40 fold above the control plant, depending on time post infection, leaf position, and the PDS fragment (inoculations 1–8, Table 4, FIGS. 8–10). These changes in phytoene levels were similar to that observed with norflurazon treated plants (Table 4, FIGS. 11-13), thereby providing biochemical evidence for the genetic silencing of the PDS endogene. Bleached areas continue to appear and expand in leaves 4, 5 and sometimes 6, over the period from 12 to 20 dpi, and occasionally up to 25 dpi. After 18–20 dpi, phytoene levels begin to become lower (Table 4). Phytoene accumulation and photobleaching are spatially and temporally related, and unevenly distributed throughout BSMV-bPDS infected plants. Leaves with visual bleaching show high levels of phytoene accumulation, while other leaves on the same plant may or may not have any phytoene accumulation.

Our results demonstrating bleaching phytoene accumulation in barley plants transfected with partial antisense and sense phytoene desaturase suggest that plant viral vectors can be used to manipulate biosynthetic pathways in monocots through cytoplasmic inhibition of endogenous gene expression.

TABLE 4

| | | Inoculum | | Phytoene accumulation in HPLC area units | | | |
| --- | --- | --- | --- | --- | --- | --- | --- |
| | | viral RNAs | | (average of 2 plants, uppermost leaf) | | | |
| # | Test Constructs | α | β.Δβa | 11 dpi | 14 dpi | 17 dpi | 21 dpi |
| 1 | γ.γb.st.bPDS1-A6 | X | X | 995 | 2425 | 804 | 1495 |
| 2 | γ.γb.st.bPDS1-as-B10 | X | X | 1429 | 1280 | 1739 | 104 |

TABLE 4-continued

| | Inoculum | | | Phytoene accumulation in HPLC area units | | | |
|---|---|---|---|---|---|---|---|
| | | viral RNAs | | (average of 2 plants, uppermost leaf) | | | |
| # | Test Constructs | α | β.Δβa | 11 dpi | 14 dpi | 17 dpi | 21 dpi |
| 3 | γ.γb.st.bPDS2-G11 | X | X | 2020 | 1434 | 379 | 986 |
| 4 | γ.γb.st.bPDS2-as-C5 | X | X | 1676 | 775 | nt | 658 |
| 5 | γ.γb.st.bPDS3-D5 | X | X | 371 | 1382 | 1419 | 267 |
| 6 | γ.γb.st.bPDS3-as-E8 | X | X | 465 | 1247 | 1208 | 145 |
| 7 | γ.γb.st.bPDS4-C1 | X | X | 1653 | 1161 | 1375 | 1342 |
| 8 | γ.γb.st.bPDS4-as-A4 | X | X | 1265 | 1449 | 506 | 316 |
| 9 | γ.γb.GFPc3 | X | X | 53 | 47 | 67 | 68 |
| 10 | γ | X | X | 135 | 10 | 80 | 41 |
| 11 | Mock | | | 59 | 71 | 30 | 10 |
| 12 | Norflurazon | | | 2355 | 2180 | 2439 | 2205 |

Endogene homology and BSMV-induced gene silencing.

Experiments were designed to evaluate the effect of gene homology of the insert in the virus vector with the endogene that is targeted for silencing. Various PDS gene fragments from barley (Hordeum vulgare), rice (Oryza sativa), corn (Zea mays), and N. benthamiana were cloned into γ.γb.st.P/N-zeo-B and γ.γb.st.N/P-zeoB (FIG. 1C). This produced in an array of viruses expressing sense and antisense PDS fragments, each of which was inoculated onto black hulless barley plants. All of the viruses bearing rice and corn PDS fragments were able to silence barley PDS, as judged by the appearance of bleached tissue and the accumulation of phytoene (Table 5). Thus BSMV could heterologous PDS fragments to silence the endogenous barley PDS. For barley, rice and corn fragments, increased homology between virus encoded PDS fragments and genomic encoded PDS results in increased bleaching intensity, phytoene accumulation, and consistency from plant to plant (Table 5). Viruses expressing N. benthamiana PDS fragments, those least homologous to barley did not silence barley PDS. Together these results suggest that homology with the endogenous gene may be a limiting factor in BSMV mediated gene silencing in barley.

TABLE 5

| | | | Phytoene Area Units | |
|---|---|---|---|---|
| | BSMV::PDS | | | standard |
| Insert* | Insert source | Homology** | average*** | error |
| bPDS | Hordeum vulgare | 100% | 1231 | 100 |
| rPDS | Oryza sativa | 90% | 897 | 150 |
| mPDS | Zea mays | 88% | 497 | 136 |
| nPDS | Nicotiana benthamiana | 74% | 90 | 8 |
| GFP | na | na | 105 | 20 |
| none | na | na | 62 | 3 | na: not applicable
*Four insert fragments tested, each in both orientation, for each PDS gene (Table)
**nucleatide homolgy to barley PDS sequence (partial)
***Average area units based on 32 samples from 3 timepoints for each insert The ability to silence endogenous barley genes using cDNA fragments from a heterologous species suggests that BSMV could be used to discover new genes based on functional knockout of the barley homolog. To demonstrate the utility of this vector as a gene discovery tool, a library of BSMV γ RNAs expressing rice cDNAs, in the sense and antisense orientation, was generated in γ.γb.st.P/N-zeo-B and γ.γb.st.N/P-zeoB (FIG. 1C). The γ::cDNA library was generated in a 96 well format to aid in handling and inoculated onto trays of 96 plants. By screening approximately 1100 unique cDNA inserts expressed by BSMV::cDNA in barley, 25 novel visible phenotypes were detected. To date three of these phenotypes have been confirmed.

To this point, experiments have been conducted using a β RNA with a coat protein deletion (β.Δβa). To determine the effect of the BSMV coat protein on BSMV mediated silencing of PDS, experiments were performed with the wild type β RNA as well. Experiments with BSMV expressing corn PDS suggest that BSMV mediated gene silencing is enhanced by the deletion of the βa gene (coat protein) (Table 6). In general, coat protein deletion increases both the frequency and extent of bleaching and phytoene accumulation (Table 6) in black hulless barley.

TABLE 6

| | Inoculum | Fraction of plants showing PDS silencing phenotype at 19 dpi | | |
|---|---|---|---|---|
| # | Test Constructs | β | β.Δβa | none |
| 1 | γ.γb.st.PDS-n-B5 | 0/6 | 2/6 | |
| 2 | γ.γb.st.PDS-n-B7 | 1/6 | 2/6 | |
| 3 | γ.γb.st.PDS-m-C5 | 5/6 | 6/6 | |
| 4 | γ.γb.st.PDS-m-C9 | 2/6 | 5/6 | |
| 5 | γ.γb.st.PDS-c-D6 | 1/6 | 1/6 | |
| 6 | γ.γb.st.PDS-c-D12 | 1/6 | 3/6 | |
| 7 | γ.γb.st.PDS-nR-E1 | 0/6 | 0/6 | |
| 8 | γ.γb.st.PDS-nR-E2 | 1/6 | 0/6 | |
| 9 | γ.γb.st.PDS-mR-F2 | 3/6 | 3/6 | |
| 10 | γ.γb.st.PDS-mR-F5 | 2/6 | 3/6 | |
| 11 | γ.γb.st.PDS-cR-G8 | 1/6 | 3/6 | |
| 12 | γ.γb.st.PDS-cR-G12 | 0/6 | 1/6 | |
| 13 | γ.γb.P/N::c3-A5 | 0/6 | 0/6 | |
| 14 | γ.γb.P/N::c3as-A2 | 0/6 | 0/6 | |
| 15 | γ STP | 0/6 | 0/6 | |
| 16 | γ.γb.c3.ΔM-1 | 0/6 | 0/6 | |
| 17 | mock | | | 0/6 |
| 18 | uninoculated, NF treated | | | 2/2 |
| total number of PDS silenced plants: | | 17 | 29 | |

BSMV Vector Expression and Gene Silencing in Alternative Barley Cultivars.

Data presented to this point has been using the BSMV vector in the Black Hulless cultivar of barley. However, the BSMV vector is capable of expression and endogene silencing in other cultivars of barley. Barley cultivars were screened for BSMV susceptibility, GFPc3 expression and PDS silencing by inoculating 2 plants each with wild-type BSMV, BSMV::GFPc3, and BSMV::bPDS4, both with and without the coat protein. BSMV infection and BSMV-mediated PDS silencing and GFPc3 fluorescence were observed in all cultivars tested. BSMV-mediated PDS silencing and GFPc3 expression are enhanced in all barley cultivars by the deletion of the βa gene (coat protein) from the vector (Table 7). In the absence of the coat protein, on average, a higher percentage of tissue has GFPc3 fluorescence and this tissue is brighter. In general, the deletion of the coat protein gene also increases virus pathology and movement. The increase in both GFPc3 accumulation and pathology are most pronounced in less susceptible barley cultivars. Initial testing with wild-type BSMV, γb::GFP and γb::bPDS (barley PDS gene) revealed several cultivars that appear to be improved hosts compared to black hulless (Table 7). Promising cultivars maintain high or higher levels of GFPc3 expression and PDS silencing, but have a reduction in virus pathology; these will require further testing on larger scale for confirmation.

TABLE 7

| | Inoculum Phytoene Area Units | | | | |
|---|---|---|---|---|---|
| | α, γ.γb.st.bPDS4 | | α, γ.γb.GFP with | | |
| Cultivar | with β | with βΔβa | with β | βΔβa | none |
| Gotlan DS | 993 | 903 | | | |
| Arabische | 140 | 1455 | | | |
| Vollkorn | 167 | 684 | | | |
| B83 | 1145 | 1250 | | | |
| Derkado | 104 | 705 | | | |
| Tern | 264 | 140 | | | |
| Haisa | 254 | 865 | | | |
| Kenia | 469 | 1412 | | | |
| Delta | 157 | 156 | | | |
| Asio | 2154 | 672 | | | |
| Tankard | 166 | 262 | | | |
| Binder | 361 | 1761 | | | |
| Hanna | 476 | 827 | | | |
| Berwick | 255 | 1428 | | | |
| Intensiv | 419 | 784 | | | |
| Alexis | 167 | 788 | | | |
| Golden Promise | 531 | 315 | | | |
| Spring Wheat | 256 | 721 | | | |
| Lyallpur | 355 | 789 | | | |
| Irish Archer | 487 | 1605 | | | |
| Livet | 331 | 1222 | | | |
| Opal | 574 | 1446 | | | |
| Monte Cristo | 1223 | 1238 | | | |
| Cooper | 999 | 1035 | | | |
| Prisma | 235 | 1026 | | | |
| Optic | 150 | 1199 | | | |
| Atlas | 450 | 1204 | | | |
| Chariot | 117 | 1243 | | | |
| Tyne | 421 | 992 | | | |
| Black Hulless | 810 | 665 | | | |
| Black Hulless GFP | | | 104 | 38 | |
| Black Hulless mock | | | | | 65 |
| Black Hulless Uninoculated | | | | | 40 |
| Norflurazon | | | | | 1576 |

Although the invention has been described with reference to the presently preferred embodiments, it should be understood that various modifications can be made without departing from the spirit of the invention.

All publications, patents, patent applications, and web sites are herein incorporated by reference in their entirety to the same extent as if each individual publication, patent, patent application, or web site was specifically and individually indicated to be incorporated by reference in its entirety.

Literature Cited

Ahlquist, P., Luckow, V., and Kaesberg, P. (1981). Complete nucleotide sequence of brome mosaic virus RNA3. J. Mol. Biol. 153:23–28.

Bartley, G. E., and Scolnik, P. A. (1995). Plant carotenoids: pigments for photoprotection, visual attraction, and human health. Plant Cell 7(7): 1027–38.

Chaplin, P. J., Camon, E. B., Villarreal-Ramos, B., Fling, M., Ryand, M. D., and Collins, R. A. (1999). Production of interleukin-12 as a self-processing 2A polypeptide. Interferon Cytokine Res. 19(3):235–41.

Choi I., Stenger D.C., Morris T. J., French R. (2000). A plant virus vector for systemic expression of foreign genes in cereals. The Plant Journal 23(4), 547–555.

Crameri A., Whitehorn E. A., Tate E, and Stemmer W. P. (1996). Improved green fluorescent protein by molecular evolution using DNA shuffling. Nature Biotechnol. 14 (3): 315–9.

DeFelipe, P., and Izquierdo, M. (2000). Tricistronic and tetracistronic retroviral vectors for gene transfer. Hum. Gene Ther. 11(13): 1921–31.

DeFelipe, P., Martin, V., Cortes, M. L., Ryan, M., and Izquierdo, M. (1999). Use of the 2A sequence from foot-and-mouth disease virus in the generation of retroviral vectors for gene therapy. Gene ther. 6(2):198–208.

DeNoto, F. M., Moore, D. D., and Goodman, H. M. (1981) Nucleic Acids Res. 9, 3719–3730.

Digby, M. R. and Lowenthal, J. W. (1995) J. Interferon Cytokine Res. 15 (11), 939–945.

Donald, R. G., and Jackson A. O. (1998). The barley stripe mosaic virus gamma β gene encodes a multifunctional cycteine-rich protein that affects pathogenesis. Plant Cell 6(11):1593–606.

Donnelly, M. L., Gani, D., Flint, M., Monaghan, S., and Ryan, M. D. (1997) The cleavage activities of aphthovirus and cardiovirus 2A proteins. J. Gen Virol. 78 (Pt 1)13–21.

Gopinath, K., Wellink, J., Porta, C., Taylor, K. M., Lomonossoff, G. P., and van Kammen A. (2000). Engineering cowpea mosaic virus RNA-2 into a vector to express heterologous proteins in plants. Virol. 267(2):159–73.

Graham J. S., Pearce G., Merryweather J., Titani K., Ericsson L. and, Ryan C. A. (1985). Wound-induced proteinase inhibitors from tomato leaves. I. The cDNA-deduced primary structure of pre-inhibitor I and its post-translational processing. J Biol. Chem. 260(11):6555–60.

Halpin, C., Cooke, S. E., Barakate, A., El Amrani, A., and Ryan, M. D. (1999) Self-processing 2A-polyproteins—a system for co-ordinate expression of multiple proteins in transgenic plants. Plant J. 17(4):453–9.

Haupt, S., Duncan, G. M., Jackson, A. O., Holzberg, S., and Oparka, K. J. (2001) Sieve-element unloading in sink leaves of barley is symplastic. Plant Physiology (in press).

Jackson, A. O., and Hunter, B. G. (1989). Hordeivirus relationships and genome organization. Annu. Rev. Phytopathol. 27:95–121.

Jackson, A. O., Petty, I. T. D., Jones, R. W., Edwards, M. C., and French R. (1991). Analysis of barley stripe mosaic virus pathogenicity. Sem. Virol. 2:107–19.

Jarvik J. W., and Telmer C. A. (1998) Epitope tagging. Annu Rev Genet. 1998;32:601–18.

Joshi, R. L., Joshi V., and Ow D. W. (1998). BSMV genome mediated expression of a foreign gene in dicot and monocot plant cells. EMBO. 9:2663–9.

Kanegae, T., Kajiya, H., Amano, Y., Hashimoto, T. and Yamada, Y. (1994) Plant Physiol. 105(2): 483–490.

Kokuho, T., Watanabe, S., Yokomizo, Y., and Inumaru, S. (1999) Production of biologically active, heterodimeric porcine interleukin-12 using a monocistronic baculoviral expression system. Vet. Immunol Immunopathol. 72(3–4): 289–302.

Li, F., Browning, G. F., Studdert, M. J., and Crabb, B. S. (1996). Equine rhinovirus 1 is more closely related to foot-and-mouth disease virus than to other picornaviruses. Proc. Natl. Acad. Sci. USA 93(3):990–5

Mattion, N. M., Harnish, E. C., Crowley, J. C., and Reilly, P. A. (1996) Foot-and-mouth disease virus 2A protease mediates cleavage in attenuated Sabin 3 poliovirus vectors engineered for delivery of foreign antigens. J. Virol. 70(11): 8124–7.

McKinney H H, and Greeley, L. W., (1965). Biological characteristics of barley stripe mosaic virus strains and their evolution. Technical Bulletin U.S. Department of Agriculture 1324.

Palmenberg, A. C. (1990). Proteolytic processing of picornaviral polyprotein. Annu. Rev. Microbiol. 44:603–23.

Palomar, M. K., Brakke M. K., and Jackson, A. O. (1977). Base sequence homology in the RNAs of barley stripe mosaic virus. Virol.77(2):471–80.

Petty, I. T., Hunter, B. G., Wei, N., and Jackson A. O. (1989). Infectious barley stripe mosaic virus RNA transcribed in vitro from full-length genomic cDNA clones. Virol. 171(2):342–9.

Petty, I. T., French, R., Jones, R. W., and Jackson A. O. (1990). Identification of barley stripe mosaic virus genes involved in viral RNA replication and movement. EMBO Journal 9: 3453–3457

Pogue, G. P., Lindbo, J. A., Dawson, W. O., and Turpen, T. H. (1998) Tobamovirus transient expression vectors: tools for plant biology and high-level expression of foreign proteins in plants. In "Plant Molecular Biology Manual" (S. B. Gelvin and R. A. Schilperoot, eds) L4, pp. 1–27. Kluwer Academic Publishers, Dordrecht, The Netherlands.

Ryan, M. D., and Drew, J. (1994) Foot-and-mouth disease virus 2A oligopeptide mediated cleavage of an artificial polyprotein. EMBO Journal: 13(4):928–33, Ryan, M. D., King, A. M., and Thomas, G. P. (1991). Cleavage of foot-and-mouth disease virus polyprotein is mediated by residues located within a 19 amino acid sequence. 72(Pt 11):2727–32.

Weiland, J. J., and Edwards M C (1996). A single nucleotide substitution in the alpha a gene confers oat pathogenicity to barley stripe mosaic virus strain ND18. MPMI 9(1):62–67.

Zhou H., and Jackson, A. O., (1996). Analysis of cis-acting elements required for replication of barley stripe mosaic virus RNAs. Virol. 16(2):367–79.

Zhou, H., and Jackson, A. O., (1998). Expression of the barley stripe mosaic virus RNA beta "triple gene block. Virol. 16(2):367–79.

What is claimed is:

1. A polynucleotide encoding a promoter operatively linked to a transcription unit, wherein the promoter comprises a promoter functional in a plant or plant cell; and wherein the transcription unit encodes a fusion protein comprising:
   (a) a viral protein obtained from a plant single-stranded RNA virus, wherein the plant single-stranded RNA virus is a barley stripe mosaic virus (BSMV),
   (b) a protein of interest, and
   (c) an autoproteolytic peptide comprising no more than 20 amino acids, wherein the autoproteolytic peptide comprises a 2A autoproteolytic peptide from a foot and mouth disease virus (FMDV), wherein (c) is fused between (a) and (b).

2. The polynucleotide according to claim 1, where in the autoproteolytic peptide comprises the amino acid sequence of SEQ ID NO: 1.

3. The polynucleotide according to claim 1, wherein the fusion protein comprises no more than one viral protein.

4. The polynucleotide of according to claim 1, wherein the viral protein is a BSMV gamma-b protein.

5. The polynucleotide according to claim 1, wherein the autoproteolytic peptide is fused to the C-terminus of the viral protein.

6. The polynucleotide according to claim 1, wherein the autoproteolytic peptide is fused to the N-terminus of the viral protein.

7. The polynucleotide of according to claim 1, wherein the viral protein is a BSMV beta-b protein.

8. The polynucleotide according to claim 7, wherein the autoproteolytic peptide is fused to the N-terminus of the viral protein, and where the protein of interest is fused to the N-terminus of the autoproteolytic peptide.

9. The polynucleotide according to claim 1, wherein the protein of interest is a plant protein.

10. The polynucleotide according to claim 9, wherein the plant protein is a structural protein, enzyme, or a protein involved with pigmentation.

11. A recombinant viral nucleic acid comprising the polynucleotide according to claim 8.

12. A plant or plant cell containing the recombinant viral nucleic acid according to claim 11.

13. A recombinant virus comprising the recombinant viral nucleic acid according to claim 11, wherein the recombinant virus is capable of systemic expression of the fusion protein.

14. A plant or a plant cell infected with a recombinant virus according to claim 13.

15. The polynucleotide according to claim 1, wherein the fusion protein can be expressed in a plant or a plant cell.

16. A recombinant viral nucleic acid comprising the polynucleotide according to claim 1.

17. A recombinant virus comprising the recombinant viral nucleic acid according to claim 16.

18. A plant cell infected with a recombinant virus according to claim 17.

19. The plant cell according to claim 18 wherein the plant cell is a monocot plant cell.

20. A plant infected with a recombinant virus according to claim 17.

21. The plant according to claim 20 wherein the plant is a monocot plant cell.

22. A polynucleotide according to claim 1 wherein the protein of interest is a viral protein.

23. A recombinant viral nucleic acid comprising the polynucleotide according to claim 22.

24. A recombinant virus comprising the recombinant viral nucleic acid according to claim 23.

25. A viral genome comprising at least one duplicated genomic nucleic acid component, wherein the duplicated genomic nucleic acid component encodes a promoter operatively linked to a fusion protein, wherein the fusion protein comprises
   (a) a viral protein obtained from a plant single-stranded RNA virus, wherein the plant single-stranded RNA virus is a barley stripe mosaic virus (BSMV),
   (b) a protein of interest, and
   (c) an autoproteolytic peptide comprising no more than 20 amino acids,
wherein the autoproteolytic peptide comprises a 2A autoproteolytic peptide from a foot and mouth disease virus (FMDV), wherein (c) is fused between (a) and (b).

* * * * *